US007060455B1

(12) United States Patent
Doetsch et al.

(10) Patent No.: US 7,060,455 B1
(45) Date of Patent: Jun. 13, 2006

(54) BROAD SPECIFICITY DNA DAMAGE ENDONUCLEASE

(75) Inventors: Paul W. Doetsch, Atlanta, GA (US); Angela M. Avery, Sligo (IE); Balveen Kaur, Decatur, GA (US)

(73) Assignee: Emory University, Atlanta, GA (US)

( * ) Notice: Subject to any disclaimer, the term of this patent is extended or adjusted under 35 U.S.C. 154(b) by 593 days.

(21) Appl. No.: 09/724,296

(22) Filed: Nov. 28, 2000

Related U.S. Application Data

(63) Continuation-in-part of application No. 09/327,984, filed on Jun. 8, 1999, now Pat. No. 6,368,594.

(60) Provisional application No. 60/134,752, filed on May 18, 1999, provisional application No. 60/088,521, filed on Jun. 8, 1998.

(51) Int. Cl.
  *C12N 19/16* (2006.01)
  *C12O 1/66* (2006.01)
  *C12P 19/34* (2006.01)

(52) U.S. Cl. .................... 435/18; 435/196; 435/91.1

(58) Field of Classification Search ................ 435/195, 435/6, 18, 91.1; 536/23.2
See application file for complete search history.

(56) References Cited

U.S. PATENT DOCUMENTS

| 4,863,874 A | 9/1989 | Wassef et al. ............. 436/501 |
| 4,921,757 A | 5/1990 | Wheatley et al. ......... 428/402.2 |
| 5,077,211 A | 12/1991 | Yarosh ...................... 435/193 |
| 5,190,762 A | 3/1993 | Yarosh ...................... 424/450 |
| 5,225,212 A | 7/1993 | Martin et al. .............. 424/450 |

FOREIGN PATENT DOCUMENTS

| WO | WO 99/04626 | * 2/1999 |

OTHER PUBLICATIONS

Hendrich B. et al, Identification and Characterization of a Family of Mammalian Methyl-CpB Binding Proteins, Mol. Cell, Biol., 1998, 18, 6538-6547, Nov. 1998.*
Bellacosa A. et al, MED1, a Novel human Methyl-CpG-binding Endonuclease, Interacts with DNA Mismatch Repair Protein MLH1, Proc. Natl. Acad. Sci. USA, 1999, 96, 3969-3974, Feb. 1999.*
Ford C. F. et al. Fusion Tails for the Recovery and Purification of Recombinant Proteins, protein Expression and Purification, 1991, 2, 95-107.*
Kanno et al. Repair of apurinic/apirimidinic sites by UV damage endonuclease; a repair protein for UV and oxidative damage, Nucleic Acid Research, 1999, 27, 3096-3103.*
Alleva and Doetsch (1998) "Characterization of *Schizosaccharomyces pombe* Rad2 Protein, a FEN-1 Homolog" *Nucleic Acids Research* 26:3645-3650.

Avery et al. (1999) "Substrate Specificity of Ultraviolet DNA Endonuclease (UVDE/Uvelp) from *Schizosaccharomyces pombe*" *Nucleic Acids Research* 27:2256-2264.
Bowman et al. (1994) "A New ATP-Independent DNA Endonuclease From *Schizosaccharomyces pombe* That Recognizes Cyclobutane Pyrimidine Dimers and 6-4 Photoproducts" *Nucleic Acids Research* 22:3026-3032.
Brash et al. (1991) "A Role for Sunlight in Skin Cancer: UV-Induced p53 Mutations in Squamous Cell Carcinoma" *Proc. Natl. Acad. Sci.* USA 88:10124-10128.
Chang and Lu (1991) "Base Mismatch-Specific Endonuclease Activity in Extracts from *Saccharomyces cerevisiae*" *Nucleic Acids Research* 19:4761-4766.
Davey et al. (1997) "The Fission Yeast UVDR DNA Repair Pathway Is Inducible" *Nucleic Acids Research* 25:1002-1008.
Doetsch, P. W. (1995) "What's Old Is New: An Alternative DNA Excision Repair Pathway" *Trends Biochem. Sci.* 20:384-386.
Doetsch et al. (1985) "T4 DNA Polymerase (3'-5') Exonuclease, an Enzyme for the Detection and Quantitation of Stable DNA Lesions: the Ultraviolet Light Example" *Nucleic Acids Research* 13:3285-3304.
Freyer et al. (1995) "An Alternative Eukaryotic DNA Excision Repair Pathway" *Molecular and Cellular Biology* 15:4572-4577.
Genbank Accession No. AAA08907.
Genbank Accession No. AAD22195.
Genbank Accession No. BAA74539.
Genbank Accession No. D78571.
Genbank Accession No. U78487.
Genbank Accession No. Z49782.

(Continued)

*Primary Examiner*—Rebecca E. Prouty
*Assistant Examiner*—Malgorzata Walicka
(74) *Attorney, Agent, or Firm*—Greenlee, Winner and Sullivan, P.C.

(57) ABSTRACT

The present disclosure describes DNA damage endonucleases which exhibit broad specificity with respect to the types of structural aberrations in double stranded DNA. These enzymes recognize double stranded DNA with distortions in structure, wherein the distortions result from photoproducts, alkylation, intercalation, abasic sites, mismatched base pairs, insertion deletion loops, cisplatin adducts and other types of base damage (for example, uracil resulting from cytosine deamination). The UVDE (Uvelp) of *Schizosaccharomyces pombe*, certain truncated forms of that UVDE (lacking from about 100 to about 250 amino acids of N-terminal sequence) and certain endonucleases from *Homo sapiens, Neurospora crassa, Bacillus subtilis, Bacillus anthracis, Methanococcus jannaschii*, and *Deinococcus radiodurans*. The present disclosure further provides methods for cleaving double stranded DNA having structural distortions as set forth herein using the exemplified endonucleases or their stable, functional truncated derivatives.

3 Claims, 18 Drawing Sheets

OTHER PUBLICATIONS

Grafstrom et al. (1982) "Enzymatic Repair of Pyrimidine Dimer-Containing DNA" *The Journal of Biological Chemistry* 257:13465-13474.

Hamilton et al. (1992) "A Eukaryotic DNA Glycosylase/Lyase Recognizing Ultraviolet Light-Induced Pyrimidine Dimers" *Nature* 356:725-728.

Kaur et al. (1998) "Expression, Purification, and Characterization of Ultraviolet DNA Endonuclease from *Schizosaccharomyces pombe*" *Biochemistry* 37:11599-11604.

Kaur et al. (Jul. 1999), "A Uvelp-Mediated Mismatch Repair Pathway in *Schizosaccharomyces pombe,*" *Molec. Cell. Biology* 19(7):4703-4710.

Kaur et al. (2000), "Ultraviolet Damage Endonuclease (Uvelp): A Structure and Strand-Specific DNA Endonuclease," *Biochemistry* 39(9):5788-5796.

Kim et al. (1994) "Characterization of (6-4) Photoproduct DNA Photolyase" *The Journal of Biological Chemistry* 269:8535-8540.

Nakabeppu et al. (1982) "Purification and Characterization of Normal and Mutant Forms of T4 Endonuclease V" *The Journal of Biological Chemistry* 257:2556-2562.

Sancar, A. (1994) "Mechanisms of DNA Excision Repair" *Science* 266:1954-1956.

Sancar and Tang (1993) "Nucleotide Excision Repair" *Photochemistry and Photobiology* 57:905-921.

Sancar, G.B. (1990) "DNA Photolyases: Physical Properties, Action Mechanism, and Roles in Dark Repair" *Mutation Research* 236:147-160.

Schär and Kohli (1993) "Marker Effects of G to C Transversions on Intragenic Recombination and Mismatch Repair in *Schizosaccharomyces pombe*" *Genetics* 133:825-835.

Szankasi and Smith (1995) "A Role for Exonuclease I from *S. pombe* in Mutation Avoidance and Mismatch Correction" *Science* 267:1116-1169.

Takao et al. (1996) "Characterization of a UV Endonuclease Gene From the Fisson Yeast *Schizosaccharomyces pombe* and Its Bacterial Homolog" *Nucleic Acids Research* 24:1267-1271.

Yajima et al. (1995) "A Eukaryotic Gene Encoding an Endonuclease That Specifically Repairs DNA Damaged by Ultraviolet Light" *The EMBO Journal* 14:2393-2399.

Yao and Kow (1997) "Further Characterization of *Escherichia coli* Enconuclease V" *The Journal of Biological Chemistry* 272:30774-30779.

Yao and Kow (1994) "Strand-Specific Cleavage of Mismatch-Containing DNA by Deoxyinosine 3'-Endonuclease from *Escherichia coli*" *The Journal of Biological Chemistry* 269:31390-31396.

Yasui and McCready (1998) "Alternative Repair Pathways for UV-Induced DNA Damage" *BioEssays 20.4* 20:291-297.

Yeh et al. (1994) "Mammalian Topoisomerase I Has Base Mismatch Nicking Activity" *The Journal of Biological Chemistry* 269:15498-15504.

Yeh et al. (1991) "Two Nicking Enzyme Systems Specific for Mismatch-Containing DNA in Nuclear Extracts from Human Cells" *The Journal of Biological Chemistry* 266:6480-6484.

Yonemasu et al. (1997) "Characterization of the Alternative Excision Repair Pathway of UV-Damaged DNA in *Schizosaccharomyces pombe*" *Nucleic Acids Research* 25:1533-1558.

Yoon et al. (1999) "Processing of UV Damage in Vitro by FEN-1 Proteins as Part of an Alternative DNA Excision Repair Pathway" *Biochemistry* 38(15).

* cited by examiner

5' ...CTGCACGAAT^TAAGCAATTC... 3'

```
            c b a
            ↓↓↓
5' GTACCCGGGGATCCTCCTXAGTCGACCTGCA* 3'
3' CATGGGCCCCTAGGAGGAYTCAGCTGGACGT  5'
```

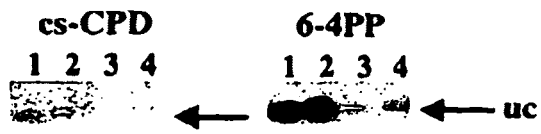
FIG. 8A       FIG. 8B
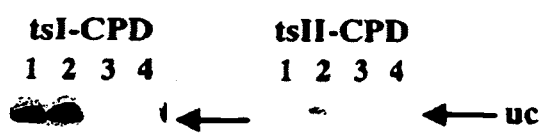
FIG. 8C       FIG. 8D
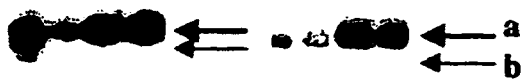
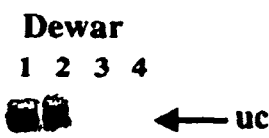
FIG. 8E
*5'...GCCTGCACGAAT^TAAGCAATTCG...3'

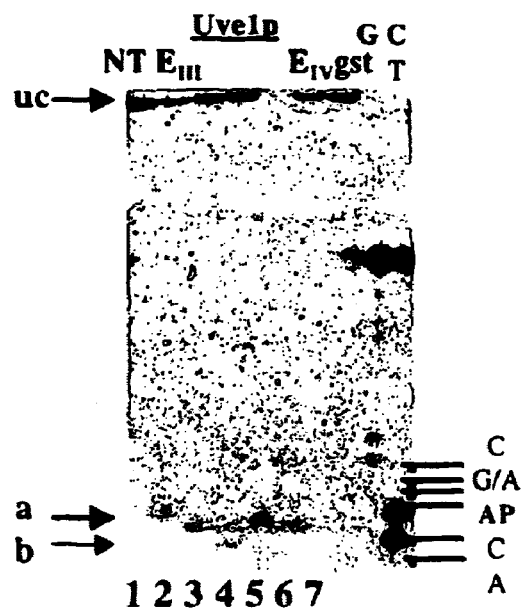
FIG. 10A
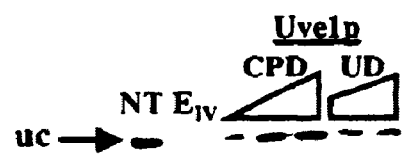
FIG. 10B
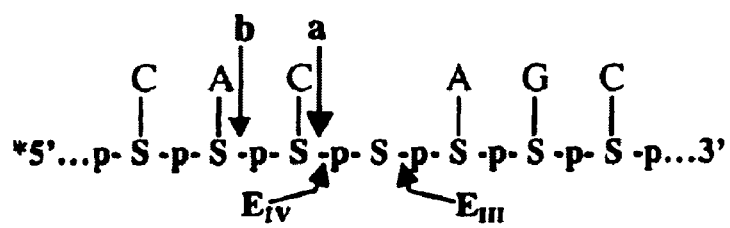

```
         Dde I
           b
           ↓
5' CGTTAGCATGCCTGCACGAACTAAGCAATTCGTAATGCATT 3'
3' GCAATCGTACGGACGTGCTTAATTCGTTAAGCATTACGTAA 5'
                        ↑↑
                         c
                       Dde I
```

FIG. 14A
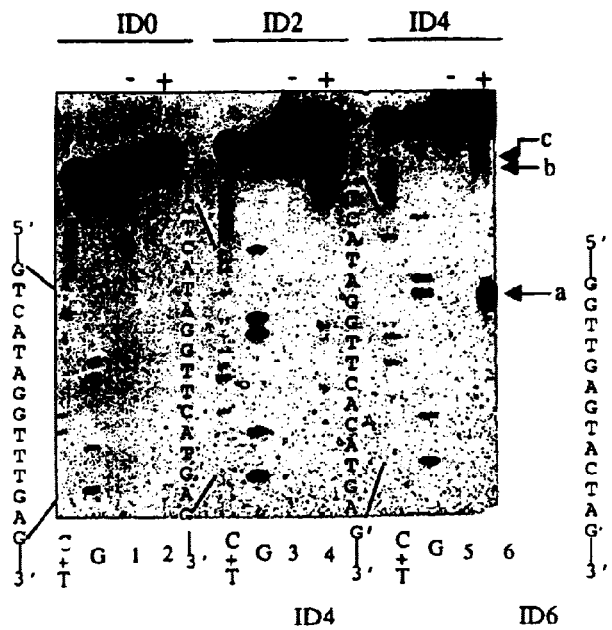
FIG. 14B
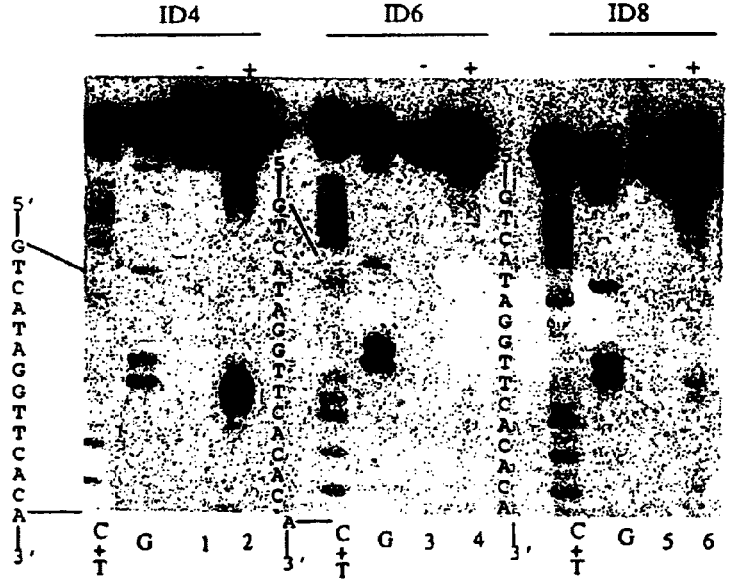
5' CACAGACTCCCTCTGTCATAGGTTXTGAGTTTATATGGAA* 3'
3' GTGTCTGAGGGAGACAGTATCCAA-ACTCAAATATACCTT  5'
FIG. 14C

5' CGTTAGAACTCCGTCACGAATTAAGCAATTXAGTAATGCATT 3'
3' GCAATCTTGAGGCAGTGCTTAATTCGTTAA-TCATTACGTAA 5'

BROAD SPECIFICITY DNA DAMAGE ENDONUCLEASE

CROSS REFERENCE TO RELATED APPLICATIONS

The present application is a continuation in part of U.S. patent application Ser. No. 09/327,984, filed Jun. 8, 1999, now U.S. Pat. No. 6,368,594, which claims priority from U.S. Provisional Application No. 60/088,521, filed Jun. 8, 1998, and from U.S. Provisional Application No. 60/134,752, filed May 18, 1999.

ACKNOWLEDGMENT OF FEDERAL RESEARCH SUPPORT

This invention was made, at least in part, with funding from the National Institutes of Health (Grant Nos. CA 55896, AR 42687 and CA 73041), and the National Cancer Institute. Accordingly, the United States Government has certain rights in this invention.

BACKGROUND OF THE INVENTION

The field of the present invention is the area of DNA repair enzymes. In particular, the invention concerns the identification of stable ultraviolet DNA endonuclease polypeptide fragments, their nucleotide sequences and recombinant host cells and methods for producing them and for using them in DNA repair processes.

The integrity of its genetic material must be maintained in order for a biological species to survive. However, DNA is continuously subject to damage by endogenous and exogenous agents that can lead to mutations, neoplasia or cell death [Smith et al. (1996) *Biochemistry* 35:4146–4154; Brash et al. (1991) *Proc. Natl. Acad. Sci. USA* 88:10124–10128]. One potential source of mutations is nucleotide misincorporation by DNA polymerases during DNA replication or repair. In addition, primer/template slippage can occur at repetitive DNA sequences during replication, resulting in single-stranded loops of one or more unpaired bases called insertion/deletion loops (IDLs) that can be mutagenic [Sancar, A. (1999) *Nat. Genet.* 21:247–249]. The human genome has an abundance of simple repeat sequences that are relatively unstable [Petruska et al. (1998) *J. Biol. Chem.* 273(9):5204–5210]. Expansion of such repeat sequences have been associated with human genetic diseases including Huntington's disease, fragile X syndrome and myotonic dystrophy [Pearson et al. (1998) *Nucleic Acids Res.* 26(3):816–823].

The *Escherichia coli* Mut HLS pathway has been extensively characterized and is the prototypical DNA mismatch repair (MMR) pathway. This repair pathway recognizes and repairs small IDLs and all single base mismatches except C/C in a strand-specific manner [Modrich, P. (1991) *Annu. Rev. Genet.* 25:229–253]. Mismatch repair pathways have been highly conserved during evolution [Modrich and Lahaue (1996) *Annu. Rev. Biochem.* 65:101–133]. Eukaryotes including *Saccharomyces cerevisiae* and humans have several genes encoding proteins homologous to bacterial MutL and MutS [Sancar, A. (1999) supra]. For example, there are six MutS (Msh1–Msh6) and four MutL (MLH1–3, PMS1) homologs in *S. cerevisiae* [Kolodoner, R. (1996) *Genes Dev.* 10:1433–1442]. The Msh2p–Msh6p heterodimer binds base mismatches and small IDLs whereas the Msh2p–Msh3p heterodimer binds only small and large IDLs [Marsischky et al. (1996) *Genes Dev.* 10(4):407–420].

A considerable amount of evidence implicates mismatch repair in stabilizing repetitive DNA sequences [Marsischky et al. (1996) supra; Fujii et al. (1999) *J. Mol. Biol.* 289: 835–850; Strand et al. (1993) *Nature* 365:274–276].

Cellular exposure to ultraviolet radiation (UV) results in numerous detrimental effects including cell death, mutation and neoplastic transformation. Studies indicate that some of these deleterious effects are due to the formation of two major classes of bipyrimidine DNA photoproducts, cyclobutane pyrimidine dimers (CPDs) and (6-4) photoproducts (6-4 PPs). [Friedberg et al. (1995) In: DNA Repair and Mutagenesis, *Am. Soc. Microbiol.*, Washington, D.C., pp. 24–31].

Organisms have evolved several different pathways for removing CPDs and 6-4 PPs from cellular DNA [Friedberg et al. (1995) supra; Brash et al. (1991) supra]. These pathways include direct reversal and various excision repair pathways which can be highly specific or nonspecific for CPDs and 6-4 PPs. For example, DNA photolyases specific for either CPDs or 6-4 PPs have been found in a variety of species and restore the photoproduct bases back to their original undamaged states [Rubert, C. S. (1975) *Basic Life Sci.* 5A:73–87; Kim et al. (1994) *J. Biol. Chem.* 269: 8535–8540; Sancar, G. B. (1990) *Mutat. Res.* 236:147–160]. Excision repair has been traditionally divided into either base excision repair (BER) or nucleotide excision repair (NER) pathways, which are mediated by separate sets of proteins but which both are comprised of DNA incision, lesion removal, gap-filling and ligation reactions [Sancar, A. (1994) *Science* 266:1954–19560; Sancar and Tang (1993) *Photochem. Photobiol.* 57:905–921]. BER N-glycosylase/AP lyases specific for CPDs cleave the N-glycosidic bond of the CPD 5' pyrimidine and then cleave the phosphodiester backbone at the abasic site via a β-lyase mechanism, and have been found in several species including T4 phage-infected *Escherichia coli*, *Micrococcus luteus*, and *Saccharomyces cerevisiae* [Nakabeppu et al. (1982) *J. Biol. Chem.* 257:2556–2562; Grafstrom et al. (1982) *J. Biol. Chem.* 257:13465–13474; Hamilton et al. (1992) *Nature* 356:725–728]. NER is a widely distributed, lesion non-specific repair pathway which orchestrates DNA damage removal via a dual incision reaction upstream and downstream from the damage site, releasing an oligonucleotide containing the damage and subsequent gap filling and ligation reactions [Sancar and Tang (1993) supra].

Recently, an alternative excision repair pathway initiated by a direct acting nuclease which recognizes and cleaves DNA containing CPDs or 6-4 PPs immediately 5' to the photoproduct site has been described [Bowman et al. (1994) *Nucleic. Acids Res.* 22:3026–3032; Freyer et al. (1995) *Mol. Cell. Biol.* 15:4572–4577; Doetsch, P. W. (1995) *Trends Biochem. Sci.* 20:384–386; Davey et al. (1997) *Nucleic Acids Res.* 25:1002–1008; Yajima et al. (1995) *EMBO J.* 14:2393–2399; Yonemasu et al. (1997) *Nucleic Acids Res.* 25:1553–1558; Takao et al. (1996) *Nucleic Acids Res.* 24:1267–1271]. The initiating enzyme has been termed UV damage endonuclease (UVDE, now termed Uve1p). Homologs of UVDE have been found in *Schizosaccharomyces pombe, Neurospora crassa* and *Bacillus subtilis* [Yajima et al. (1995) supra; Yonemasu et al. (1997) supra; Takao et al. (1996) supra]. The Uve1p homologs from these three species have been cloned, sequenced and confer increased UV resistance when introduced into UV-sensitive strains of *E. coli, S. cerevisiae*, and human cells [Yajima et al. (1995) supra; Takao et al. (1996) supra]. In *S. pombe* Uve1p is encoded by the uve1+gene. However, because of the apparently unstable nature of partially purified full-length and some truncated UVDE derivatives, UVDE enzymes have been relatively poorly characterized and are of limited use [Takao et al. (1996) supra].

Because of the increasing and widespread incidence of skin cancers throughout the world and due to the reported inherent instability of various types of partially purified full-length and truncated UVDE derivatives, there is a long felt need for the isolation and purification of stable UVDE products, especially for use in skin care and medicinal formulations.

SUMMARY OF THE INVENTION

It is an object of the present invention to provide purified stable UVDE (Uve1p), polypeptide fragments which retain high levels of activity, particularly those from the *Schizosaccharomyces pombe* enzyme. In a specific embodiment, the polypeptide fragment is Δ228-UVDE, which contains a 228 amino-acid deletion of the N-terminal region of the *S. pombe* uve1+gene product; a second specific embodiment is the fusion protein GST-Δ228-UVDE. The DNA sequence encoding GST-full-length UVDE from *S. pombe* is given in SEQ ID NO:1. The deduced amino acid sequence of full-length UVDE is given in SEQ ID NO:2. The DNA sequence encoding Δ228-UVDE is given in SEQ ID NO:3. The deduced amino acid sequence of Δ228-UVDE is given in SEQ ID NO:4. The DNA coding sequence and deduced amino acid sequence for GST-Δ228-UVDE are given in SEQ ID NO:5 and SEQ ID NO: 6, respectively. Also encompassed within the present invention are truncated UVDE proteins wherein the truncation is from about position 100 to about position 250 with reference to SEQ ID NO:2, and wherein the truncated proteins are stable in substantially pure form.

Also within the scope of the present invention are nucleic acid molecules encoding such polypeptide fragments and recombinant cells, tissues and animals containing such nucleic acids or polypeptide fragments, antibodies to the polypeptide fragments, assays utilizing the polypeptide fragments, pharmaceutical and/or cosmetic preparations containing the polypeptide fragments and methods relating to all of the foregoing.

A specifically exemplified embodiment of the invention is an isolated, enriched, or purified nucleic acid molecule encoding Δ228-UVDE. Another exemplified embodiment is an isolated, enriched or purified nucleic acid molecule encoding GST-Δ228-UVDE.

In a specifically exemplified embodiment, the isolated nucleic acid comprises, consists essentially of, or consists of a nucleic acid sequence set forth in SEQ ID NO:3 or SEQ ID NO:5.

In another embodiment, the invention encompasses a recombinant cell containing a nucleic acid molecule encoding Δ228-UVDE or GST-Δ228-UVDE. The recombinant nucleic acid may contain a sequence set forth in SEQ ID NO:3 or SEQ ID NO:5, a synonymous coding sequence or a functional derivative of SEQ ID NO:3 or SEQ ID NO:5. In such cells, the Δ228-UVDE coding sequence is generally expressed under the control of heterologous regulatory elements including a heterologous promoter that is not normally coupled transcriptionally to the coding sequence for the UVDE polypeptide in its native state.

In yet another aspect, the invention relates to a nucleic acid vector comprising a nucleotide sequence encoding Δ228-UVDE or GST-Δ228-UVDE and transcription and translation control sequences effective to initiate transcription and subsequent protein synthesis in a host cell. Where a GST full length or truncated derivative is expressed, the GST portion is desirably removed (after affinity purification) by protease cleavage, for example using thrombin.

It is yet another aspect of the invention to provide a method for isolating, enriching or purifying the polypeptide termed Δ228-UVDE.

In yet another aspect, the invention features an antibody (e.g., a monoclonal or polyclonal antibody) having specific binding affinity to a UVDE polypeptide fragment. By "specific binding affinity" is meant that the antibody binds to UVDE polypeptides with greater affinity than it binds to other polypeptides under specified conditions.

Antibodies having specific binding affinity to a UVDE polypeptide fragment may be used in methods for detecting the presence and/or amount of a truncated UVDE polypeptide in a sample by contacting the sample with the antibody under conditions such that an immunocomplex forms and detecting the presence and/or amount of the antibody conjugated to the UVDE polypeptide. Kits for performing such methods may be constructed to include a first container having a conjugate of a binding partner of the antibody and a label, for example, a radioisotope or other means of detection as well known to the art.

Another embodiment of the invention features a hybridoma which produces an antibody having specific binding affinity to a UVDE polypeptide fragment. By "hybridoma" is meant an immortalized cell line which is capable of secreting an antibody, for example a Δ228-UVDE specific antibody. In preferred embodiments, the UVDE specific antibody comprises a sequence of amino acids that is able to specifically bind Δ228-UVDE. Alternatively, a GST-tag specific antibody or labeled ligand could be used to determine the presence of or quantitate a GST-Δ228-UVDE polypeptide, especially in formulations ex vivo.

The present invention further provides methods for cleaving DNA molecules at positions with structural distortions, wherein the DNA is cleaved in the vicinity of the distortion by a stable truncated UVDE protein of the present invention. The structural distortion can result from mismatch at the site of the distortion in a double-stranded DNA molecule, from UV damage or from other damage to DNA due to chemical reaction, for example, with an alkylating or depurination agent or due to damage due to UV irradiation, ionizing radiation or other irradiation damage. The stable truncated UVDE proteins can be supplied in substantially pure form for in vitro reactions or they can be supplied for in vivo reactions, including but not limited to compositions for topical application (in the form or of an ointment, salve, cream, lotion, liquid or transdermal patch) in pharmaceutical compositions for internal use (to be administered by intraperitoneal, intradermal, subcutaneous, intravenous or intramuscular injection). The stable truncated UVDE derivatives of the present invention repair a wide variety of mismatch and DNA damage. The cleavage of a double stranded DNA molecule having structural distortion due to nucleotide mispairing (mismatch) or due to DNA damage by a stable truncated UVDE derivative of the present invention can be used to advantage in a relatively simple assay for structural distortion wherein cleavage of a test molecule (i.e., the double stranded DNA molecule which is being screened for damage, mismatch or other structural distortion) is to be detected.

The present invention further provides a method for clearing a double stranded DNA molecule in which there is a structural distortion. The structural distortion can be due to aberrations including, but not limited to, base pair mismatch, photoproduct formation, alkylation of a nucleic acid molecule such that normal Watson-Crick base pairing is disturbed, intercalation between nucleotides of a compound which could be, for example, an acriflavine, an ethidium halide, among others, or a platinum adduct, for example of a cisplatin moiety. The distortion can also be an insertion-deletion loop of five or fewer nucleotides. Desirably, the loop has four or fewer nucleotides. The DNA can also contain an abasic site, a uracil residue resulting from deamenation of a cytosine residue, among others. The method of the present invention can be employed using the UVDE (Uve1p) protein from *Schizosaccharomyces pombe*, a truncated derivative of the *S. pombe* UVDE (lacking from about 100 to about 250 N-terminal amino acids), the Δ228-UVDE of *S pombe*, or the *Neurospora crassa, Bacillus subtilis, Homo sapiens* or *Deinococcus radiodurans* enzymes as set forth herein (see SEQ ID NOs:36–39). Additional homologs of the *S. pombe* UVDE include the UV damage enzyme of *Bacillus anthracis; Halobacterium* sp.; described in Genbank Accession No. AAC 82899; *Methanococcus jannaschii*; disclosed in Genbank Accession No. 057597; and *Thermotoga maritima*, disclosed in Genbank Accession No. AE001740. Specifically exemplified truncated UVDE (Δ228) is given in SEQ ID NO:4. DNA containing the structural distortion is contacted with an enzyme (or active truncated derivative) as described above under conditions allowing endonucleolytic cleavage of one strand of the distorted DNA molecule.

BRIEF DESCRIPTION OF THE DRAWINGS

FIG. 1A shows the purification of GST-Δ228-UVDE. Proteins were visualized on a silver-stained 12% SDS-polyacrylamide gel. Lanes M: protein molecular weight markers (sizes indicated on the right). Lane 1: 0.5 μg of soluble protein (column load) from crude extract of *S. cerevisiae* overexpressing cells. Lane 2: 0.5 μg of unbound protein from affinity column flow through. Lane 3: 1.0 μg of unbound protein from column wash fractions. Lanes 4–8: equal volume (20 μg) loads of column fractions from affinity column bound proteins eluted with glutathione corresponding to 5, 15, 65, 55, and 35 ng of total protein, respectively. FIG. 1B illustrates SDS-PAGE analysis (silver-stained 12% gel) of proteins following reapplication of GST-Δ228-UVDE onto glutathione-Sepharose and on-column thrombin cleavage to remove the GST tag. Lane M: protein molecular weight markers (sizes indicated on left). Lane 1: 100 ng of GST-Δ228-UVDE (column load). Lane 2: 250 ng thrombin reference marker. Lane 3: 250 ng of Δ228-UVDE eluted from column following thrombin cleavage. Lane 4: 400 ng (total protein) of GST-Δ228-UVDE and GST remaining bound to affinity column following thrombin cleavage and elution with glutathione. Arrows indicate the positions of GST-Δ228-UVDE (A, 68.7 kDa), Δ228-UVDE (B, 41.2 kDa), thrombin (C, 37 kDa), and GST (D, 27.5 kDa). FIG. 1C shows activities of GST-Δ228-UVDE and Δ228-UVDE preparations on CPD-30mer. CPD-30mer was incubated with the following preparations of UVDE: crude extract of overexpressing cell containing vector alone (lane 1), GST-Δ228-UVDE (lane 2), FL-UVDE (lane 3), affinity-purified GST alone (lane 4), affinity-purified GST-Δ228-UVDE (lane 5) and affinity-purified Δ228-UVDE (lane 6). Oligonucleotide cleavage products (14mer) corresponding to UVDE-mediated DNA strand scission of CPD-30mer immediately 5' to the CPD site were analyzed on DNA sequencing gels and subjected to autoradiography and phosphorimager analysis.

FIG. 5A is a plot of reaction rate (Rate) vs substrate concentration using the mean±standard deviation from three separate experiments. Curve shown is the best fit to the Michaelis-Menten equation of the averaged data. FIG. 5B is a Lineweaver-Burk plot of the kinetic data.

FIG. 6A: 5' end labeled cs-CPD-30mer duplex was incubated with buffer only (lane 1), an extract of cells over-expressing GΔ228-Uve1p (5 μg) (lane 2), affinity-purified GΔ228-Uve1p (lane 3) and affinity-purified Δ228-Uve1p (50 ng of each) (lane 4) and affinity-purified GST alone (2 μg) (lane 5). FIG. 6B: 3' end labeled cs-CPD-30mer duplex was incubated with the same Uve1p preparations. Order of lanes is the same as for FIG. 6A. Arrows a and b indicate the primary and secondary cleavage sites. The photoproduct (TAT corresponds to CPD) containing section of cs-CPD-30mer is shown at the bottom of the figure. For simplicity the complementary strand is not shown.

FIGS. 8A–8E show Uve1p activity on bipyrimidine UV induced photoproducts. To determine if Uve1p was capable of recognizing a broad spectrum of UV induced photoproducts, crude extracts from cells expressing GΔ228-Uve1p (lane 1) and G-Uve1p (lane 2) (5 μg of each), and affinity-purified Δ228-Uve1p (lane 3) and GΔ228-Uve1p (lane 4) (50 ng of each) were incubated with the following 5' end-labeled (*) duplex oligonucleotide substrates (FIG. 8A) cs-CPD-49mer, (FIG. 8B) 6-4PP-49mer, (FIG. 8C) tsI-CPD-49mer, (FIG. 8D) tsII-CPD-49mer, and (FIG. 8E) Dewar-49mer. The UV photoproduct (T^T) containing section of the sequence is shown at the bottom of the figure. Arrows a and b indicate the major and minor products formed by Uve1p mediated cleavage. Arrow uc indicates the uncleaved substrate. The sequence of the complementary strand is omitted.

FIG. 10A shows cleavage of an oligonucleotide substrate containing an AP site by Uve1p. To investigate if Uve1p was capable of cleaving an abasic site in a hydrolytic manner, we prepared a 5' end-labeled (*) abasic substrate, AP-37mer, and incubated this substrate with buffer alone (lane 1), E. coli endonuclease III (AP lyase, lane 2), affinity-purified GΔ228-Uve1p and Δ228-Uve1p (2 μg of each) (lanes 3 and 4), extracts of cells over-expressing GΔ228-Uve1p (5 μg) (lane 5), E. coli endonuclease IV (hydrolytic AP endonuclease, lane 6) and purified recombinant GST (2 μg) (lane 7). FIG. 10B demonstrates competitive inhibition of AP site recognition and cleavage. To demonstrate that the products generated are as a result of Uve1p-mediated cleavage at the AP site, AP-37mer was incubated with buffer alone (lane 1), E. coli endonuclease IV (lane 2), and affinity-purified GΔ228-Uve1p (2 μg) (lane 3) with 10X and 40X unlabeled cs-CPD-30mer (lanes 4 and 5, respectively) and 10X and 40X unlabeled UD-37mer (lanes 6 and 7, respectively). Arrows a and b indicate the primary and secondary Uve1p-mediated cleavage products, respectively. Arrow uc indicates the uncleaved substrate. A portion of the sequence of the AP substrate is shown at the bottom of the figure. S corresponds to deoxyribose and p corresponds to phosphate. The location of the cleavage sites of endonuclease III ($E_{III}$) and endonuclease IV ($E_{IV}$) are also indicated. For simplicity the complementary strand is omitted from the figure.

FIG. 11A: Analysis of 5' termini of Uve1p-generated DNA cleavage products with *CX/AY-31mer. 3' end labeled oligo with C/A mismatch (sequence on bottom) reacted with GΔ228-Uve1p and then further treated with PNK or CIP as indicated in the (+) and (−) lanes. Lane 1 is buffer treatment only. Arrows a and b indicate sites of Uve1p cleavage. FIG. 11B: Full length Uve1p possesses mismatch endonuclease activity. 5' end labeled duplex *CX/AY-31 mer was incubated with crude extracts of cells expressing either full-length, GST-tagged Uve1p (GFL-Uve1p) (lane 1), truncated Uve1p (GΔ228-Uve1p) (lane 2), cells expressing the GST tag alone (lane 3) or with E. coli endonuclease V, a known mismatch endonuclease (lane 4). Arrows indicate cleavage sites immediately (arrow a) and one nucleotide 5' to the mismatch site. Arrow V indicates E. coli endonuclease V cleavage 3' to the mismatch site and was used as a position reference. Bands below arrows (indicated by asterisks) correspond to shortened products due to a weak 5' to 3' exonuclease activity present in the Uve1p preparations.

FIG. 13A shows 3'-end-labeled *CX/AY-41mer incubated with restriction enzyme DdeI (lane 1), GΔ228-Uve1p (lane 2), or buffer (lane 3). The reaction products were analyzed on a nondenaturing gel as described below for the presence of DNA double-strand break products (arrow dsb). Arrows b and c indicate the primary cleavage site for Uve1p on this substrate. FIG. 13B shows 3'-end-labeled *CX/AY-41mer or CX/*AY-41mer incubated with GΔ228-Uve1p (+lanes) or buffer (−lanes) and analyzed on denaturing DNA sequencing-type gels. Arrows b and c indicate positions of major Uve1p cleavage events relative to the mismatched base (asterisk) position. G+A and C+T base-specific sequencing ladders are included in outside lanes as nucleotide position markers.

FIGS. 14A–14C show that Uve1 p recognizes small IDLs but not large IDLs or hairpin structures. Cleavage reactions were carried out with 3'-end-labeled DNA duplexes under standard reaction conditions and products were analyzed on DNA sequencing gels as described in the text. Arrows (a, b and c) indicate GΔ228-Uve1-mediated DNA cleavage products. G and C+T base-specific chemical cleavage DNA sequencing ladders were run in adjacent lanes as nucleotide position markers. The 3' end labeled (*) core substrate sequence is shown at the bottom of the figure with Uve1p cleavage sites a, b and c indicated (X corresponds to IDL sequences shown in FIG. 14A. FIG. 14 A: 3'-end labeled duplexes ID0, ID2 and ID4; FIG. 14B: ID0 and HP8; (C) ID4, ID6 and ID8 were treated with GΔ228-Uve1p (even numbered (+) lanes) or buffer (odd numbered (−) lanes).

(FIG. 17C) Substrates AB, AC, AE and AD were 3'-end labeled and incubated with GΔ228-Uve1p under standard conditions as described below. The percent cleavage was quantified by phosphorimager analysis. The error bars indicate the mean±standard deviation obtained from three separate experiments.

DETAILED DESCRIPTION OF THE INVENTION

Figure 1A:
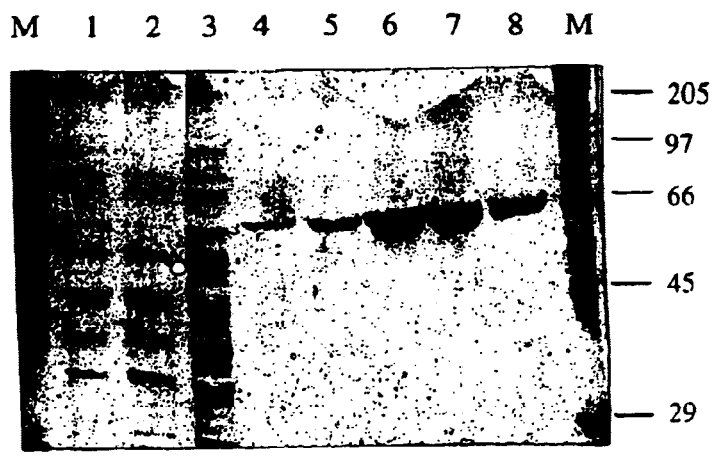
FIGS. 1A–1C show purification and activity of GST-Δ228-UVDE and Δ228-UVDE. GST-Δ228-UVDE and Δ228-UVDE from overexpressing *S. cerevisiae* DY150 cells were purified by affinity chromatography on glutathione-Sepharose columns.

Abbreviations used in the present specification include the following: aa, amino acid(s); AER, alternative excision repair; bp, base pair(s); BER, base excision repair; cDNA, DNA complementary to RNA; CPD, cyclobutane pyrimidine dimer; FL, full-length; GΔ228Uve1p, GST-tagged truncated Uve1p; GST, glutathione-S-transferase; IDL, insertion deletion loop; NER, nucleotide excision repair; nt, nucleotide; PAGE, polyacrylamide gel electrophoresis; PMSF, phenylmethanesulfonyl fluoride, 6-4 PP, (6-4) photoproduct; UVDE or Uve1p, used interchangeably, ultraviolet damage endonuclease; Δ228-UVDE, UVDE truncation product lacking 228 N-terminal amino acids.

By "isolated" in reference to a nucleic acid molecule it is meant a polymer of 14, 17, 21 or more nucleotides covalently linked to each other, including DNA or RNA that is isolated from a natural source or that is chemically synthesized. The isolated nucleic acid molecule of the present invention does not occur in nature. Use of the term "isolated" indicates that a naturally occurring or other nucleic acid molecule has been removed from its normal cellular environment. By the term "purified" in reference to a nucleic acid molecule, absolute purity is not required. Rather, purified indicates that the nucleic acid is more pure than in the natural environment.

A "nucleic acid vector" refers to a single or double stranded circular nucleic acid molecule that can be transfected or transformed into cells and replicate independently or within the host cell genome. A circular double stranded nucleic acid molecule can be linearized by treatment with the appropriate restriction enzymes based on the nucleotide sequences contained in the cloning vector. A nucleic acid molecule of the invention can be inserted into a vector by cutting the vector with restriction enzymes and ligating the two pieces together. The nucleic acid molecule can be RNA or DNA.

Many techniques are available to those skilled in the art to facilitate transformation or transfection of the recombinant construct into a prokaryotic or eukaryotic organism. The terms "transformation" and "transfection" refer to methods of inserting an expression construct into a cellular organism. These methods involve a variety of techniques, such as treating the cells with high concentrations of salt, an electric field, or detergent, to render the host cell competent for uptake of the nucleic acid molecules of interest or liposome-mediated transfection can be employed.

The term "promoter element" describes a nucleotide sequence that is incorporated into a vector which enables transcription, in appropriate cells, of portions of the vector DNA into mRNA. The promoter element precedes the 5' end of the Δ228-UVDE or GST-Δ228-UVDE nucleic acid molecule such that the Δ228-UVDE OR GST-Δ228-UVDE sequence is transcribed into mRNA. Transcription enhancing sequences may also be incorporated in the region upstream of the promoter. mRNA molecules are translated to produce the desired protein(s) within the recombinant cells.

Those skilled in the art would recognize that a nucleic acid vector can contain many other nucleic acid elements besides the promoter element and the Δ228-UVDE or GST-Δ228-UVDE nucleic acid molecule. These other nucleic acid elements include, but are not limited to, origins of replication, ribosomal binding sites, transcription and translation stop signals, nucleic acid sequences encoding drug resistance enzymes or amino acid metabolic enzymes, and nucleic acid sequences encoding secretion signals, periplasm or other localization signals, or signals useful for polypeptide purification.

As used herein, "Δ228-UVDE polypeptide" has an amino acid sequence as given in or substantially similar to the sequence shown in SEQ ID NO:4. A sequence that is substantially similar will preferably have at least 85% identity and most preferably 99–100% identity to the sequence shown in SEQ ID NO:4. Those skilled in the art understand that several readily available computer programs can be used to determine sequence identity with gaps introduced to optimize alignment of sequences being treated as mismatched amino acids and where the sequence in SEQ ID NO:4 is used as the reference sequence.

As used herein, "GST-Δ228-UVDE polypeptide (GΔ228Uve1p) has an amino acid sequence as given in or substantially similar to the sequence shown in SEQ ID NO:6. A sequence that is substantially similar will preferably have at least 85% identity and most preferably 99–100% identity to the sequence shown in SEQ ID NO:6. Those skilled in the art understand that several readily available computer programs can be used to determine sequence identity with gaps introduced to optimize alignment of sequences being treated as mismatched amino acids and where the sequence in SEQ ID NO:6 is used as the reference sequence.

By "isolated" in reference to a polypeptide is meant a polymer of 6, 12, 18 or more amino acids conjugated to each other, including polypeptides that are isolated from a natural source or that are chemically synthesized. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (at least about 90–95% pure) of material naturally associated with it.

The term "purified" in reference to a polypeptide does not require absolute purity (such as a homogeneous preparation); instead, it represents an indication that the polypeptide is relatively purer than in the natural environment. Purification of at least two orders of magnitude, preferably three orders of magnitude, and more preferably four or five orders of magnitude is expressly contemplated, with respect to proteins and other cellular components present in a truncated UVDE-containing composition. The substance is preferably free of contamination at a functionally significant level, for example 90%, 95%, or 99% pure. Based on increases in calculated specific activity, GST-Δ228-UVDE and Δ228-UVDE have been purified 230-fold and 310-fold, respectively. However, based on silver-stained SDS polyacrylamide gel results, it appears that both proteins have been purified nearly to homogeneity (see FIG. 1).

As used herein, a "UVDE polypeptide fragment" or "truncated UVDE" has an amino acid sequence that is less than the full-length amino acid sequence shown in SEQ ID NO:2. Also as used herein, UVDE and Uvelp are used synonymously.

In the present context, a "UVDE mutant polypeptide" is a UVDE polypeptide or truncated UVDE which differs from the native or truncated native sequence in that one or more amino acids have been changed, added or deleted. Changes in amino acids may be conservative or non-conservative. By conservative it is meant the substitution of an amino acid for one with similar properties such as charge, hydrophobicity and structure. A UVDE mutant polypeptide of the present invention retains its useful function, i.e., for example, ability to remove cyclobutane pyrimidine dimers and/or (6-4) photoproducts from DNA, and its enzymatic activity is stable in its substantially purified form. The full-length UVDE protein and the truncated derivatives of the present invention recognize a wide variety of DNA damage and distortions to double stranded DNA, as described hereinbelow. The UVDE and truncated UVDE proteins are useful in cleaving double-stranded DNA molecules in which damage including but not limited to abasic sites, photoproducts, cis-platin adducts and a variety of other aberrations also including mismatched base pairing and sites adjacent to and at locations of intercalations (for example with acridine dyes or ethidium bromide, among others, and these proteins, particularly the stable truncated derivatives of the present invention are useful in vivo and/or in vitro for repairing DNA distortions as described herein.

The isolation of genes encoding UVDEs from different organisms has been described previously [Yajima et al. (1995) supra; Takao et al. (1996) supra]. These genes have been cloned by introducing a foreign cDNA library into a repair-deficient E. coli strain and selecting for complemented cells by UV irradiation of the transformants. [Yajima et al. (1995) supra; Takao et al. (1996) supra]. Researchers have not characterized full-length UVDEs because they become unstable and lose their activity when purified [Takao et al. (1996) supra]. This instability makes their use as therapeutic agents problematical.

Because UVDEs can be used for a variety of applications including the treatment and prevention of diseases caused by DNA damage, the inventors sought to discover stable UVDEs. The present inventors have noted that the activity of the full-length UVDE appears relatively stable to storage and freeze-thawing when it is present in crude extracts of either its native Schizosaccharomyces pombe or recombinant Escherichia coli [see also Takao et al. (1996) supra]. The present inventors and others have not had success in obtaining enzymatically active purified UVDE in good yield. The present invention describes the isolation and purification of a polypeptide fragment from S. pombe which exhibits superior stability and enzymatic activity than purified full-length UVDE.

The full-length uvde gene from S. pombe was amplified from a cDNA library by the polymerase chain reaction (PCR) using methods known to those skilled in the art and as described herein. Δ228-UVDE, which contains a deletion of the of the first 228 N-terminal amino acids of full-length UVDE, was prepared using PCR as described herein.

The amplified UVDE gene coding fragments were cloned into the yeast expression vector pYEX4T-1. In pYEX 4T-1, the UVDE-derived polypeptides are expressed in frame with a glutathione-S-transferase (GST) leader sequence to generate a fusion protein of GST linked to the N-terminus of UVDE. The DNA sequence of the GST leader is shown in SEQ ID NO:7. The deduced amino acid sequence of the GST leader is shown in SEQ ID NO:8. Appropriate plasmids containing the DNA fragments in the proper orientation were transformed into S. cerevisiae, DY150 cells using the alkali cation method [Ito et al. (1993) J. Bacteriol. 153: 163–163]. Positive clones were selected and used for protein purification.

Both full-length UVDE and Δ228-UVDE were isolated and purified using glutathione-Sepharose affinity chromatography. Extracts from cells expressing GST-Δ228-UVDE were passed through glutathione-Sepharose columns. GST-Δ228-UVDE which bound to the column was eluted using glutathione. Additionally, Δ228-UVDE was generated by removal of the GST-leader from GST-Δ228-UVDE by treating GST-Δ228-UVDE, which had bound to the glutathione-Sepharose column, with thrombin. Pooled fractions from the affinity purification yielded approximately 1.5 mg of near-homogeneous or homogeneous GST-Δ228-UVDE protein per 500 mL of S. cerevisiae cells.

Figure 1B:
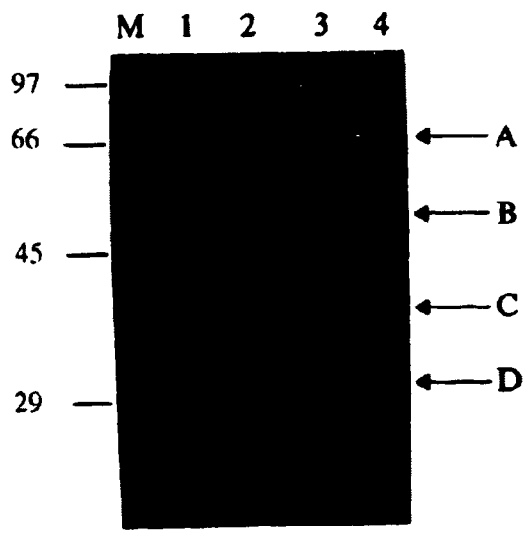
Figure 1C:
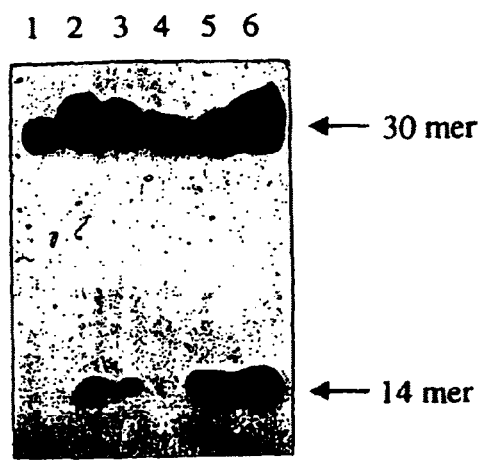

GST-Δ228-UVDE and Δ228-UVDE have electrophoretic mobilities corresponding to protein sizes, as determined by SDS-PAGE, of 68.7 kDa and 41.2 kDa, respectively (FIG. 1A, lanes 4–8; FIG. 1B, lane 3). Both crude and purified preparations of Δ228-UVDE and GST-66 228-UVDE retained enzymatic activity on an oligodeoxynucleotide substrate (CPD-30mer) containing a single cis-syn cyclobutane pyrimidine dimer embedded near the center of the sequence (FIG. 1C). In contrast, purified full-length UVDE resulted in a preparation that was not stable in that enzymatic activity was rapidly lost (FIG. 1C, lane 3). Furthermore, purified GST-Δ228-UVDE and Δ228-UVDE are stable when stored at −80° C. in 10% glycerol for a period of at least six months with no substantial loss of activity. Preparations of GST-Δ228-UVDE and Δ228-UVDE are resistant to several rounds of freeze-thawing. Surprisingly, both purified GST-Δ228-UVDE and Δ228-UVDE are more stable and have higher enzymatic activity than purified full-length UVDE.

Figure 2:
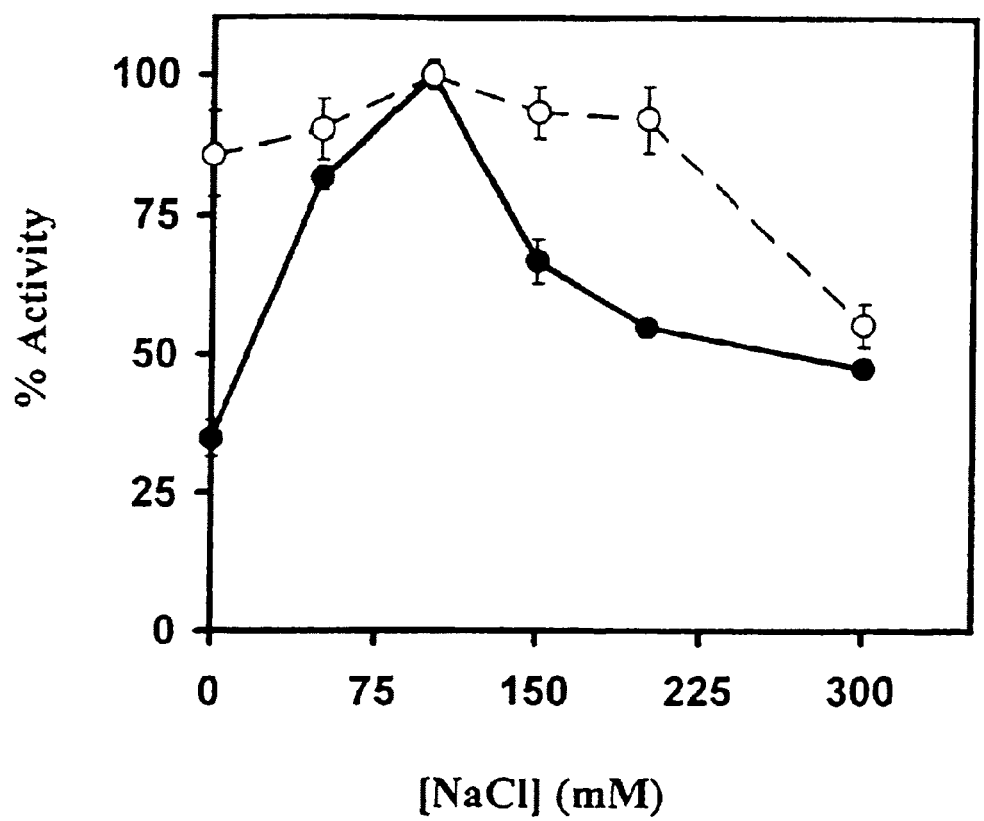
FIG. 2 shows the effect of salt concentration on UVDE activity. DNA strand scission assays on end-labeled CPD-30mer were carried out with 150 ng of affinity-purified GST-Δ228-UVDE (open circles) or 40 ng of affinity-purified Δ228-UVDE (closed circles) at pH 7.5 and various concentrations of NaCl under otherwise standard reaction conditions for 20 min (See Examples hereinbelow). Extent of DNA strand scission was determined from phosphorimager analysis of gels. Enzyme activity is expressed as a percentage of CPD-30mer cleaved relative to that observed at 100 mM NaCl (defined as 100%).
Figure 3:
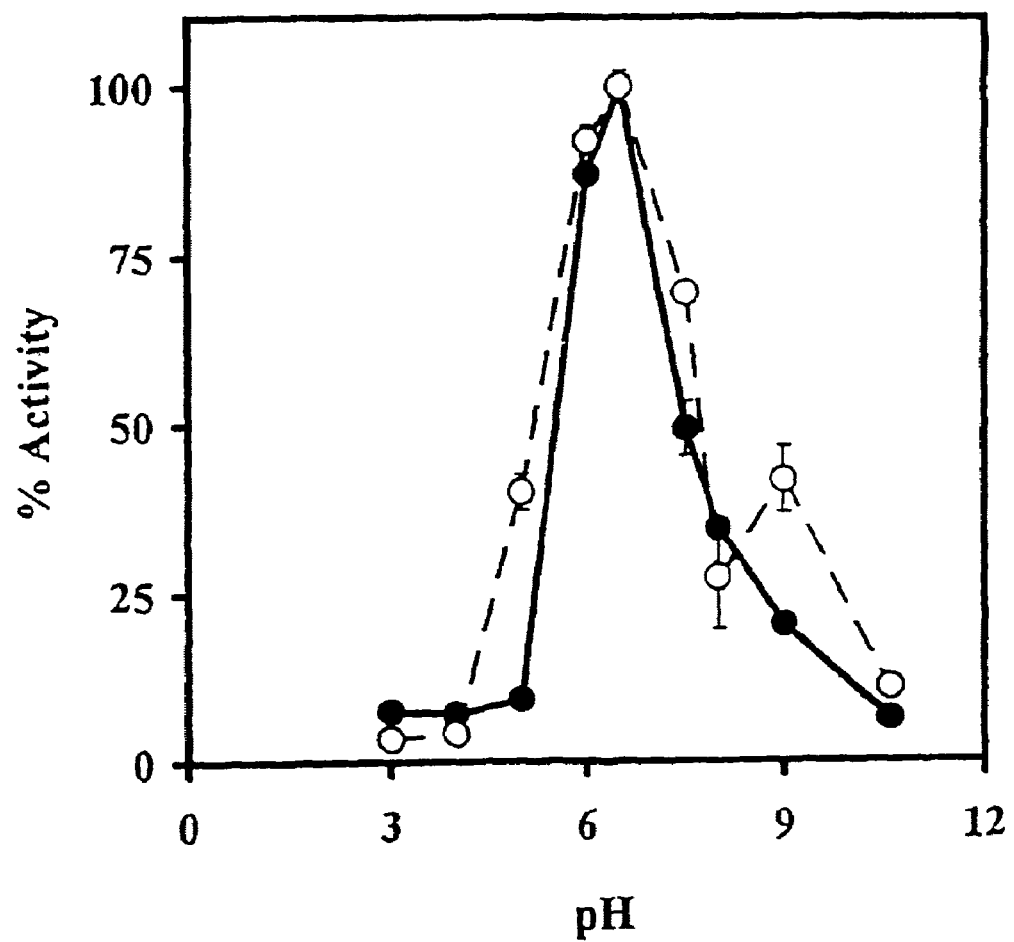
FIG. 3 illustrates the effect of pH on UVDE activity. DNA strand scission assays on end-labeled CPD-30mer were carried out with 150 ng of affinity-purified GST-Δ228-UVDE (open circles) or 40 ng of affinity-purified Δ228-UVDE (closed circles) under various pH conditions at otherwise standard reaction conditions for 20 minutes (as described herein). Extent of DNA strand scission was determined from phosphorimager analysis of gels and enzyme activity is expressed as a percentage of CPD-30mer cleaved relative to that observed at pH 6.5 (defined as 100%).

Both truncated forms of UVDE (GST-Δ228-UVDE and Δ228-UVDE) retained high levels of activity over a broad NaCl concentration range (50–300 mM) with an optimum around 100 mM (FIG. 2). Optimal cleavage of an oligodeoxynucleotide substrate (CPD-30mer) occurred in the presence of 10 mM $MgCl_2$ and 1 mM $MnCl_2$. Both GST-Δ228-UVDE and Δ228-UVDE showed optimal cleavage of CPD-30mer at pH 6.0–6.5 with activity sharply declining on either side of this range indicating that the GST tag does not affect the folding and activity of the protein (FIG. 3). The calculated pI values for GST-Δ228-UVDE and Δ228-UVDE are 6.8 and 7.5, respectively.

Figure 4:
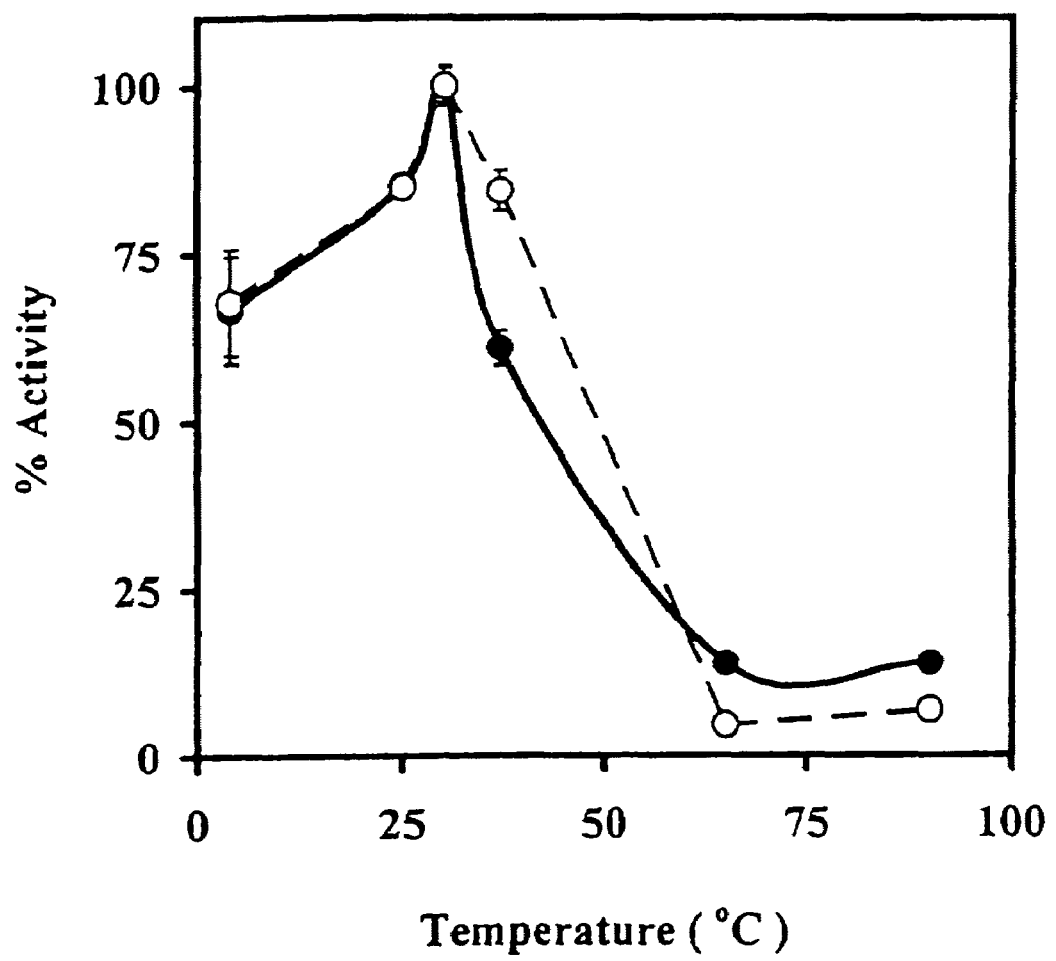
FIG. 4 shows the temperature dependence of UVDE activity. DNA strand scission assays on end-labeled CPD-30mer were carried out with 150 ng of affinity-purified GST-Δ228-UVDE (open circles) or 40 ng of affinity-purified Δ228-UVDE (closed circles) at the indicated temperatures under otherwise standard reaction conditions (See the Examples herein below) for 20 minutes. Extent of DNA strand scission was determined from phosphorimager analysis of gels and enzyme activity is expressed as a percentage of CPD-30mer cleaved relative to that observed at 30° C. (defined as 100%).

Under optimal pH, salt and divalent cation conditions, GST-Δ228-UVDE and Δ228-UVDE were found to exhibit a temperature optimum at 30° C. (FIG. 4). At 37° C. GST-Δ228 -UVDE and Δ228-UVDE activities decreased to approximately 85% and 60%, respectively and at 65° C., both truncated versions of UVDE showed a significant decrease in activity.

Figure 5A:
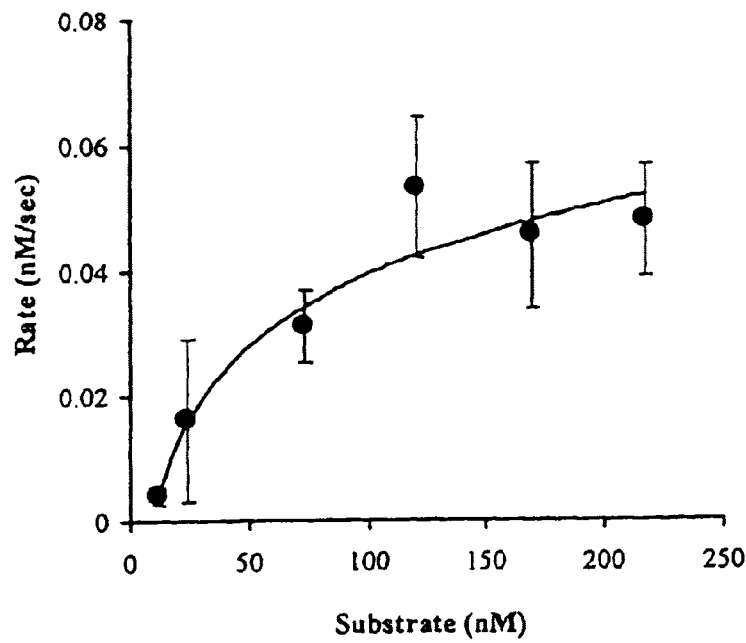
FIGS. 5A–5B illustrates kinetic analysis of CPD-30mer cleavage by purified Δ228-UVDE. Δ228-UVDE (5 nM) was reacted with increasing amounts of 5'-end-labeled CPD-30mer and analyzed for DNA strand scission as described in the Examples.
Figure 5B:
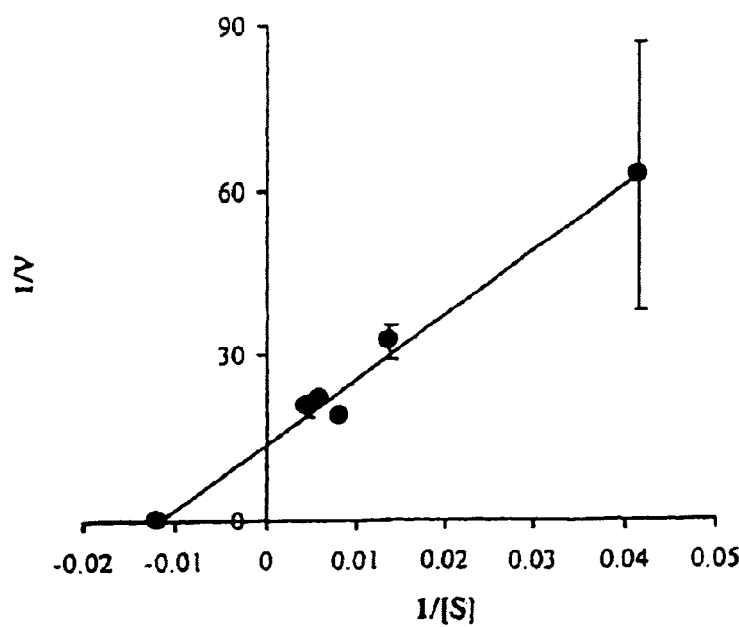

The kinetic parameters for homogeneous GST-Δ228-UVDE and Δ228-UVDE were determined using the CPD-30mer substrate. FIG. 5 shows that Michaelis-Menten kinetics apply to the CPD-30mer cleavage reactions with Δ228-UVDE. FIG. 5B is a Lineweaver-Burk plot of the kinetic data in FIG. 5A. The apparent $K_m$ for CPD-30mer was calculated to be 49.1 nM±7.9 nM for GST-Δ228-UVDE and 74.9 nM±3.6 nM for Δ228-UVDE. The $V_{max}$ values (nM $min^{-1}$) were found to be 2.4±0.13 and 3.9±0.12 for GST-Δ228-UVDE and Δ228-UVDE, respectively. The turnover numbers ($K_{cat}$) were 0.21±0.01 $min^{-1}$ for GST-Δ228-UVDE and 0.9±0.03 $min^{-1}$ for Δ228-UVDE.

Uve1p has been shown to be capable of recognizing both cis-syn CPDs (cs-CPD) and 6-4PPs [Bowman et al. (1994) Nucl. Acids Res. 22:3036–3032; Yajima et al. (1995) EMBO J. 14:2393–2399]. It is unique in this respect as no other single polypeptide endonuclease is known to recognize both of these UV photoproducts. CPDs and 6-4PPs are the most frequently occurring forms of UV-induced damage, but there are significant differences in the structural distortions induced in DNA by these two lesions. Incorporation of a cs-CPD into duplex DNA causes no significant bending or unwinding of the DNA helix [Rao et al. (1984) Nucl. Acids Res. 11:4789–4807; Wang et al. (1991) Proc. Natl. Acad. Sci. USA 88:9072–9076; Miaskiewicz et al. (1996) J. Am. Chem. Soc. 118:9156–9163; Jing et al. (1998) supra; McAteer et al. (1998) J. Mol. Biol. 282:1013–1032; Kim et al. (1995) supra] and destabilizes the duplex by ~1.5 kcal/mol [Jing et al. (1998) Nucl. Acids Res. 26:3845–3853]. It has been demonstrated that this relatively small structural distortion allows CPD bases to retain most of their ability to form Watson-Crick hydrogen bonds [Jing et al. (1998) supra; Kim et al. (1995) Photochem. Photobiol. 62:44–50]. On the other hand, NMR studies have suggested that 6-4PPs bend the DNA to a greater extent than cs-CPDs, and there is a destablization of ~6 kcal/mol in the DNA duplex with a resulting loss of hydrogen bond formation at the 3'-side of the 6-4PP DNA adduct [Kim et al. (1995) Eur. J. Biochem. 228:849–854]. The ability of Uve1p to recognize such different structural distortions suggests that it might also recognize other types of DNA damage.

CPDs can occur in DNA in four different isoforms (cis-syn I [cs I], cis-syn II [cs II], trans-syn I [ts I] and trans-syn II [ts II]) [Khattak and Wang (1972) Tetrahedron 28:945–957]. Pyrimidine dimers exist predominately in the cs I form in duplex DNA whereas trans-syn (ts) dimers are found primarily in single stranded regions of DNA. 6-4PPs are alkali labile lesions at positions of cytosine (and much less frequently thymine) located 3' to pyrimidine nucleosides [Lippke et al. (1981) Proc. Natl. Acad. Sci. USA 78:3388–3392]. 6-4PPs are not stable in sunlight and are converted to their Dewar valence isomers upon exposure to 313 nm light. We have investigated the specificity of Δ228-Uve1p for a series of UV photoproducts: cs-CPD, ts I-CPD, ts II-CPD, 6-4PP and the Dewar isomer. We also investigated the possibility that Uve1p may recognize other types of non-UV photoproduct DNA damage. We describe the activity of Uve1p on DNA oligonucleotide substrates containing a variety of lesions including a platinum-DNA GG diadduct (Pt-GG), uracil (U), dihydrouracil (DHU), 8-oxoguanine (8-oxoG), abasic sites (AP site), inosine (I), and xanthine (Xn). This collection of substrates contains base lesions that induce a broad range of different DNA structural distortions.

Figure 6A:
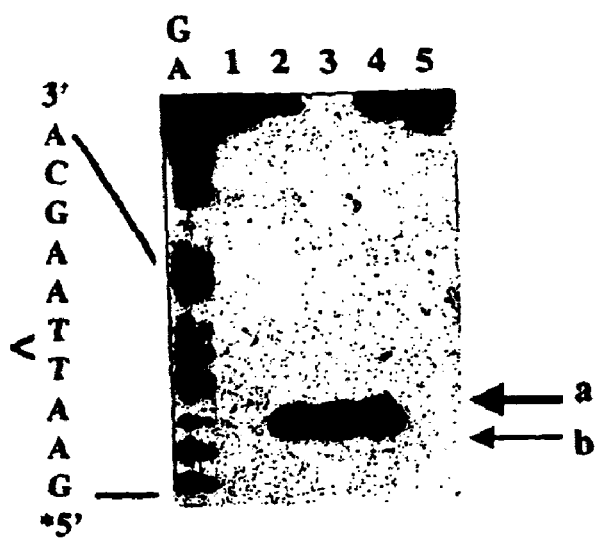
FIGS. 6A–6B show sites of Uve1p cleavage of CPD containing substrates. Various Uve1p preparations were incubated with 5' or 3' end-labeled (*) cs-CPD-30mer. Cleavage products corresponding to Uve1p-mediated strand scission of cs-CPD-30mer were visualized on a DNA sequencing-type gel.
Figure 6B:
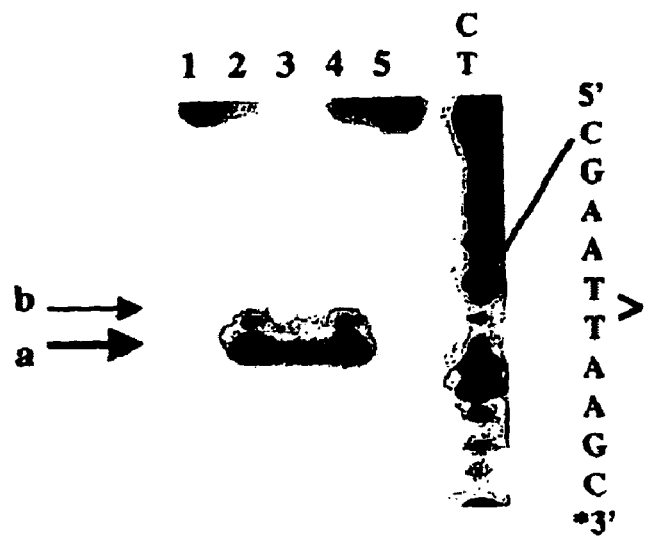
Figure 7A:
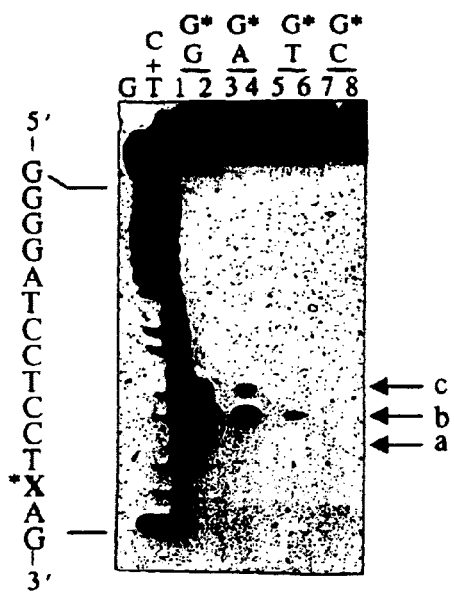
FIGS. 7A–7D demonstrate that GΔ228-Uve1p recognizes 12 different base mismatch combinations. The 3' end labeled oligo series X/Y-31mer (sequence given at bottom, asterisk indicates labeled strand and labeled terminus) was utilized to assess Uve1p cleavage activity on 16 different base pair and base mispair combinations (Table 1 B). Base mispairs indicated above numbered lanes with asterisks denoting base on the labeled strand for G-series (FIG. 7A), A-series (FIG. 7B), C-series (FIG. 7C) and T-series (FIG. 7D) treated with purified GΔ228-Uve1p (odd lanes) or mock reactions (even lanes). Reaction products were analyzed on DNA sequencing-type gels. Arrows indicate Uve1p cleavage sites immediately (arrow a), one (arrow b), and two (arrow c) nucleotides 5' to the mismatch site. G and C+T base-specific chemical cleavage DNA sequencing ladders were run in adjacent lanes as nucleotide position markers.
Figure 7B:
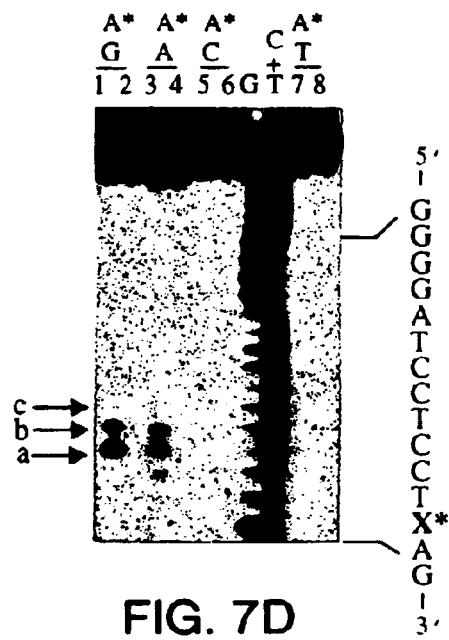
Figure 7C:
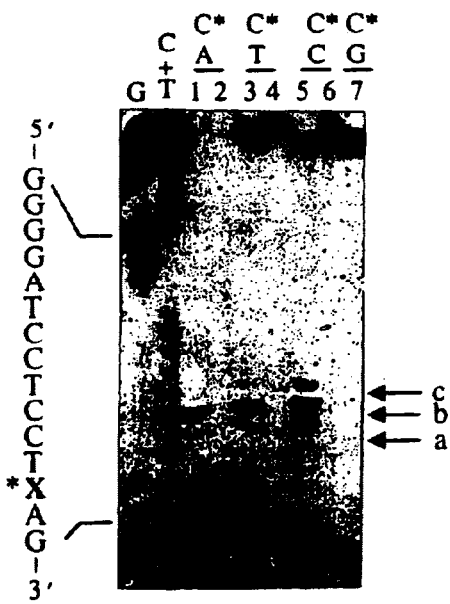
Figure 7D:
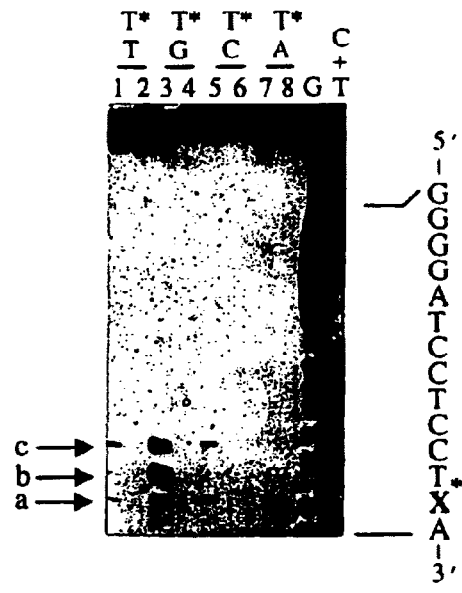

Uve1p isolated from S. pombe was first described as catalyzing a single ATP-independent incision event immediately 5' to the UV photoproduct, and generating termini containing 3' hydroxyl and 5' phosphoryl groups (Bowman et al. [1994] Nucl. Acids Res. 22:3026–3032). The purified GΔ228-Uve1p, Δ228-Uve1p and crude cell lysates of recombinant G-Uve1p and GΔ228-Uve1p make an incision directly 5' to CPDs similar to that observed with the native protein. In this study, we have used both 5' and 3' end-labeled duplex CPD-30mer (cs-CPD-30mer) to demonstrate the ability of Uve1p to cleave a CPD-containing substrate at two sites (FIGS. 6A–6B). The primary product (arrow a) accounted for approximately 90% of the total product formed and resulted from cleavage immediately 5' to the damage. The second incision site was located one nucleotide upstream and yielded a cleavage product (arrow b), which represented the remaining 10% of the product formed. This minor product is one nucleotide shorter or longer than the primary product depending on whether 5' or 3' end-labeled substrate is being examined. The same cleavage pattern was observed for each different Uve1p preparation used: i.e., crude extracts of cells expressing GΔ228-Uve1p, affinity-purified GΔ228-Uve1p and Δ228-Uve1p (FIGS. 2A and 2B, lanes 2, 3 and 4 respectively), as well as extracts of cells expressing GST-Uve1p. No cleavage products were observed when the cs-CPD-30mer substrates were incubated with buffer only, or purified recombinant GST prepared and affinity-purified in an identical manner to the purified Uve1p proteins (FIG. 6A, 6B, lanes 1 and 5 respectively). This control eliminates the possibility that these DNA strand scission products are formed as a result of the presence of trace amounts of non-specific endonuclease contamination. Uve1p recognizes a duplex cs-CPD-containing oligonucleotide substrate and cleaves this substrate at two sites. The primary site, responsible for 90% of the product, is immediately 5' to the damage and the secondary site (accounting for the remaining 10% of product), is one nucleotide 5' to the site of damage.

Uve1p cleaves both CPDs and 6-4PPs when they are incorporated into oligonucleotide substrates [Bowman et al. (1994) supra; Yajima et al. (1995) EMBO J. 14:2393–2399]. These lesions induce substantially different distortions in duplex DNA. The ability of native Uve1p to recognize both of these damages prompted us to investigate whether this endonuclease recognized other forms of UV-induced photodamage, as well. In order to determine the substrate range of recombinant Δ228-Uve1p for UV-induced bipyrimidine photoproducts, various Uve1p preparations were incubated with synthetic 49-mer oligonucleotides containing different forms of UV damage (Table 1A). The substrates used in these experiments were 5' end labeled duplex cs-CPD- 49mer, tsI-CPD-49mer, tsII-CPD-49mer, 6-4PP-49mer and Dewar-49mer (FIG. 8A). Generally, purified GΔ228-Uve1p and Δ228-Uve1p cleaved all of the bipyrimidine photoproduct substrates in a similar manner with respect to both the site and extent of cleavage. The cleavage pattern observed when crude cell lysates of G-Uve1p and GΔ228-Uve1p were incubated with the substrates was less consistent. Very low levels of product were observed when these extracts were incubated with the Dewar isomer. No cleavage products were detected when the damaged substrates were incubated with buffer alone or purified recombinant GST, demonstrating that no other DNA repair proteins were responsible for the cleavage of the substrate. In addition, incubation of Uve1p with end-labeled undamaged substrate (UD-30mer) did not result in the formation of any cleavage products. We concluded that Uve1p recognizes and cleaves these five UV-induced bipyrimidine photoproducts in a similar manner and that they are substrates for this enzyme. This is the first time that a single protein endonuclease capable of recognizing such a surprisingly broad range of UV-induced photoproducts has been described.

Figure 9:
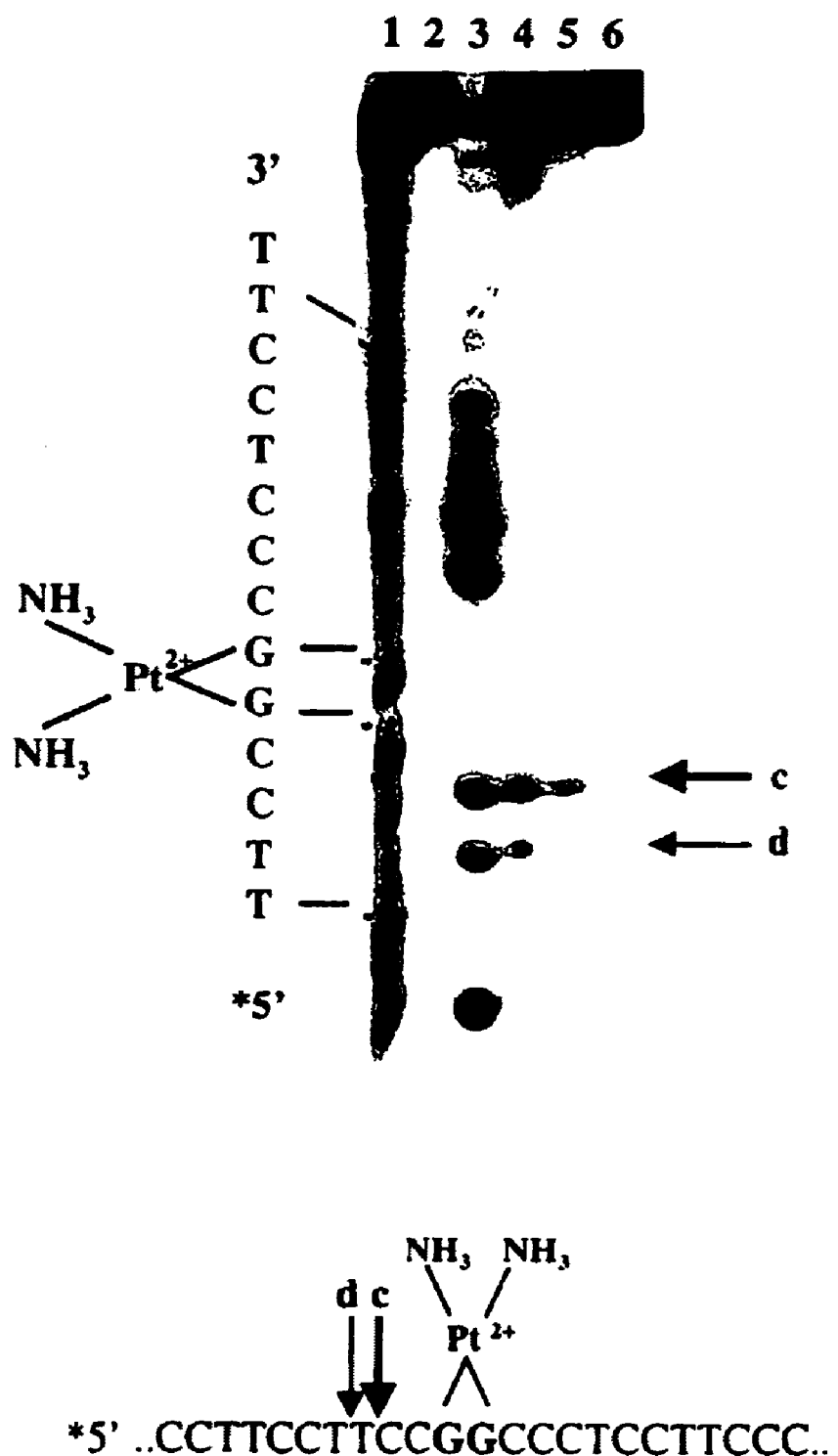
FIG. 9 shows Uve1 p activity on a platinum-DNA GG diadduct-containing substrate. Affinity-purified GΔ228-Uve1p (lane 4) and Δ228-Uve1p (1–2 μg) (lane 5) were incubated with 5' end-labeled duplex (*) Pt-Gg-32mer. This substrate was also incubated with buffer alone (lane 2), E. coli exonuclease III (150 units (Promega)) (lane 3) and affinity-purified GST (2 μg) (lane 6). Maxam and Gilbert sequencing (lane 1) of the oligonucleotide was carried out to identify the site of cleavage. Arrows c and d indicate the major and minor cleavage sites, respectively. The platinum-DNA GG diadduct containing section of the substrate is shown at the bottom of the figure. The sequence of the complementary strand is omitted.

To explore activity on DNA with non-UV-photoproduct diadducts we investigated whether Uve1p recognized an oligonucleotide containing a platinum-DNA lesion. cis-Diamminedichloroplatinum(II) (cisplatin) is a widely used antitumor drug that induces several types of mono- and diadducts in DNA. One of the major, biologically relevant adducts formed results from the coordination of N-7 of two adjacent guanines to platinum to form the intrastrand crosslink cis-[Pt(NH$_3$)$_2${d(GpG)-N7(1),-N7(2)}] (cis-PT-GG) (FIG. 9). A 5' end-labeled duplex 32-mer oligonucleotide with a single platinum intrastrand crosslink between positions 16 and 17 (Pt-GG-32mer) (Table 1A) was incubated with either GΔ228-Uve1p or Δ228-Uve1p, and the reaction products were visualized on a DNA sequencing-type gel (FIG. 9). The 3' to 5' exonuclease activity of E. coli exonuclease III was used to identify the specific site of cleavage of Uve1p, as a platinum-DNA diadduct will terminate or stall the digestion of the duplex DNA at this site [Royer-Pokora et al. (1981) Nucl. Acids Res. 9:4595–4609; Tullius and Lippard (1981) J. Am. Chem. Soc. 103:4620–4622]. Incubation of 5' end-labeled Pt-GG-32mer with exonuclease III (FIG. 9, lane 3) generates 5' end-labeled oligonucleotide fragments with 3' hydroxyl termini. Maxam and Gilbert sequencing (FIG. 9, lane 1) of the same substrate generates 5' end labeled fragments with 3' phosphoryl termini which consequently migrate faster than the exonuclease III product on DNA sequencing-type gels. (Due to overreaction with hydrazine all of the nucleotides are highlighted in the sequencing lane.) GΔ228-Uve1p cleaved Pt-GG-32mer 5' to the GpG adduct position at two adjacent sites (FIG. 9, lane 4, arrows c and d). The products c) and d) migrate with the exonuclease III products, confirming that they have 3' hydroxyl termini. Comparison with the Maxam and Gilbert sequencing ladder (FIG. 9, lane 1) indicates that the GΔ228-Uve1p-mediated cleavage products are generated by cleavage at sites located two and three nucleotides 5' to the platinum DNA-GG diadduct. The GΔ228-Uve1p-mediated cleavage products were quantified by phosphorimager analysis, and it was determined that cleavage at the primary site c (arrow c) accounted for approximately 90% of the total product formed while cleavage at the secondary site (arrow d) accounted for the remaining 10%. In contrast, Δ228-Uve1p appeared to cleave Pt-GG-32mer only at the primary site c (i.e., two nucleotides 5' to the damage) (FIG. 9, lane 5). When the quantity of protein used and the total amount of product formed is taken into account, the cleavage of Pt-GG-32mer by Uve1p appears at least 100-fold less efficient than the cleavage of the UV-induced photoproducts. Despite this significant decrease in efficiency, Pt-GG-32mer is a substrate for Uve1p, albeit a poor one, and more importantly, Uve1p is capable of recognizing and cleaving a non-UV photoproduct dimer lesion.

Uve1p is active on substrates containing non-bulky DNA damages. The ability of Uve1p to recognize and cleave non-UV photoproduct DNA diadducts prompted us to investigate whether other types of base damage could also be recognized by this versatile endonuclease. These damages included abasic sites (AP sites), uracil (U), dihydrouracil (DHU), inosine (I), xanthine (Xn) and 8-oxoguanine (8-oxoG) (Scheme 1C). For these studies, we utilized 37-mer oligonucleotide substrates with the damages placed near the center of the molecule and within the same DNA sequence context (Table 1B). These oligonucleotides, Ap-37mer, U-37mer, DHU-37mer and 8-oxoG-37mer were incubated with various Uve1p preparations, and the reaction products were analyzed on DNA sequencing-type gels. In addition, 31mer oligonucleotides containing inosine (I-31 mer) and xanthine (Xn-3 I mer) were also tested as potential Uve1p substrates (Table 1A).

Abasic sites (AP sites) arise in DNA from the spontaneous hydrolysis of N-glycosyl bonds and as intermediates in DNA glycosylase-mediated repair of damaged bases [Sakumi and Sekiguchi (1990) Mutat. Res. 236:161–172]. AP endonucleases cleave hydrolytically 5'to the site to yield a 3'hydroxyl termini, AP lyases cleave by a β-elimination mechanism leaving a 3'-αβ-unsaturated aldehyde [Spiering and Deutsch (1981) J. Biol. Chem. 261:3222–3228]. To determine if Uve1p cleaves AP sites, we incubated affinity-purified GΔ228-Uve1p and Δ228 Uve1p and crude extracts of cells expressing GΔ228-Uve1p with a 5' end-labeled oligonucleotide substrate containing an AP site placed opposite a G residue (AP/G-37mer). The products were analyzed on a DNA sequencing-type gel as before (FIG. 10A, lanes 3, 4 and 5 respectively). E. coli endonuclease III (which has an associated AP lyase activity) and E. coli endonuclease IV (a hydrolytic AP endonuclease) were used to determine if the cleavage products formed during incubation with Uve1p preparations were due to a β-elimination mechanism or hydrolytic cleavage (FIG. 10A, lanes 2 and 6 respectively). Uve1p recognized the AP site in this oligonucleotide substrate and cleaved it in a similar manner to E. coli endonuclease IV. Incubating the Uve1p proteins with an oligonucleotide substrate where the AP site was placed opposite an adenine residue (AP/A-37mer) resulted in no significant change in the amount of cleavage product formed. To further test Uve1p recognition of AP sites, we used unlabeled cs-CPD-30mer as a specific competitor for Uve1p. Addition of 40X unlabeled CPD-30mer to reactions of a 5' end-labeled AP/G-37mer with the purified GΔ228-Uve1p resulted in an ~60% decrease in the amount of product formed. The addition of 40X unlabeled undamaged 30mer (UD-30mer) had no effect on the amount of product observed. Uve1p is capable of recognizing AP sites, and changing the complementary base has little or no effect on the extent of cleavage.

Uracil lesions can occur in DNA by the spontaneous deamination of a cytosine residue. Dihydrouracil is a pyrimidine photoproduct that is formed by the deamination of cytosine with subsequent ring saturation upon exposure to ionizing radiation under anoxic conditions [Dizdaroglu et al. (1993) Biochemistry 45:12105–12111]. To determine if Uve1p recognized uracil and dihydrouracil lesions, we incubated various preparations of Uve1p with 3' end-labeled 37mer oligonucleotides containing uracil and DHU residues placed opposite a G (U/G-37mer, DHU/G-37mer). The results of this set of experiments are summarized in Table 2. Purified GΔ228-Uve1p cleaved U/G-37mer and DHU/G-37mer in a typical Uve1p mediated fashion: immediately 5' to the position of the lesion to form a major product, and again one nucleotide 5' to the damaged site to form a minor product, 90% and 10% of the total Uve1p-mediated cleavage products, respectively. By contrast, U-A pairs in double stranded DNA molecules are not substrates for Uve1p or its truncated derivative of the present invention.

Persistence of uracil and DHU lesions through replication may lead to the incorporation of adenine residues opposite the damaged base. To examine if Uve1p were equally efficient at recognizing uracil and DHU when they were base paired with an adenine residue, we constructed the substrates U/A-37mer and DHU/A-37mer. The results obtained from the analysis of Uve1p cleavage of these substrates are summarized in Table 2. No Uve1p mediated cleavage products were observed when crude extracts from cells expressing GΔ228-Uve1p and purified GΔ228-Uve1p were incubated with the U/A-37mer. Incubating purified GΔ228-Uve1p with DHU/A37mer rather than DHU/G-37mer resulted in a 4-fold decrease in the amount of Uve1 p-mediated cleavage products observed. To determine whether Uve1p cleaves the complementary strand of these substrates (i.e., U/A-37mer, DHU/A-37mer or U/G-37mer, DHU/G-37mer), we conducted similar experiments with these substrates except that the complementary strand was 3' end-labeled. No cleavage products were observed when these substrates were incubated with purified Uve1p protein preparations. Uve1p recognizes and cleaves uracil and DHU when they are placed opposite a G (U/G or DHU/G). However, when the lesions are placed in a situation where Watson-Crick hydrogen-bonding is maintained (U/A or DHU/A), Uve1p either fails to recognize the lesion completely (U/A) or the extent of cleavage is significantly decreased (DHU/G).

Uve1p recognizes and cleaves oligonucleotide substrates containing AP sites, uracil and DHU lesions. AP sites appear to be better substrates for Uve1p than uracil or DHU containing oligonucleotides; Uve1p cleaved AP sites at least 10 times more efficiently than uracil containing 20; substrates and twice as efficiently as DHU containing substrates. However, they are all poorer substrates than UV-induced photoproducts. See Table 3 for a summary of the relative efficiency for cleavage by Uve1p on various substrates.

Additionally, the Uve1 p preparations were incubated with the following substrates to determine if these lesions were capable of being cleaved by Uve1p: inosine and xanthine placed opposite a T or C (I/T-31mer, I/C-31mer and Xn/T-31mer, Xn/C-31mer), and 8-oxoguanine placed opposite all four bases (8-oxoG/G-37mer, 8-oxoG/A-37mer, 8-oxoG/T-37mer, 8-oxoG/C-37mer). No cleavage of either strand in these duplex substrates was observed.

As discussed hereinabove, because of substantial structural differences between CPDs and 6-4PPs, it was not obvious what features of damaged DNA Uve1p recognizes. One possibility is that Watson-Crick base pairing is disrupted for the 3' pyrimidines in both CPDs and 6-4PPs [Jing et al. (1998) *Nucl. Acids. Res.* 26:3845–3853], suggesting that Uve1p might target its activity to mispaired bases in duplex DNA. We therefore investigated the ability of purified GΔ228-Uve1p to cleave duplex oligonucleotides containing all possible combination s of single base mispairs embedded within the same flanking sequence context. For these studies, we utilized a collection of mismatch-containing oligonucleotides (series XY-31mer) which were designed so as to generate all possible mismatch combinations (Table 1B). Strands GX, AX, TX and CX were 3' end-labeled and then annealed to strands GY, AY, TY or CY prior to incubation with purified GΔ228-Uve1p. Reaction products were analyzed on DNA sequencing-type gels (See Examples). The ability of GΔ228-Uve1p to cleave all twelve possible mispair combinations is shown in FIGS. 7A–7D. No DNA strand cleavage was observed for duplex substrates containing normal Watson-Crick G/C or A/T base pairs.

Figure 11A:
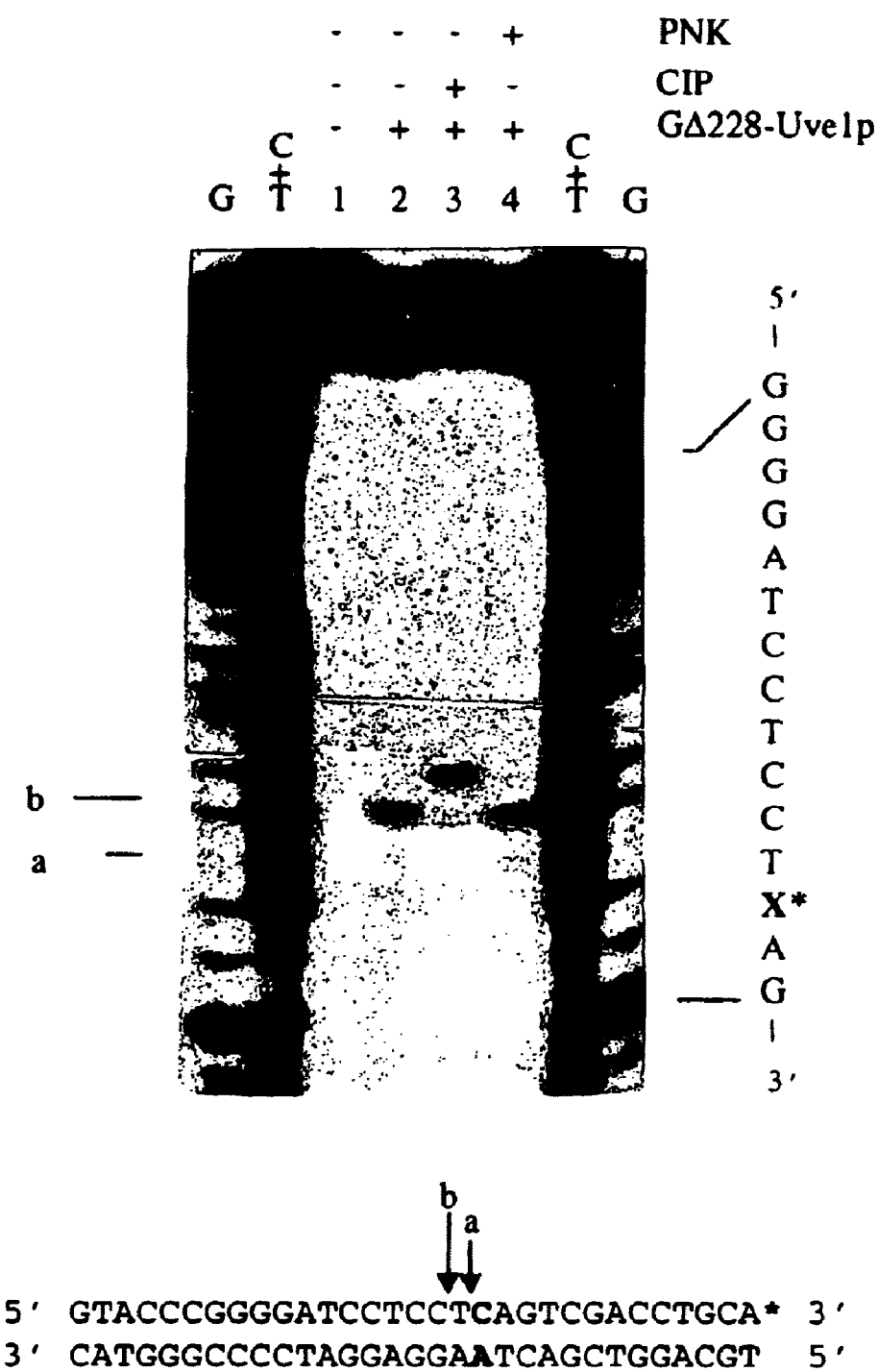
FIGS. 11A–11B characterize the Uve1p-generated DNA strand scission products and activity of full-length Uve1p.
Figure 11B:
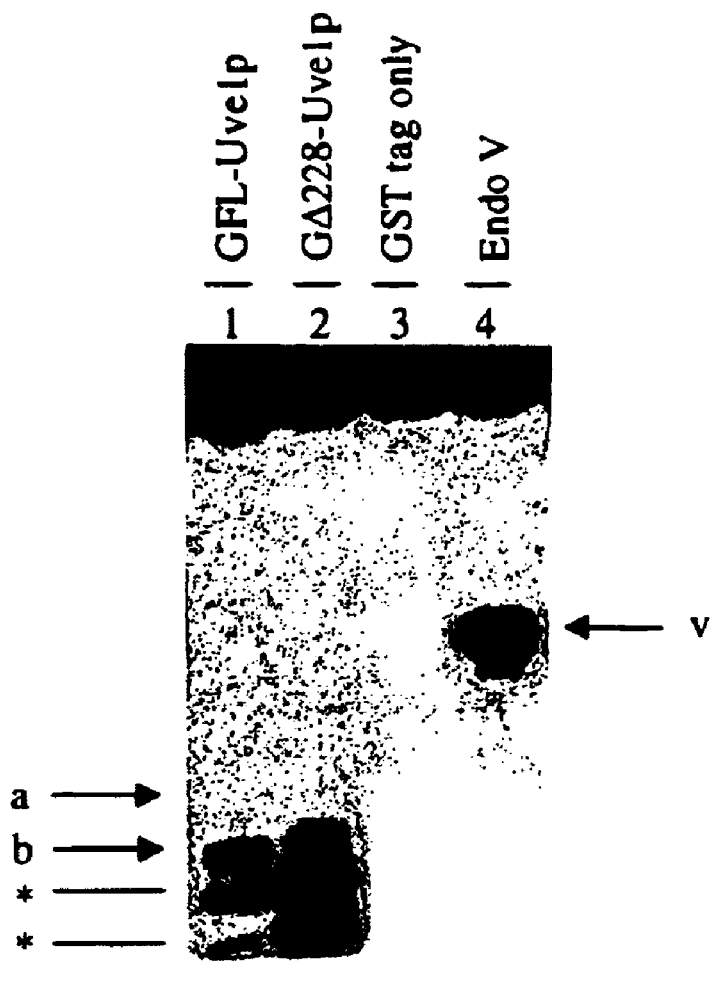
Figure 11B:
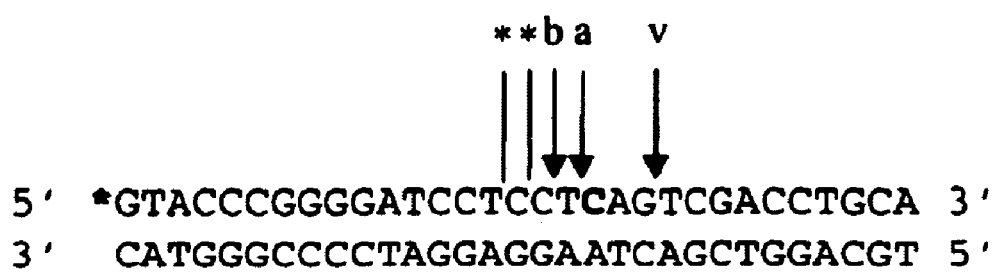

The sites of GΔ228-Uve1 p-mediated mismatch-specific DNA cleavage were identified in each case by comparing the electrophoretic mobilities of the DNA strand scission products to those of a DNA sequencing ladder obtained by base-specific chemical cleavage. Arrows a, b, and c indicate the DNA strand scission products corresponding to cleavage by GΔ228-Uve1p immediately (position 0), one (position −1) or two (position −2) nucleotides 5' to the site of the mismatch, respectively (FIGS. 7A–D). These sites of GΔ228-Uve1p-mediated endonucleolytic cleavage were confirmed in similar experiments employing 5' end-labeled GX, AX, TX and CX strands in the mismatch substrates. In addition, the non-truncated, full-length GFL-Uve1p (in crude cell extracts) recognized and cleaved *CX-AY-31mer in a manner identical to GΔ228-Uve1p (FIG. 11B). The preferred sites of cleavage and the efficiency with which each mismatch is recognized by GΔ228-Uve1p is variable and depends on the type of base mispair that is presented to the enzyme. Within the sequence context examined, GΔ228-Uve1p exhibited strong cleavage at *C/C (asterisk—labeled strand base), *C/A and *G/G sites, moderate cleavage at *G/A, *A/G and *T/G sites, and weak cleavage at *G/T, *A/A, *A/C, *C/T, *T/T and *T/C sites. These differences in the extent of cleavage were reproducible and observed in three separate experiments. These results indicate that the GΔ228-Uve1p mismatch endonuclease activity has a preference for certain base mismatch combinations (e.g. *C/A) over others (e.g. *T/C). However, these experiments do not rule out an effect on cleavage by the sequence(s) flanking the mismatch.

Uve1p has been shown to incise DNA containing CPDs and 6-4PPs directly 5' to the photoproduct site generating products containing 3'-hydroxyl and 5'-phosphoryl groups [Bowman et al. (1994) supra]. We examined whether similar 3' and 5' termini were produced following Uve1p-mediated cleavage of base mismatch-containing substrates. DNA strand scission products generated by GΔ228-Uve1p cleavage of 3' end-labeled oligo *CX/AY-31mer (CX strand labeled, Table 1B) were further treated with calf intestinal phosphatase (CIP) which removes 5' terminal phosphoryl groups from substrate DNA. The major sites of Uve1p-mediated DNA cleavage relative to the base mispair site were found to be at positions 0 and −1 (FIG. 11A, lane 2). CIP treatment of these DNA cleavage products resulted in species that had retarded electrophoretic mobilities compared to non-CIP-treated DNA cleavage products, indicating a decrease in charge corresponding to removal of 5' terminal phosphoryl groups (FIG. 11A, lanes 2 and 3). In addition, GΔ228-Uve1p mismatch endonuclease-generated DNA cleavage products were resistant to phosphorylation by polynucleotide kinase, an expected result if the 5' termini already contain phosphoryl groups (FIG. 11A, lane 4). Electrophoretic mobility shift analysis utilizing 5' end-labeled *CX/AY-31mer, terminal deoxyribonucleotidyl transferase (TdT), and $\alpha^{32}$P-dideoxyATP (ddATP) resulted in addition of a single ddAMP to the 3' end of GΔ228-Uve1p-generated DNA cleavage products and indicates the presence of a 3'-hydroxyl terminus. These results show that the 3' and 5' termini of the products of GΔ228-Uve1p-mediated cleavage of substrates containing single base mismatches are identical to those generated following cleavage of substrates containing CPDs or 6-4PPs.

To verify that the Uve1p mismatch endonuclease activity observed was not the result of trace endonucleolytic contamination from the S. cerevisiae expression system and to determine whether full length Uve1p was also capable of mismatch endonuclease activity, extracts from cells overexpressing GFL-Uve1p, GΔ228-Uve1p, and GST tag alone were tested for their abilities to cleave 5' end-labeled *CX/AY-31mer. Both GFL-Uve1p and GΔ228-Uve1p cleaved the base mismatch-containing substrate at positions 0, −1, and −2 (FIG. 11B). We also observed a weak 3' to 5' exonucleolytic activity associated with both crude GFL-Uve1p preparations and purified GΔ228-Uve1p which shortened the Uve1p-mediated cleavage products by one to three nucleotides (FIG. 11B, lanes 1 and 2). These shorter products are not due to additional cleavages by Uve1p mismatch endonuclease activity because they are not observed in identical experiments with 3' end-labeled substrates. Purified Δ228-Uve1p obtained following thrombin cleavage of the GST tag also possessed mismatch endonuclease activity. In contrast, no cleavage of mismatch-containing substrates was observed when extracts from cells transfected with vector expressing only the GST tag were tested. Thus, both GFL-Uve1p and its more stable, truncated version, GΔ228-Uve1p, both possess mismatch endonuclease activities.

GΔ228-Uve1p mismatch endonuclease and GΔ228-Uve1p UV photoproduct endonuclease share similar properties and compete for the same substrates. GΔ228-Uve1p requires divalent cations for activity and exhibits optimal activity against UV photoproducts in the presence of 10 mM $MgCl_2$ and 1 mM $MnCl_2$. Omission of divalent cations from the reaction buffer abolished GΔ228-Uve1p mismatch endonuclease activity on 5' end-labeled *CS/AY-31mer. The pH optimum for GΔ228-Uve1p mismatch endonuclease activity on this same substrate was found to be 6.5, which corresponds to the pH where optimal activity is observed against UV photoproducts.

Figure 12:
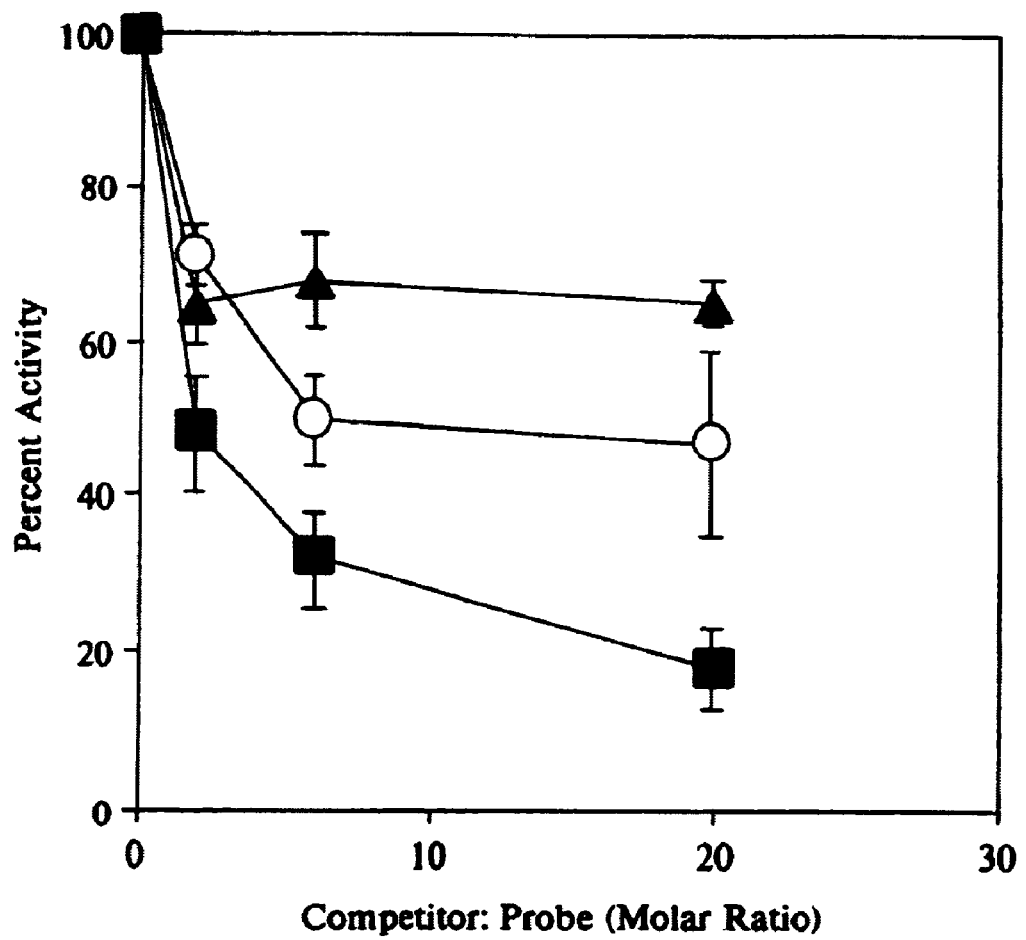
FIG. 12 shows that GΔ228-Uve1p mismatch endonuclease and GΔ228-Uve1p UV photoproduct endonuclease compete for the same substrates. GΔ228-Uve1p was incubated with 3'-end-labeled duplex *CX/AY-31mer (Table 1) in the presence of increasing amounts of unlabeled duplex CPD-30mer (squares) or duplex GX/CY-31mer (triangles) or duplex CX/AY31 mer (circles). The Uve1p-mediated DNA cleavage products were analyzed on DNA sequencing gels, and the extent of strand scission was quantified by PhosphorImager analysis. Uve1p activity is expressed as the percentage of the cleavage observed relative to that observed in the absence of any competitor (defined as 100% activity). The error bars indicate the mean±standard deviation from three separate experiments.

To further confirm that the mismatch endonuclease activity was mediated by GΔ228-Uve1p, a substrate competition experiment was performed with CPD-30mer, a known Uve1p substrate which contains a centrally located UV photoproduct (CPD). Addition of increasing amounts of unlabeled CPD-30mer resulted in a significant, concentration-dependent decrease in GΔ228-Uve1p-mediated mismatch endonuclease activity against 3' end-labeled *CX/AY31mer (C/A mispair) (FIG. 12). In contrast, increasing amounts of the undamaged oligo GX/CY-31 mer (G/C base pair) had only a modest inhibitory effect, and inhibition did not increase with increasing amounts of added oligo, indicating a non-specific binding to Uve1p within this concentration range. In a similar experiment both unlabeled CPD-30mer and CX/AY-31 mer (C/A mispair) were more potent inhibitors of 3' end-labeled *CX/AY-31 mer cleavage compared to unlabeled GX/CY-31mer. The effective competition by CPD-30mer for mismatch endonuclease activity indicates that both base mismatch and UV photoproduct endonuclease activities are associated with GΔ228-Uve1p.

Figure 13A:
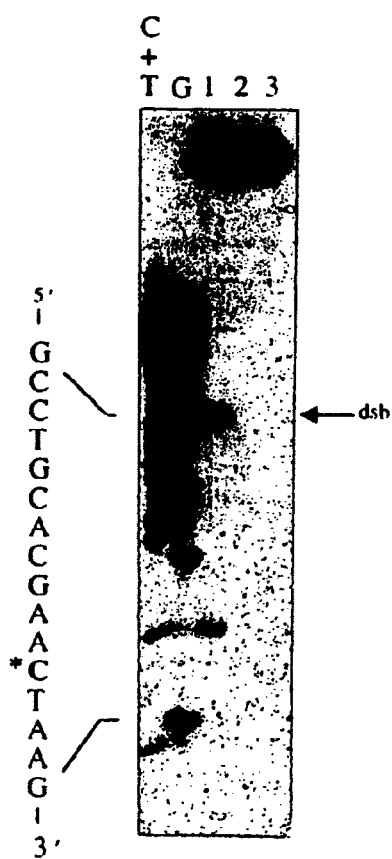
FIGS. 13A–13B show that Uve1p incises only one strand of a duplex containing a base mismatch.
Figure 13B:
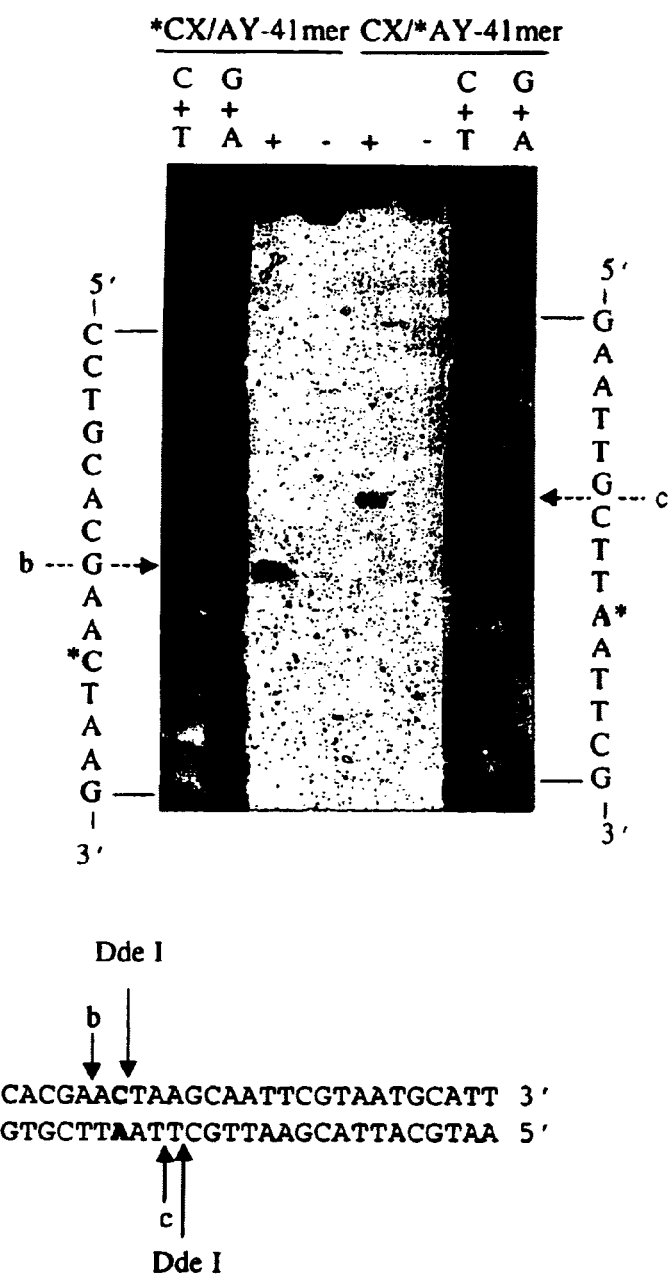

Uve1p incises only one strand of a duplex containing a base mismatch. Since Uve1p recognizes all possible base mismatch combinations, we determined whether the enzyme could incise both strands on the same molecule resulting in a DNA double strand break. An oligonucleotide (*CX/AY-41mer) was designed such that the base mispair was placed in the center of the oligonucleotide. GΔ228-Uve1p was incubated with 3' end-labeled *CS/AY-41mer under standard conditions, and the DNA strand scission products were analyzed on both non-denaturing and denaturing gels (FIGS. 13A–13B). In the event that GΔ228-Uve1p created a DNA double strand break by incising 5' to the base mismatch site on the two complementary strands, the resulting products would possess an electrophoretic mobility similar to those created by the restriction enzyme DdeI (which cleaves adjacent to the mismatch) when analyzed on a non-denaturing polyacrylamide gel. In contrast, if GΔ228-Uve1p incises on either (but not both) complementary strands, then the resulting product would be a full-length duplex containing a single strand nick which would co-migrate with uncut duplex *CX/AY-41mer on a non-denaturing gel. Non-denaturing gel analysis of GΔ228-Uve1p-treated *CX/AY-41mer generated a product with an electrophoretic mobility identical to the untreated duplex with no products detected corresponding to those created by a double strand break (FIG. 13A). Denaturing gel analysis revealed a GΔ228-Uve1p-generated DNA strand scission product resulting from a single strand break of the labeled strand of either *CX/AY-41mer or CX/*GY-41mer. Together with the non-denaturing gel analysis, these results indicate that within the GΔ228-Uve1p substrate population, nicks occur on one or the other, but not both strands (FIG. 13B). These results show that GΔ228-Uve1p nicks only one of the two strands containing a base mismatch and that it does not make double strand breaks in duplex DNA. Similarly, double strand breaks are not made in DNA molecules containing other structural distortions.

Without wishing to be bound by theory, it is believed that GΔ228-Uve1p possesses strand specificity directed towards the 3' terminus. Mismatched bases in duplex DNA are distinct from damaged DNA in the sense that both of the bases are usually undamaged per se, yet one is an inappropriate change in the nucleotide sequence and must be identified as such and removed. If Uve1p participates in MMR in vivo, how might it distinguish between the correct and incorrect bases in a mispair? One possibility is that proximity of the mispaired base to either the 3' or 5' terminus targets Uve1p mismatch endonuclease activity to a particular strand. For example, in DNA synthesis, chain growth proceeds from the 5' to the 3' terminus and newly-generated base misincorporations on the synthesized strand would be located in close proximity to the 3' terminus. Initiating the removal of such bases by a mismatch repair protein might involve association with a region of DNA in the vicinity of the 3' terminus, followed by targeting of the mispaired base located on that strand. To investigate this possibility, a series of 3' end-labeled oligonucleotides were generated that contained a C/A mispair located at various distances from the ends (Table 1B). The ability of GΔ228-Uve1p to incise the C-containing strand as a function of the distance of C (of the C/A mispair) from the 3' terminus was assessed by quantifying the GΔ228-Uve1p mismatch endonuclease-generated DNA stand scission products following denaturing gel analysis. A minimum level of mismatch cleavage was observed for C at a distance of 16 bp from the 3' terminus and gradually increased to a maximum for C at a distance of 16 bp from the 3' terminus. Closer placement (11 bp) of C to the 3' terminus resulted in a decrease in mismatch endonuclease activity with a complete loss of activity observed at a distance 6 bp from the 3' terminus. The mismatched base located on the strand in closest proximity to the 3' terminus is cleaved preferentially by GΔ228-Uve1p.

uve1 null mutants exhibit a mutator phenotype. We have examined the spontaneous mutation rate of uve1::ura4+ disruption mutants as assayed by the ability to form colonies resistant to the toxic arginine analog L-canavanine. Uptake of L-canavanine in S. pombe is mediated by an arginine permease encoded by the can1+ gene [Fantes and Creanor (1984) J. Gen. Microbiol. 130:3265–3273]. Mutations in can1+ eliminate the uptake of L-canavanine, and mutant cells are able to form colonies on medium supplemented with L-canavanine, whereas wild type cells cannot. We have compared the rate of spontaneous mutagenesis at the can1+ locus in uve1::ura4+ disruption mutants (Sp362) to both a negative control (wild type, 972) and a positive control, pms1::ura4+ (see Example 11 hereinbelow). The pms1 gene product is a homolog of E. coli MutL, and loss of pms1 causes a strong mitotic mutator phenotype and increased postmeiotic segregation [Schar et al. (1997) Genetics 146: 1275–1286].

To determine the relative sensitivity of each yeast strain to L-canavanine, 200 cells from mid-log phase cultures were plated onto PMALU$^g$ plates supplemented with increasing concentrations of L-canavanine. Each of the strains was equally sensitive to L-canavanine. All strains were viable in the presence of lower concentrations of L-canavanine up to and including concentrations of 2.2 μg/ml, while concentrations higher than this were toxic to all strains. However, the colonies which grew in the presence of 2.2 μg/ml L-canavanine were smaller in diameter than the colonies which grew in the presence of lower concentrations.

The mean spontaneous mutation rate of each of the three strains was examined using fluctuation analyses. Single colonies grown on PMALU$^g$ plates were used to inoculate liquid PMALU$^g$ cultures which were grown to saturation. $10^7$ cells were plated onto PMALU$^g$ containing 75 μg/ml L-canavanine sulfate. The number of colonies on 24 plates for each strain was counted after 8 days incubation at 30° C. Both uve1::ura4+ and pms1::ura4+ strains showed an elevated number of resistant colonies compared to wild type. Additionally, the range of values for uve1::ura4+ was broader and higher than for either wild type or pms1::ura4+ and included two confluent plates scored as containing >5000 colonies. The mean rate of mutation was estimated using the method of the median [Lea and Coluson (1943) J Genet. 49:264–284] using the median values. The calculated mutation rates are $1.5 \times 10^{-7}$ (wild type), $9.7 \times 10^{-7}$ (uve1::ura4+), and $2.0 \times 10^{-6}$ (pms1::ura4+), indicating that uve1::ura4+ mutants have a spontaneous mutation rate approximately 6.5-fold greater than wild type and 2-fold lower than pms1::ura4+. See Table 4 for a summary of results. Thus, loss of Uve1p confers a spontaneous mutator phenotype in S. pombe. In the mutation fluctuation analysis, a wide range of mutant colonies was observed for uve1::ura4+ compared to uve1::ura4+, suggesting that the pathways leading to mutation due to elimination of uve1 and pms1 are likely to be mechanistically different.

The finding that Uve1p recognizes all potential DNA base mispair combinations indicates that, in addition to its UV photoproduct cleavage activity, it is a diverse mismatch endonuclease with broad substrate specificity. In this regard, Uve1p is similar to E. coli endonuclease V [Yao and Kow (1994) J. Biol. Chem. 269:31390–31396], a S. cerevisiae and human "all-type" mismatch endonuclease [Chang and Lu (1991) Nucl. Acids Res. 19:4761–4766; Yeh et al. (1991) J. Biol. Chem. 266:6480–6484] and calf thymus topoisomerase I [Yeh et al. (1994) J. Biol. Chem. 269:15498–15504] which also recognize all potential base mismatch combinations. These enzymes incise DNA at each of the twelve base mispairs with variable efficiencies and either to the 5' (human all-type mismatch endonuclease) or 3' (E. coli endonuclease V) sides of a mismatch. Uve1p shows a preference for *C/C and *C/A mispairs, a property similar to the human all-type mismatch endonuclease [Yeh et al. (1991) supra]. In contrast, the strong preference of Uve1p for *G/G mispairs is a property which distinguishes Uve1p from all other mismatch endonucleases identified to date.

The biochemical properties of Uve1p-mediated mismatch cleavage and the spontaneous mutator phenotype displayed by uve1 null mutants indicate that Uve1p is involved in MMR in vivo. The preference for making incisions on the strand harboring the mispaired base nearest to the 3' terminus reflects a discrimination strategy that might specifically target newly misincorporated bases during replication. Uve1p-generated incision 5' to the base mismatch site could be followed by a 5' to 3' exonuclease activity such as that mediated by S. pombe exonuclease I [Szankasi and Smith (1995) Science 267:1166–1169] or the FEN-1 homolog Rad2p [Alleva and Doetsch (1998) Nucl. Acids Res. 26:3645–3650] followed by resynthesis and ligation.

S. pombe possesses at least two distinct mismatch repair systems and whether Uve1p mediates a role in either of these or represents a third, novel pathway is not known at present. The proposed major pathway does not recognize C/C mismatches and has relatively long (approximately 100 nt) repair tracts [Schar and Kohli (1993) Genetics 133:825–835]. Uve1p is thought to participate in a relatively short patch repair process which utilizes Rad2p (a FEN-1 homolog) DNA polymerase δ, DNA ligase and accessory factors [Alleva et al. (1998) Nucl Acids Res. 26:3645–3650]. Based on these properties, it is unlikely that Uve1p is involved in a long tract mismatch repair system. The second, presumably less frequently utilized, (alternative) pathway recognizes all potential base mismatch combinations and has a repair tract length of about 10 nucleotides [Schar and Kohli (1993) supra]. These features of the alternative mismatch repair pathway are consistent with the repair properties of Uve1p based on recognition of C/C mismatches and short repair patch.

Unlike in repair of UV photoproducts, it is not clear in mismatch repair which base represents the nucleotide that needs to be removed. This can be explained by our finding that Uve1p prefers a mispaired base located near the 3' terminus of a duplex, which is consistent with Uve1p mediating mismatch repair for either leading or lagging strand synthesis during DNA replication. The preference for making incisions on the strand of the base nearest to the 3' terminus suggests a discrimination strategy to specifically target newly synthesized misincorporated bases. On the other hand, G/G, C/C mismatches are not frequently occurring base misincorporations encountered during replication, although they are among the most efficiently cleaved by Uve1p. A second role for Uve1p is in the correction of mismatched bases formed as a result of homologous recombination events where G/G and C/C mismatches would be expected to occur. A third role for Uve1p is in the repair of base bulges and loops generated as a result of primer-template misalignments during replication. Preliminary studies show that Uve1p mediates strand cleavage 5' to small bulges.

The present inventors have characterized the ability of Uve1p to recognize and incise duplex DNA containing mismatches, IDLs and hairpins. In addition, a determinant of the strand specificity for Uve1p-mediated DNA cleavage has been examined. Evidence that the 3'-terminus of the strand containing a mismatch is involved in directing the strand specificity of Uve1p is presented, and the implications for such strand discrimination are discussed.

What is the structural basis for lesion recognition by Uve1p? Previous studies with Uve1p have focused exclusively on its role in the repair of UV light-induced DNA damage, resulting in the notion that this enzyme functions in the repair of UV photoproducts exclusively, hence the prior name UVDE (UV damage endonuclease), now Uve1p. The results of this study clearly indicate a much broader involvement of Uve1p in *S. pombe* DNA repair and show that many other types of DNA lesions are recognized by this versatile repair protein. For example, we have recently found that Uve1p recognizes and incises DNA substrates containing uracil residues resulting from cytosine deamination, dihydrouracil, cisplatin-induced adducts as well as small base bulges. The molecular basis for substrate recognition by Uve1p is not obvious, but without wishing to be bound by theory, it is believed to be due in part to disruption of normal Watson-Crick base pairing and the corresponding changes expected in the electronic characteristics of the major and minor grooves of B-DNA.

Besides initiating repair of DNA containing UV damage including CPDs and 6-4PPa, UVDE and the truncated UVDE polypeptide of the present invention (Δ228-UVDE and/or GST-Δ228-UVDE) also initiate repair via cleavage of DNA duplexes containing the following base pair mismatches: C/A; G/A; G/G; A/A; and C/T. These experiments were conducted with GST-Δ228-UVDE. We also confirmed that the C/A mismatch is cleaved by Δ228-UVDE; it should also recognize the others. In addition, both GST-Δ228-UVDE and Δ228-UVDE recognize and cleave an oligonucleotides containing a GG-platinum diadduct formed by the antitumor agent cis-dichlorodiammineplatinum (II) (also known as cisplatin). Thus the substrate specificity range for UVDE is much broader than originally thought. Recognition of the truncated UVDE polypeptide to initiate mismatch repair was made possible due to the increased stability of the presently exemplified truncated UVDE polypeptide in substantially purified form.

Herein we describe the ability of Uve1p to recognize and process IDL structures in duplex DNA as well as the determinants of the strand specificity of Uve1p. The ability of GΔ228-Uve1p to process DNA duplexes containing IDL and hairpin structures was investigated with a series of oligonucleotide substrates containing loops of 2–8 nucleotides in length or an 8 bp hairpin structure (Table 17A–17B). The DNA sequence and structures of the substrates are shown in Table 17A–17B. Strands 10, 12, 14, 16, 18 or HP8 were 3'-end-labeled and annealed to strand D0. This annealing reaction formed duplexes ID0, ID2, ID4, ID6, ID8 and HPD8, with 0, 2, 4, 6, 8 nt loops or an 8 bp hairpin, respectively. The substrates were treated with GΔ228-Uve1p (FIGS. 14A–14C, even lanes) or with buffer alone (FIGS. 14A–14C, odd lanes). No DNA strand cleavage was observed for the normal homoduplex substrate ID0 (FIG. 14A, lane 2). In contrast, GΔ228-Uve1p cleaves heteroduplexes containing insertions of 2 or 4 unpaired nucleotides (FIG. 14A, lanes 4 and 6). However, the enzyme did not cleave duplexes ID6 or ID8 containing larger loops of 6 and 8 nucleotides, respectively (FIG. 14C, compare lanes 2, 4 and 6).

The results shown in FIGS. 14A–14C indicate that GΔ228-Uve1p produces several cleavage products from the strand containing a 2 or 4 nt unpaired loop. The sites of cleavage correspond to endonucleolytic cleavage of duplexes ID2 and ID4 at a distance of 1 (position a), 15 (position b) and 16 (position c) nucleotides 5' to the IDL (FIG. 14A, lanes 4 and 6). The major site of Uve1p-mediated cleavage on duplex ID2 was observed to be at positions b, and c, whereas the major site of cleavage on duplex ID4 was observed to be at position a. The cleavages at positions a, b and c were also observed when the DNA substrate was labeled at the 5'-terminus of the strand containing the loop (data not shown), which confirms that Uve1p cleaves endonucleolytically at these sites. Uve1p did not cleave DNA containing a base insertion within the context of a small hairpin structure (FIG. 14B, lane 2).

Uve1p has been shown to exhibit a wide substrate specificity, including bipyrimidine UV photoproducts, base mispairs, abasic sites, and platinum GG diadducts in duplex DNA [Kaur et al. (1999) *Mol. Cell. Biol.* 19:4703–4710; Avery et al. (1999) *Nucleic Acids Res.* 27(11):2256–2264; Kanno et al. (1999) *Nucleic Acids Res.* 27:3096–3103]. For each of these lesions, GΔ228-Uve1p cleaves endonucleolytically immediately, one or two nt 5' to the site of base damage. The cleavage events at positions b and c (FIG. 14A) located 15 and 16 nt 5' to the site of the loop of substrates ID2 or ID4 have been observed only with these types of DNA substrates containing small base insertions. Because cleavage events at similar distances 5' to the site of DNA damage were not observed in earlier studies, it seemed possible that the observed distal cleavage events were the result of a sequence-specific structure formed by the particular duplex used in this experiment. Therefore, the generality of this cleavage pattern was tested using IDL substrates within a different DNA sequence context.

Figure 15A:
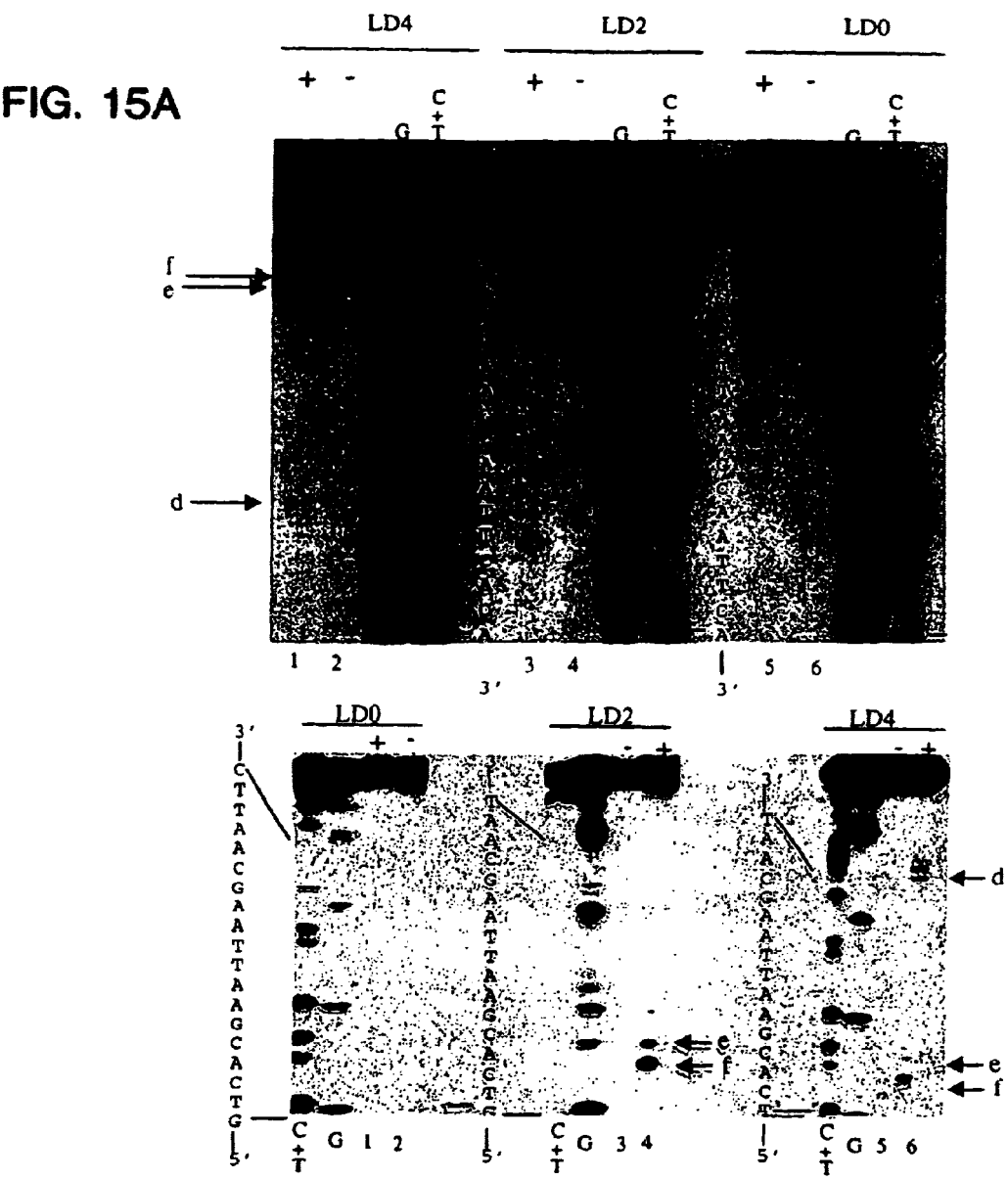
FIGS. 15A–15B: 15 show that Uve1p recognizes short IDL structures within a different sequence context. Cleavage reactions were carried out with (FIG. 15A) 3'-end-labeled or (FIG. 15B) 5'-end-labeled DNA duplexes containing IDLs of 0 (LD0), 2 (LD2) and 4 (LD4) nt in length and GΔ228-Uve1p as described in the text. DNA cleavage products were analyzed on sequencing type gels. Arrows d, e and f indicate DNA strand scission products produced by cleavage events occurring 1, 15 and 16 nt 5' from the IDL site, respectively. G and C+T base-specific chemical cleavage DNA sequencing ladders were run in adjacent lanes as nucleotide position markers. The core sequence of the substrate is shown at the bottom of the figure where X corresponds to the IDL sequence in Table 17A–17B. In Table 17A, the vertical bracket above arrows e and f indicates non-specific cleavage of the substrates and is not observed with 5' end labeled substrates.
Figure 15B:

DNA substrates were constructed by annealing oligonucleotides Lo0, Lo2 and Lo4 to strand Bot to generate duplexes LD0, LD2 and LD4 with loops of 0, 2 and 4 nucleotides, respectively (Table 17B). The strands which form a loop in the duplex (LD0, LD2 and LD4) were either labeled on the 3' (FIG. 15A) or the 5' (FIG. 15B) end. These substrates were incubated with purified GΔ228-Uve1p or with buffer, and the reaction products were analyzed on a 20% denaturing polyacrylamide gel (15A–15B). GΔ228-Uve1p cleaved duplexes LD2 and LD4 with base insertions of 2 or 4 nucleotides. However, as observed previously with the substrates ID6 and ID8, DNA substrates with 6 (LD6) or 8 (LD8) nt insertions were not cleaved by Uve1p (FIG. 14C and data not shown). These results indicate that GΔ228-Uve1p recognizes and cleaves duplex DNA with loops of 2 or 4 nucleotides but not IDL structures of 6 or 8 nucleotide insertions or certain hairpin structures. The extent of GΔ228-Uve1p-mediated cleavage observed with IDL substrates containing 2 and 4 nt insertions was approximately the same as that previously observed for a duplex DNA substrate containing a C/A mispair [Kaur et al. (1999) supra]. Furthermore, for each of these IDL containing duplexes, no cleavage of the opposite strand was observed.

Figure 16:
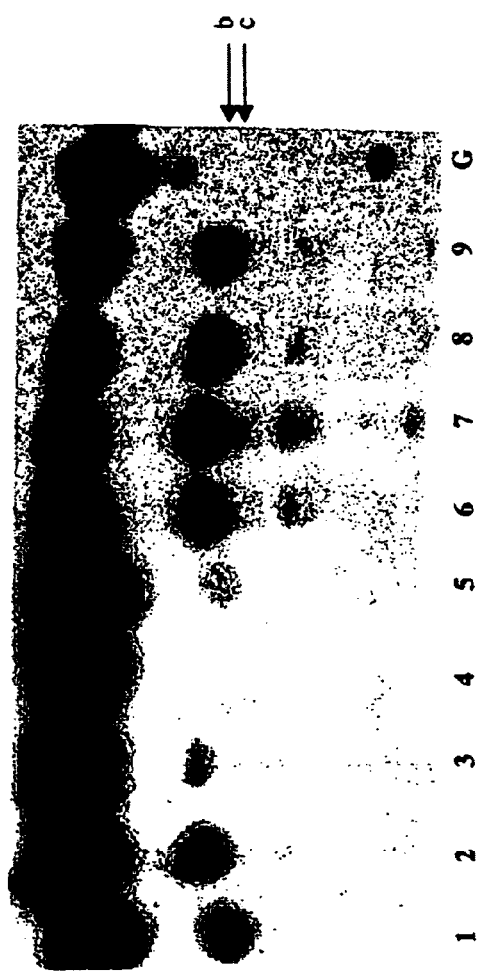
FIG. 16 shows antibody inhibition of Uve1p-mediated activity in an IDL containing substrate. GΔ228-Uve1p was pre-incubated with increasing amounts (40 μg–160 μg) of immune serum (lanes 2–5) or pre-immune serum (lanes 6–9) prior to incubation with 3' end labeled substrate ID2 (sequence indicated at the bottom). The reaction products were analyzed on a 20% denaturing polyacrylamide gel as described (Example). Arrows b and c correspond to GΔ228-Uve1p-mediated DNA cleavage events 15 and 16 nt 5' to the IDL site, respectively. In this gel the two bands representing distinct cleavage events at positions b and c are poorly resolved from each other.

To further investigate the involvement of Uve1p in the recognition and cleavage of substrates containing short IDL structures, antibody inhibition experiments were conducted. Rabbit polyclonal antibodies specific for Δ228-Uve1p were generated. GΔ228pUve1p was preincubated with 40 to 160 μg of pre-immune or immune serum, and endonuclease assays with 3'-end-labeled substrate ID2 were carried out under standard reaction conditions. Preincubation of GΔ228-Uve1p with this antibody significantly decreases GΔ228-Uve1p-mediated cleavage of substrate ID2 in a concentration-dependent manner (FIG. 16, lanes 2–5). In contrast, preincubation with pre-immune serum did not inhibit the GΔ228-Uve1p-mediated endonuclease at any concentration tested (FIG. 16, lanes 6–9). Western blot analysis of the purified GΔ228-Uve1p with the immune serum produced a single band, indicating that the antibody does not cross-react with any trace contaminating proteins in the purified GΔ228-Uve1p preparation used in these experiments. The specific inhibition of the IDL cleavage activity of GΔ228-Uve1p by the antibody indicates that the observed cleavage of the IDL containing substrates was associated with GΔ228-Uve1p.

We have demonstrated that Uve1p recognizes and processes UV photoproducts and all twelve base mispair combinations in a similar manner [Kaur et al. (1998) *Biochemistry* 37:11599–11604; Kaur et al. (1999) supra; Avery et al. (1999) supra]. We have further demonstrated that Uve1p is also capable of recognizing small IDL structures. We examined the features of known Uve1p substrates which confer specificity with respect to DNA strand cleavage preference. The substrate specificity of Uve1p in vitro indicates its usefulness in repair of mismatches or IDL structures in vivo. It was important to determine how the enzyme distinguishes between the "correct" and "incorrect" base in a mispair. One possibility is that the proximity of one of the mispaired bases to either the 3' or the 5' terminus might direct strand specificity for cleavage. For example, *E. coli* endonuclease V is a mismatch endonuclease that displays strong strand specificity, preferring to cleave the strand containing the mispaired base closest to the 5'-terminus [Yao and Kow (1994) *J. Biol. Chem.* 269:31390–31396]. We tested the possibility that the strand specificity of GΔ228-Uve1p is affected by the nature of the terminus in closest proximity to the mispair.

Figure 17A:
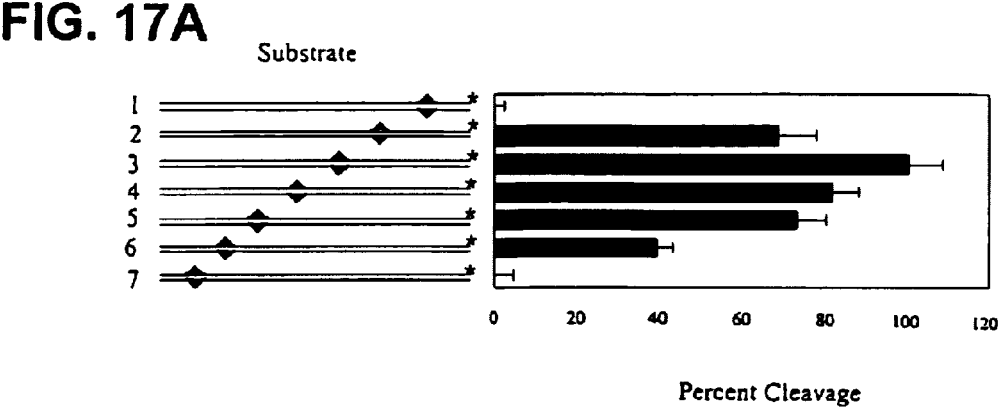
FIGS. 17A–17C show the strand specificity of Uve1p is influenced by the proximity of the mispaired base to the 3'-terminus. DNA substrates used in this experiment are shown in the Table 1. Number and letter designations adjacent to substrates correspond to the oligonucleotide names given in Table 17A–17B. Duplex substrates were 3'-end-labeled (*) on (FIG. 17A) C-containing or (FIG. 17B) A-containing strands and incubated with GΔ228-Uve1p as described below. The extent of DNA strand scission (expressed as percent of total substrate cleaved) was quantified by phosphorimager analysis.
Figure 17B:
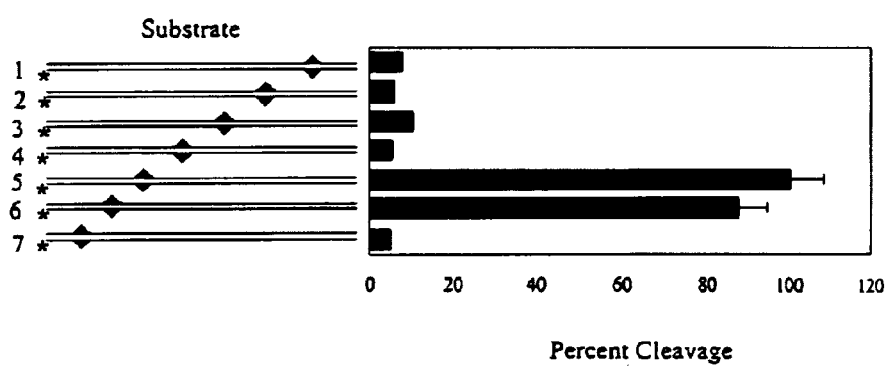

A series of oligonucleotides (41-mers) which form DNA duplexes with a single C/A mispair at different positions within the sequence and at different distances from the termini of the linear duplex DNA molecule were synthesized (Table 18). The C-containing strand was 3' end labeled and the relative cleavage activity of GΔ228-Uve1p on this strand was quantified (FIG. 17A). DNA cleavage was relatively inefficient at the C on this strand when located 37 nt from the 3' terminus, gradually increased to a maximum when located 16 nt from the 3'-terminus, and was undetectable when located 6 nt from the 3'-terminus. A similar result was obtained when the A-containing strand of the C/A mispair was analyzed (FIG. 17B). These results indicate that the cleavage efficiency of Uve1p at a C/A mismatch is sensitive to the proximity of the mispaired base to the 3' terminus. However, in this experiment, the flanking DNA sequence context of the C/A mispair varies at different positions within the DNA duplex, which also influences the cleavage efficiency of Uve1p.

Figure 17C:
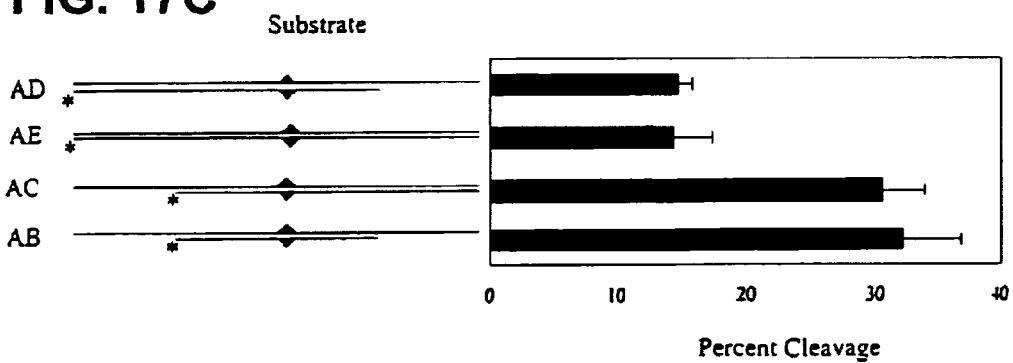

To gain further insight into the strand preferences of Uve1p-mediated DNA cleavage, four duplex DNA substrates (AB, AC, AD, and AE) were designed to test the cleavage efficiency of Uve1p at a C/C mismatch within the same sequence context but at different distances from 3' and 5' termini (Table 18). The length and sequence of the "A" strand of these duplexes was identical in all cases, and the length of the complementary strand (B, C, D, or B) was varied. The cleavage efficiency of GΔ228-Uve1p on strands B, C, D, and E in the substrates AB, AC, AD, or AE was quantified (FIG. 17C). Substrates AB and AC, in which the C/C mispair was 25 nt from the 3'-terminus were cleaved by GΔ228-Uve1p with a similar efficiency. In contrast, the efficiency of cleavage of substrates AD and AE in which the C/C mispair was 40 nt from the 3' terminus was about 2-fold lower. Moreover, the efficiency of cleavage of the duplex substrate appeared to be independent of the distance of the mismatch from 5'-terminus (compare AB with AC and AD with AE). These results are consistent with sensitivity of cleavage of a mispaired base by GΔ228-Uve1p to its proximity to the 3'-terminus of that strand.

Repetitive sequences in DNA are capable of forming IDL structures during replication, which can lead to insertion or deletion mutations [Petruska et al. (1998) supra; Pearson et al. (1998) supra]. MMR systems in both prokaryotes and eukaryotes are utilized for the repair of such IDL structures [Modrich (1991) supra; Kolodoner, R. (1996) supra; Strand et al. (1993) supra]. We have demonstrated that Uve1p incises small IDL structures in DNA, indicating that it helps maintain the stability of repetitive sequences in the genome. Our results also show that Uve1p cleaves DNA 15–16 nucleotides 5' to the IDL structure (FIGS. 14A–14C and 15A–15B). The reasons for such a distal cleavage event are unknown. Without wishing to be bound by any particular theory, we believe that Uve1p causes a distortion in the DNA when it binds to a mismatch and that this distortion leads to the distal cleavage event. In this case, cleavage at the distal site results from a conformation of Uve1p and DNA unique to the complex formed by Uve1p at an IDL.

The substrate specificity of Uve1p, including IDL structures as well as base mispairs, is not a unique property of Uve1p and its truncated derivatives. *E. coli* endonuclease V, spinach nuclease SP, and T4 endonuclease VII also share these properties in that they recognize and cleave DNA containing base mispairs and small IDLs [Mizuuchi et al. (1982) *Cell* 29:357–365; Golz et al. (1996) *DNA Res.* 2:277–284; Greger and Kemper (1998) *Nucleic Acids Res.* 26(19):4432–4438]. However, these enzymes also differ from each other with respect to the sites and extent of cleavage in proximity to the DNA distortion as well as their recognition of other types of DNA damages and other types of DNA structures. In addition, the physical characteristics and environment in which optimal activity varies considerably from enzyme to enzyme.

Uve1p does not recognize hairpin type structures. In this respect, Uve1p is distinct from *E. coli* endonuclease V, but similar to *S. cerevisiae* insertion mismatch recognition activity [Miret et al. (1996) *Nucleic Acids Res.* 24(4):721–729]. IDL structures that form hairpins are considered to be poor substrates for repair [Nag et al. (1989) *Nature* 340(6231): 318–320] and demonstrate a low rate of repair in vivo in *S. cerevisiae* [Moore et al. (1999) *Proc. Natl. Acad. Sci. USA* 96(4):1504–1509]. The recombinant GST tagged, truncated version of Uve1p has been utilized in all these experiments. Without wishing to be bound by theory, we believe it reflects the substrate specificity of the native Uve1p enzyme in vivo.

In order to contribute to mismatch repair in vivo in a manner that maintains genomic stability, Uve1p requires a mechanism for strand discrimination. Our results indicate that during mismatch recognition and cleavage, the strand preference of Uve1p is determined by the proximity of a mispaired base to the 3'-terminus. This strand selection mechanism is believed to reflect the fact during DNA replication newly generated base misincorporations in the lagging strand are close to the DNA 3'-terminus associated with the replication fork. In this way, repair of mispair and IDL structures by Uve1p contribute to genomic stability in vivo.

Recent studies indicate that DNA repair pathways for damaged DNA bases are also in some cases involved in mismatch repair [Sancar, A. (1999) supra; Oleykowski et al. (1999) *Biochemistry* 38:2200–2205]. Rad1p, a nucleotide excision repair protein of *S. cerevisiae*, is considered important for the repair of DNA loops [Kirkpatrick and Petes (1997) *Nature* 387:929–931]. Biochemical as well as genetic evidence indicates that the Rad1p/Rad10p endonuclease is absolutely required for nucleotide excision repair of UV damaged DNA and that it also functions in genetic recombination [Davies et al. (1995) *J. Biol. Chem.* 270:24638–24641; Habraken et al. (1994) *Nature* 371:531–534; Bardwell et al. (1994) *Science* 265:2082–2085]. *S. pombe* Rad16p and Swi10p, are the homologs of the yeast Rad1p and Rad10p. Mutations in these two proteins reduce the frequency of mating-type switching and also confer a radiation-sensitive phenotype [Schmidt et al. (1989) *Curr. Genet.* 16:89–94; Carr et al. (1994) *Mol. Cell. Biol.* 14.2029–2040; Hang et al. (1996) *Gene* 170(1):113–117]. There is also evidence indicating that mismatch repair proteins recognize various types of DNA adducts [Marra and Schar (1999) *Biochem. J.* 338: 1–13]. Thus, Uve1p participates in the repair of UV-induced DNA damage as well as DNA replication-associated mismatch or IDL lesions of five or fewer nucleotides in the loop. We further believe Uve1p acts in concert with both DNA excision repair and mismatch repair pathways.

Skin cancers associated with sunlight exposure are the most common worldwide human cancers. The primary DNA damage from exposure to sunlight are 6-4 PPs and CPDs. Since UVDE can augment cells defective in DNA repair, the stable truncated UVDE fragments of the present invention will be valuable therapeutic agents for correcting DNA repair defects in sunlight-sensitive and skin cancer-prone individuals, for example individuals with the genetic disease xeroderma pigmentosum. Additionally, GST-Δ228-UVDE and Δ228-UVDE can be used as protective agents against sunlight-induced skin damage in normal individuals because they can augment the existing DNA repair levels of CPDs and 6-4 Pps and other DNA damage.

Homologs of the *S. pombe* UVDE protein have been identified by BLAST searching of sequence database (Genbank, TIGR) using the UVDE amino acid sequence: *N. crassa* (Genbank Accession No. BAA 74539), *B. subtilis* (Genbank Accession No. 249782), human (Genbank Accession No. AF 114784.1, methyl-CpG binding endonuclease) and a *Deinococcus radiodurans* sequence located from the TIGR database. The amino acid sequences of these proteins are given in SEQ ID NO:36 (*N. crassa*), SEQ ID NO:37 (*B. subtilis*), SEQ ID NO:38 (*Homo sapiens*) and SEQ ID NO:39 (*D. radiodurans*). The *D. radiodurans* coding sequence can be generated using the genetic code and codon choice according to the recombinant host in which the protein is to be expressed, or the natural coding sequence can be found on the TIGR database, *D. radiodurans* genomic sequence in the region between bp 54823 and 60981. Additional homologs of the *S. pombe* UVDE include the UV damage enzyme of *Bacillus anthracis*; *Halobacterium* sp., disclosed in Genbank Accession No. AAC 82899; *Methanococcus jannaschii*, disclosed in Genbank Accession No. 057597; and *Thermotoga maritima*, disclosed in Genbank Accession No. AE001740. These homologs were identified using Blast or FastA on the NCBI or TIGR websites. A Uve1p consensus sequence has been derived using the vector NTI AlignX program. This consensus sequence spans amino acids 308–465 of the C-terminal region of the *S. pombe* Uve1p. This region shows significant sequence similarity to portions of the *B. subtilis* and *N. crassa* Uve1p equivalents.

The regions of the *S. pombe* UVDE protein which are most conserved in the foregoing homologs are amino acids 474–489, 535–553, 578–611, 648–667, 711–737 and 759–775 of SEQ ID NO:2.

The stable truncated UVDE derivatives of the present invention are useful to treat or prevent diseases caused by cyclobutane pyrimidine dimers or (6-4) photoproducts or DNA mismatch, abasic sites or other distortions in the structure of double stranded DNA through the application of skin creams which can deliver GST-Δ228-UVDE and Δ228-UVDE to the appropriate living cells or via other routes of administration with compositions suitable for the route of administration, as is well understood in the pharmaceutical formulation art. GST-Δ228-UVDE or Δ228-UVDE can be incorporated into liposomes, and the liposomes can be applied to the surface of the skin, whereby the encapsulated GST-Δ228-UVDE and Δ228-UVDE products traverse the skin's stratum corneum outer membrane and are delivered into the interior of living skin cells. Liposomes can be prepared using techniques known to those skilled in the art. A preferred liposome is a liposome which is pH sensitive (facilitates uptake into cells). Preparation of pH sensitive liposomes is described in U.S. Pat. No. 5,643,599, issued to Kyung-Dall et al.; and U.S. Pat. No. 4,925,661 issued to Huang. The GST-Δ228-UVDE and Δ228-UVDE polypeptides can be entrapped within the liposomes using any of the procedures well known to those skilled in the art. See, e.g., the Examples and U.S. Pat. No. 4,863,874 issued to Wassef et al.; U.S. Pat. No. 4,921,757 issued to Wheatley et al.; U.S. Pat. No. 5,225,212 issued to Martin et al.; and/or U.S. Pat. No. 5,190,762 issued to Yarosh.

The concentration of liposomes necessary for topical administration can be determined by measuring the biological effect of GST-Δ228-UVDE and Δ228-UVDE, encapsulated in liposomes, on cultured target skin cells. Once inside the skin cell, GST-Δ228-UVDE or Δ228-UVDE repairs CPDs or 6-4 Pps in damaged DNA molecules and increases cell survival of those cells damaged by exposure to ultraviolet light.

Polyclonal or monoclonal antibodies specific to GST-Δ228-UVDE and Δ228-UVDE allow the quantitation of GST-Δ228-UVDE and Δ228-UVDE entrapped into liposomes. GST-Δ228-UVDE and Δ228-UVDE antibodies also allow tracing of the truncated UVDE polypeptides into skin cells.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition. Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* Part I; Wu (ed.) (1979) *Meth Enzymol.* 65; Miller (ed.) (1972) *Experiments in Molecular Genetics*, Cold Spring Harbor Laboratory, Cold Spring Harbor, N.Y.; Old Primrose (1981) *Principles of Gene Manipulation*, University of California Press, Berkeley; Schleif and Wensink (1982) *Practical Methods in Molecular Biology*; Glover (ed.) (1985) *Nucleic Acid Hybridization*, IRL Press, Oxford, UK; and Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein.

Each reference cited in the present application is incorporated by reference herein to the extent that it is not inconsistent with the present disclosure.

The following examples are provided for illustrative purposes, and are not intended to limit the scope of the invention as claimed herein. Any variations in the exemplified articles which occur to the skilled artisan are intended to fall within the scope of the present invention.

EXAMPLES

Example 1

Strains, Enzymes, Plasmids and Genes

E. coli Top 10 (Invitrogen Corp., San Diego, Calif.) was used for subcloning and plasmid propagation. S. cerevisiae strain DY150 used for protein expression and the S. cerevisiae expression vector pYEX4T-1 were purchased from Clontech (Palo Alto, Calif.).

S. pombe strains used in this study include 972, h$^{-S}$ [Leupold, U. (1970) Meth. Cell Physiol. 4:169–177]; PRS301, h$^{-S}$ pms1::ura4$^+$ [Schar et al. (1993) Genetics 146:1275–1286]; SP30, h$^{-S}$ ade6–210 leu-32 ura4-D18 [Davey et al. (1998) Mol. Cell. Biol. 18:2721–2728]. Sp362 (h$^{-S}$ ade6–210 leu1–32 ura4-D18 uve1::ura4$^+$) was constructed by transforming Sp30 with a linearized, genomic uve1$^+$ fragment derived from pgUV2 [Davey et al. (1997) Nucl. Acids Res. 25:1005–1008] in which nucleotides 215 (EcoRI) to 1045 (ClaI) of uve1$^+$ were replaced with the ura4+gene. Extracts of Sp362 contained no detectable Uve1p activity against CPD-30mer. Cultures were grown in pombe minimal medium (PM) [Leupold (1970) supra] with 3.75 g/l glutamate replacing ammonium chloride as the nitrogen source [Fantes and Creanor (1984) J. Gen. Microbiol. 130:3265–3273], and were supplemented with 150 mg/l of each adenine, leucine and uracil (PMALU$^g$). Solid media was prepared by addition of 20 g/l agar. L-canavanine sulfate was sterilized prior to addition to the medium.

Purified mismatch repair endonuclease, E. coli endonuclease V [Yao and Kow (1997) J. Biol. Chem. 272:30774–30779] was a gift from Yoke Wah Kow (Atlanta, Ga.).

Example 2

Amplification of the Uvde (Uve1) Gene from S. pombe.

A cDNA library purchased from ATCC was amplified by PCR, using the sense primer: 5'-TGAGGATCCAATCGTTTTCATTTTTTAATGCTTAGG-3' (SEQ ID NO:9) and the antisense primer: 5'-GGCCATGGTTATTTTTCATCCTC-3' (SEQ ID NO:10). The gene fragment of interest was amplified in the following manner. Four hundred nanograms of template DNA (S. pombe cDNA library) was incubated with the upstream and downstream primers (300 nM) in the presence of Pwo DNA polymerase (Boehringer Mannheim, Indianapolis, Ind.) in 10 mM Tris-HCl (pH 8.85), 25 mM KCl, 5 mM (NH$_4$)$_2$SO$_4$, 2 mM MgSO$_4$ and 200 µM of dNTPs. The DNA was initially denatured at 94° C. for 2 min. Three cycles of denaturation at 94° C. for 15 sec, annealing at 45° C. for 30 sec and primer extension at 72° C. for 2 min were followed by twenty cycles using 50° C. as the annealing temperature. All other incubation times and temperatures remained the same. The amplification was completed by a final primer extension at 72° C. for 7 min.

Example 3

Amplification of the Δ228-UVDE Gene-Encoding Fragment from S. pombe.

PCR was used to produce a truncated DNA fragment of the full-length S. pombe uvde gene which encodes a protein product containing a deletion of 228aa from the N-terminal portion of the full-length S. pombe UVDE protein. The following primers were used in the PCR reaction to amplify the gene fragment which encodes Δ228-UVDE: sense primer 5'AATGGGATCCGATGATCATGCTCCACGA-3' (SEQ ID NO:11) and the antisense primer 5'GGGATCCTTATTTTTCATCCTCTTCTAC-3' (SEQ ID NO: 12). PCR conditions were as described in Example 2.

Example 4

Purification of Δ228-UVDE and Full-Length UVDE

The amplified UVDE gene coding fragments were cloned into the BamHI and SmaI restriction sites of pYEX 4T-1. The Δ228-UVDE gene coding fragments were cloned into the BamHI restriction site of pYEX4T-1 (Clontech, Palo Alto, Calif.). In the pYEX4T-1 vector, the coding region of both the proteins is expressed in frame with a glutathione-S-transferase (GST) leader sequence to generate a fusion protein of GST linked to the N-terminus of UVDE which is under the control of the CUP1 promoter [Ward et al. (1994) Yeast 10:441–449]. The subcloned plasmids were checked for orientation by restriction analysis and were then transformed into S. cerevisiae, DY150 cells, using the alkali cation method [Ito et al. (1983) supra]. A single positive clone was picked and grown at 30° C. until mid log phase. Cultures in mid log phase were induced with 0.5 mM CuSO$_4$. Cells (500 mL) were harvested 1 or 2 hr after induction and lysed with glass beads in 50 mM Tris (pH 7.5), 100 mM EDTA, 50 mM NaCl, 10 mM β-mercaptoethanol, 5% glycerol in the presence of 10 ng/mL pepstatin, 3 nM leupeptin, 14.5 mM benzamidine, and 0.4 mg/mL aprotinin. The cell lysate was then dialyzed overnight in buffer minus EDTA. The whole cell homogenate was separated into soluble and insoluble fractions by centrifugation at 45,000 X g for 20 min. The soluble proteins (120 mg) were applied to a 2 mL glutathione-Sepharose-affinity column (Pharmacia, Piscataway, N.J.). All purification steps were carried out at 4° C. and are similar to the strategies employed for the purification of other types of GST-tagged proteins [Ward et al. (1994) Yeast 10:441–449; Harper and Speicher (1997) In: Current Protocols in Protein Sci. (Coligan, J. et al., Eds), John and Wiley & Sons, pp. 6.6.1–6.6.21). Unbound proteins were removed by washing with 30 mL phosphate-buffered saline (pH 7.4), 5 mM EDTA, 0.15 mM PMSF. GST-Δ228-UVDE was eluted (100–200 µL fractions) with 10 mM glutathione in 50 mM Tris (pH 7.4) or cleaved on the column with excess of thrombin as previously described [Harper and Speicher (1997) supra] to generate Δ228-UVDE without the GST tag. SDS-PAGE analysis of flow-through, wash, elution, and thrombin cleavage fractions indicated the extent of purification or GST tag removal via thrombin cleavage (FIG. 1A–1B). Typically, the GΔ228Uve1p was nearly homogeneous. Purified proteins were stored at −80° C. in 10% glycerol.

Example 5

GST Preparation

S. cerevisiae (DY150) cells were transformed with the pYex4T-1 expression vector without any insert (i.e., expressing gluthathione-S-transferase [GST] alone). These cultures were induced with $CuSO_4$ and cell lysates were prepared as described for the Uve1p proteins. Purified recombinant GST was affinity-purified on a gluthathione sepharose column in an identical manner to GΔ228-Uve1p (see above) and was included in all of the assays performed in this study as a control for trace amounts of potential contaminating endonucleases in the Uve1p protein preparations.

Example 6

UVDE Activity Assay and Optimization of Reaction Conditions

Crude and purified full-length UVDE, GST-Δ228-UVDE and Δ228-UVDE were tested for activity on an oligodeoxynucleotide substrate (CPD-30mer) containing a single cis-syn cyclobutane pyrimidine dimer embedded near the center of the sequence. The sequence of the CPD-containing strand is: 5'-CATGCCTGCACGAAT^ATAAGCAATTCGTAAT-3' (SEQ ID NO:13). The CPD-containing DNA molecule was synthesized as described by Smith and Taylor (1993) *J. Biol. Chem.* 268:11143–11151. The CPD-30mer was 5' end labeled with [γ-$^{32}$P]ATP (Amersham, 3000 Ci/mmol) using polynucleotide kinase [Tabor (1985) vide infra]. For UVDE reactions with end labeled CPD-30mer, approximately 10 fmol of 5' end labeled CPD 30-mer was incubated with 5–100 ng of Δ228-UVDE or GST-Δ228-UVDE, in 200 mM Hepes (pH 6.5), 10 mM $MgCl_2$, 1 mM $MnCl_2$, 150 mM NaCl for 15 min at 37° C. 10–20 μL reaction volume). The reaction products were analyzed on 20% denaturing (7 M urea) polyacrylamide gels (DNA sequencing gels) as previously described (Doetsch, et al., 1985). The DNA species corresponding to the uncleaved CPD-30mer and cleavage product (14-mer) were analyzed and quantified by phosphorimager analysis (Molecular Dynamics Model 445 SI) and autoradiography.

In other experiments, reactions with various Uve1p preparations were carried out in a total volume of 20 μL, and contained reaction buffer (20 mM Hepes, pH 6.5, 100 mM NaCl, 10 mM $MgCl_2$ and 1 mM $MnCl_2$) and end-labeled oligonucleotide substrate (10–30 fmol). The substrate/buffer mix was incubated for 20 min at 37° C. with Uve1p. In the case of G-Uve1p and GΔ228-Uve1p, crude cell lysates (5 μg of protein) were used for all assays. Fifty ng of affinity-purified GΔ228-Uve1p (0.75 pmol) and Δ228-Uve1p (1.2 pmol) were incubated with all of the UV-induced photoproducts. For all other assays 2 μg of affinity-purified GΔ228-Uve1p (30 pmol) and Δ228-Uve1p (48 pmol) were incubated with the substrates. Two μg of affinity-purified recombinant GST (72 pmol) was incubated with each substrate under Δ228-Uve1p optimum reaction conditions to control for potential contaminating nuclease activities which may be present in the Uve1p preparations and to determine the specificity of the Uve1p cleavage reaction. DNA repair proteins (*E. coli* exonuclease III, *E. coli* endonucleases III and IV, *E. coli* uracil DNA glycosylase and *S. cerevisiae* endonuclease III-like glycosylase [Ntg]) specific for each oligonucleotide substrate were also incubated with these substrates under their individual optimum reaction conditions, as a means to determine the specific DNA cleavage sites of Uve1p. The reaction products were analyzed on 20% denaturing (7 M urea) polyacrylamide gels (DNA sequencing-type gels) as described previously [Doetsch et al. (1985) *Nucl. Acids Res.* 13:3285–3304]. The DNA bands corresponding to the cleaved and uncleaved substrate were analyzed and quantified by phosphorimager analysis (Molecular Dynamics Model 445SI) and autoradiography.

Example 7

Oligonucleotides Containing DNA Damage

The DNA damage-containing oligonucleotides used as substrates in this study are presented in Table 1A. The structure of each damaged lesion is presented in FIG. 1. The 30-mer cs-CPD-containing oligonucleotide (cs-CPD-30mer) was prepared as described previously [Smith, C. A. (1993) *J. Biol. Chem.* 268:11143–11151]. The 49-mer oligonucleotides containing a cs-CPD (cs-CPD-49mer), a ts I-CPD (tsI-CPD-49mer), a ts II-CPD (tsII-CPD-49mer), a 6-4PP (6-4PP-49mer) and a Dewar isomer (Dewar-49mer) were synthesized as described previously [Smith and Taylor (1993) *J. Biol. Chem.* 268:11143–11151]. The oligonucleotide containing a platinum-DNA GG diadduct (Pt-GG-32mer) and its complementary strand were prepared as previously described [Naser et al. (1988) *Biochemistry* 27:4357–4367]. The uracil-containing oligonucleotide (U-37mer), the undamaged oligonucleotides and the complementary strand oligonucleotides for all the substrates were synthesized by the Emory University Microchemical Facility. The DHU-containing oligonucleotide (DHU-37mer) was synthesized by Research Genetics (Birmingham, Ala.). The oligonucleotides containing inosine (I-31mer) and xanthine (Xn-31 mer) and their complementary strands were a gift from Dr. Yoke Wah Kow (Emory University, Atlanta, Ga.). The 8-oxoguanine-containing 37-mer (8-oxoG-37mer) was synthesized by National Biosciences Inc. (Plymouth, Minn.). Some oligonucleotide substrates were obtained from Operon, Inc., Alameda, Calif.

Labeled oligonucleotide substrates were prepared as follows: The cs-CPD-30mer, the 49mer UV photodamage-containing oligonucleotides and the Pt-GG-32mer were 5' end-labeled with [γ-$^{32}$P] ATP (Amersham, 3000 Ci/mmol) using polynucleotide kinase [Tabor, S. (1985) In: *Current Protocols in Molecular Biology*, Greene Publishing Associates and Wiley (Interscience), New York, N.Y.). The oligonucleotides U-37mer, DHU-37mer, I-31mer, Xn-31mer and 8-oxoG-37mer were 3' end-labeled using terminal transferase (Promega, Madison, Wis.) and [α$^{32}$P] ddATP (Amersham, 3000 Ci/mmol) [Tu and Cohen (1980) *Gene* 10:177–183]. The end-labeled oligonucleotides were annealed to the appropriate complementary strand, and end-labeled duplex oligonucleotides were gel-purified on a 20% non-denaturing polyacrylamide gel. The DNA was resuspended in dd$H_2O$ and stored at −20° C. The IDL or hairpin nature of the DNA substrates was also confirmed by monitoring DNA strand cleavage by purified *E. coli* endonuclease V, which cleaves the duplexes in a pattern specific for this enzyme [Yao and Kow (1994) supra; Yao and Kow (1996) *J. Biol. Chem.* 271:30672–30676].

The AP substrate was prepared as described hereinbelow. 5' end-labeled, duplex U-37mer (20–50 pmol) was incubated with uracil DNA glycosylase (UDG, 6 units) for 30 minutes at 37° C. in UDG buffer (30 mM Hepes-KOH, pH 7.5, 1 mM EDTA, and 50 mM NaCl) to generate the AP site-containing oligonucleotide (AP-37mer). The DNA was extracted with PCIA (phenol-chloroform-isoamylalcohol, 29:19:1, v/v/v)

equilibrated with HE buffer (10 mM Hepes-KOH pH 8.0, 2 mM EDTA) with 0.1% 8-hydroxyquinoline, and was evaluated for its AP site content by cleavage with 0.1 M piperidine at 90° C. for 20 minutes.

The CPD-30mer Uve1p substrate [see herein and Kaur et al. (1998) supra] containing a centrally embedded, cis-syn TT cyclobutane pyrimidine dimer was a gift from John-Stephen Taylor (St. Louis, Mo.). All other oligonucleotide substrates (Table 1) for mismatch endonuclease experiments were synthesized by Operon, Inc. (Alameda, Calif.) or IDT, Inc. (Coralville, Iowa). All oligonucleotides were gel-purified and subjected to DNA sequence analysis for sequence confirmation. Oligonucleotides were 5' end-labeled with polynucleotide kinase using 50 µCi [$\gamma$-$^{32}$P] ATP (Amersham, 3000 Ci/mmol) as previously described [Bowman et al. (1994) Nucl. Acids Res. 22:3026–3032]. 3' end-labeled oligonucleotides were prepared by incubating 10 pmol of the indicated oligonucleotide with 10 units of terminal deoxynucleotidyl transferase (TdT, Promega) and 50 µCI of [$\alpha$-$^{32}$P] ddATP (Amersham, 3000 Ci/mmol) as previously described [Bowman et al. (1994) supra].

Example 8

Establishment of Optimal Reaction Conditions

The optimal reaction conditions for UVDE cleavage of CPD-30mer were established by varying the NaCl concentration, divalent cation (MnCl$_2$, and MgCl$_2$) concentration, or by varying the pH of the reaction buffer in the reaction. The buffers (20 mM at the indicated pH range) were as follows: sodium citrate (pH 3–6), Hepes-KOH (pH 6.5–8), and sodium carbonate (pH 9–10.6). The optimum temperature required for enzyme activity was determined by pre-incubating the enzyme and the substrate in the reaction buffer at a specific temperature for 10 min prior to mixing UVDE and CPD-30mer. The reaction was stopped by phenol-chloroform-isoamyl alcohol extraction and the reaction products were analyzed on DNA sequencing gels as described above. From these experiments the following standard reaction conditions were established: 20 mM Hepes (pH 7.5), 100 mM NaCl, 10 mM MgCl$_2$, 1 mM MnCl$_2$, 30° C. or at 37° C. for 20 minutes.

Example 9

Kinetic Assays

Enzyme reactions were carried out with 5 nM Δ228-UVDE or 11.5 nM GST-Δ228-UVDE in 20 mM Hepes (pH 6.5) in 10 mM MgCl$_2$, 1 mM MnCl$_2$, 100 mM NaCl. 5' End labeled CPD-30mer concentrations were varied from 25–250 nM in a final reaction volume of 15 µL for 0–3 minutes at 37° C. Initial enzyme velocities ($V_i$) were measured for each substrate concentration as nM of product formed per second. The apparent $K_m$, $V_{max}$, and turnover number ($K_{cat}$) were determined from Lineweaver Burk plots of averaged data (±standard deviations) from three independent experiments.

Example 10

Analysis of Uve1p Mismatch Repair Activity

Reactions with GΔ228-Uve1p were carried out by incubating approximately 100 or 200 fmol of labeled oligonucleotide substrate with 100–150 ng of purified GΔ228-Uve1p in 20 mM Hepes (pH 6.5), 10 mM MgCl$_2$, 1 mM MnCl$_2$, and 150 mM NaCl for 15 or 20 minutes at 37° C. (10–20 µl final volume). Reactions with crude preparations of GFL-Uve1p were carried out with 20–30 µg of cell extract incubated with the appropriate substrate in 20 mM Hepes (pH 7.5), 100 mM NaCl, 10 mM MgCl$_2$ and 1 mM MnCl$_2$ at 37° C. for 20 minutes. The reaction products were processed by extracting with an equal volume of phenol-chloroform-isoamyl alcohol (25:24:1), ethanol-precipitation, resuspension and analysis on 20% denaturing (7 M urea) polyacrylamide (DNA sequencing) gels as previously described [Kaur et al. (1998) supra]. The DNA species corresponding to the uncleaved substrate and Uve1p-mediated DNA strand scission products were analyzed and quantified by phosphorimager analysis (Molecular Dynamics model 445SI) and/or autoradiography. Base specific chemical cleavage DNA sequencing reaction products were included in the gels as size markers.

Terminal analysis of the mismatch cleavage products was carried out as follows. GΔ228-Uve1p was incubated with 3' end-labeled *CX/AY-31 mer under standard reaction conditions at 37° C. for 20 minutes. The ethanol-precipitated reaction products were incubated with either 10 units of calf intestinal phosphatase (CIP, Promega, Madison Wis.) at 37° C. for 30 minutes or with 10 units of T4 polynucleotide kinase (PNK, New England Biolabs) and 50 pmol ATP as previously described [Bowman et al. (1994) supra]. The reaction products were analyzed on 20% denaturing polyacrylamide gels as described above for Uve1p activity assays. Differences in electrophoretic mobilities of kinase-treated versus untreated DNA strand scission products indicated the presence or absence of a pre-existing 5'-phosphoryl group [Bowman et al. (1994) supra].

3' terminal analysis of the mismatch cleavage products was carried out as follows. To determine the chemical nature of the 3' terminus of GSTΔ228-Uve1p-mediated DNA strand scission products, 5' end-labeled *CX/AY-31mer was incubated with GΔ228-Uve1p as described above. The ethanol-precipitated, resuspended reaction products were then treated with 10 units of TdT and ddATP as previously described [Bowman et al (1994) supra]. Samples were processed and analyzed on polyacrylamide gels as described above for 5' terminal analysis.

To determine the pH optimum for Uve1p-mediated mismatch cleavage, 100 fmol of 3' end-labeled *CX/AY-31mer was incubated with approximately 100 ng of GΔ228-Uve1p with 10 mM MgCl$_2$ and 1 mM MnCl$_2$ in 20 mM reaction buffer of different pH ranges (pH 3.0–10.6). The buffers were as follows: sodium citrate (pH 3.0–6.0), Hepes-KOH (pH 6.5–8.0), and sodium carbonate (pH 9.0–10.6). The reaction products were analyzed on a 20% denaturing polyacrylamide gel and the optimal pH was calculated as previously described for Uve1p cleavage of CPD-30mer [Kaur et al. (1998) supra].

For substrate competition assays, end-labeled *CX/AY-31mer was generated by annealing 3' end-labeled CX with unlabeled strand AY. Unlabeled non-specific (non-mismatch) competitor GX/CY-31 mer was made by annealing strand GX to strand CY resulting in a duplex oligonucleotide with a C/A base pair instead of a G/G mispair. CPD-30mer, a well-characterized substrate for Uve1p, was employed as an unlabeled, specific competitor. 3' end-labeled *CX/AY-31 mer (0.1 pmol) was incubated with 100 ng of purified GΔ228-Uve1p and increasing amounts (0.1–2.0 pmol) of either specific (CPD-30mer) or non-specific (GX/CY-31mer) competitor. The competition reactions were processed and analyzed on 20% denaturing gels as described above. The DNA species corresponding to the uncleaved

*GX/GY-31mer and the DNA strand scission products were quantified by phosphorimager analysis (Molecular Dynamics model 445SI).

Example 11

Mutation Frequencies Assayed by Canavanine Resistance

To determine sensitivity to L-canavanine, 10 ml of PMALU$^g$ was inoculated with 100 μl of the indicated saturated culture and grown to mid-log phase at 25° C. 200 cells were plated onto PMALU$^g$ plates with varying concentrations of L-canavanine sulfate (0, 0.075, 0.22, 0.75, 2.2, 7.5, 22, and 75 μg/ml) and incubated at 30° C. Colonies were counted after four days and viability was normalized against the 0 g/ml plate for each strain. Colony formation assays were conducted for each strain by plating 10$^7$ cells from saturated cultures onto PMALU$^g$ plates supplemented with 75 μg/ml L-canavanine sulfate. Colonies were counted after eight days incubation at 30° C. Mean mutation frequencies were calculated using the method of the median as described by Lea and Coulson (1943) *J Genet.* 49:264–284.

Example 12

Antibody Inhibition

The N-terminal glutathione-S-transferase tag was removed from GΔ228-Uve1p by thrombin cleavage, and Δ228-Uve1p was purified as described previously [Kaur et al. (1998) supra]. Rabbit polyclonal antibodies were raised using purified Δ228-Uve1p as immunogen. GΔ228-Uve1p was incubated with immune or pre-immune sera for 45 min. at 4° C. and then incubated with the indicated end-labeled duplex oligonucleotides for Uve1p assay as described above. The reaction products were analyzed as described above.

TABLE 1A

Damaged Oligonucleotide Substrates Used in This Study.
cis-syn cyclobutane pyrimidine dimers (cs-CPDs), trans-syn I CPD (tsI-CPD), trans-syn II CPD (tsII-CPD), (6-4) photoproducts 96-4PP), a Dewar isomer (Dewar), a platinum DNA diadduct (Pt-GG), uracil (U), dihydrouracil (DHU), abasic site (AP), inosine (I), xanthine (Xn) and 8-oxoguanine (8-oxoG).

| Substrate | Damaged oligonucleotide sequence 5' to 3' | Adduct | $^a$Opposite base(s). | SEQ ID NO.: |
|---|---|---|---|---|
| A: cs-CPD-30mer | CATGCCTGCACGAAT^TAAGCAATTCGTAAT | cs-CPD | AA | 13 |
| B: UD-30mer | CATGCCTGCACGAATTAAGCAATTCGTAAT | undamaged | AA | 14 |
| C: cs-CPD-49mer | AGCTACCATGCCTGCACGAAT^TAAGCAATTCGTAATCATGGTCATAGCT | cs-CPD | AA | 15 |
| D: tsI-CPD-49mer | " | tsI-CPD | AA | 16 |
| E: tsII-CPD-49mer | " | tsII-CPD | AA 17 | |
| F: 6-4PP-49mer | " | 6-4PP | AA | 18 |
| G: Dewar-49mer | " | Dewar | AA 19 | |
| H: Pt-GG-32mer | TCCCTCCTTCCTTCCG*G*CCCTCCTTCCCCTTC | Pt-GG | CC | 20 |
| I: U-37mer | CTTGGACTGGATGTCGGCACXAGCGGATACAGGAGCA | U | A/G | 21 |
| J: DHU-37mer | " | DHU | A/G | 22 |
| K: AP-37mer | " | AP | A/G | 23 |
| L: I-31mer | TGCAGGTCGACTXAGGAGGATCCCCGGGTAC | I | T/C | 24 |
| M: Xn-31mer | " | Xn | T/C | 25 |
| N: 8-oxoG-37mer | CTTGGACTGGATGTCGGCACXAGCGGATACAGGAGCA | 8-oxoG | A/T/G/C | 26 |

$^a$denotes the bases that are placed opposite to the lesions on the complementary DNA strand.
^, *, X represent a UV induced dimer between two adjacent thymines, a cisplatin induced diadduct between two adjacent guanines and position at which the adducts U, DHU, AP, I, Xn and 8-oxoG are incorporated into the oligonucleotide substrates, respectively.

TABLE 1B

Base Mismatch and CPD-Containing Oligonucleotides Used in This Study.

| Oligo Name | Sequence | Strand Designation | SEQ ID NO: |
|---|---|---|---|
| XY-31mer[1] | 5'GTACCCGGGGATCCTCCXAGTCGACCTGCA3' | GX, AX, TX, CX: X = G, A, T, C | 27 |
| | 3'CATGGGCCCCTAGGAGGYTCAGCTGGACGT5' | GY, AY, TY, CY: Y = G, A, T, C | |

TABLE 1B-continued

Base Mismatch and CPD-Containing Oligonucleotides Used in This Study.

| Oligo Name | Sequence | Strand Designation | SEQ ID NO: |
|---|---|---|---|
| CX/AY-41mer | 5'CGTTAGCATGCCTGCACGAACTAAGCAATTCGTAATGCATT3' | CX | 28 |
|  | 3'GCAATCGTACGGACGTGCTTAATTCGTTAAGCATTACGTAA5' | AY |  |
| C(6)/A-41mer[2] | 5'CGTTACAAGTCCGTCACGAATTAAGCAATTCGTAACGCATT3' | C(6) | 29 |
|  | 3'GCAATGTTCAGGCAGTGCTTAATTCGTTAAGCATTACGTAA5' | A(36) |  |
| C(11)/A-41mer | 5'CGTTACAAGTCCGTCACGAATTAAGCAATTCGTAACGCATT3' | C(11) | 30 |
|  | 3'GCAATGTTCAGGCAGTGCTTAATTCGTTAAACATTGCGTAA5' | A(31) |  |
| C(16)/A-41mer | 5'CGTTACAAGTCCGTCACGAATTAAGCAATTCGTAACGCATT3' | C(16) | 31 |
|  | 3'GCAATGTTCAGGCAGTGCTTAATTCATTAAGCATTGCGTAA5' | A(26) |  |
| C(22)/A-41mer | 5'CGTTACAAGTCCGTCACGACTTAAGCAATTCGTAACGCATT3' | C(22) | 32 |
|  | 3'GCAATGTTCAGGCAGTGCTAAATTCGTTAAGCATTGCGTAA5' | A(20) |  |
| C(27)/A-41mer | 5'CGTTACAAGTCCGTCACGAATTAAGCAATTCGTAACGCATT3' | C(27) | 33 |
|  | 3'GCAATGTTCAGGCAATGCTTAATTCGTTAAGCATTGCGTAA5' | A(15) |  |
| C(32)/A-41mer | 5'CGTTACAAGCCCGTCACGAATTAAGCAATTCGTAACGCATT3' | C(32) | 34 |
|  | 3'GCAATGTTCAGGCAGTGCTTAATTCGTTAAGCATTGCGTAA5' | A(10) |  |
| C(37)/A-41mer | 5'CGTTCCAAGTCCGTCACGAATTAAGCAATTCGTAACGCATT3' | C(37) | 35 |
|  | 3'GCAAAGTTCAGGCAGTGCTTAATTCGTTAAGCATTGCGTAA5' | A(5) |  |
| CPD-30mer[3] | 5'CATGCCTGCACGAAT^TAAGCAATTCGTAAT3' | 30 D | 13 |
|  | 3'GTACGGACGTGCTTA ATTCGTTAAGCATTA5' | 30 C |  |

[1]Series of 16 different duplex oligos containing all possible base pair/mispair combinations between G, A, T, and C.
In text, * denotes labeled strand (e.g. *CX/AY-31mer corresponds to C/A mismatch with the C-containing X strand as the labeled strand).
[2]C/A mismatch oligos designated by base position of the mismatched C from the 3' terminus.
[3]CPD-30mer contains a cyclobutane pyrimidine dimer designated as T^T.

TABLE 2

Activity of Uvelp on Oligonucleotide Substrates Containing Uracil, Dihydrouracil and AP sites

| Protein | U/G | U/A | DHU/G | DHU/A | AP/G | AP/A |
|---|---|---|---|---|---|---|
| [a]Positive control | 90–100 | 50–60 | 70–80 | 15–20 | 90–100 | 90–100 |
| GΔ228-Uvelp | 8–12 | 1–5 | 37–42 | 10–15 | 90–100 | 90–100 |
| GST | 1–5 | 1–5 | 1–5 | 1–5 | 1–5 | 1–5 |

The percent of substrate converted into total DNA cleavage products formed when the DNA damage lesion is base paired with a G or an A in the complementary strand. Details of experiments are outlined in Example 10.
[a]Positive control: when analyzing U 37mer, uracil DNA glycosylase (UDG) was used as a positive control; for assays involving DHU 37mer, the S. cerevisiae endonuclease III-like homolog Ntg1 was used as a positive control; E. coli endonuclease IV was used as a positive control for AP endonuclease activity.

TABLE 3

Uvelp Cleavage Efficiency on Different Substrates.

| Substrate | Percent[Cleavage] |
|---|---|
| cs-CPD 49mer | 89 |
| tsI-CPD 49mer | 75 |
| tsII-CPD 49mer | 75 |
| 6-4PP 49mer | 71 |
| Dewar | 83 |
| AP 37mer | 12.5 |
| DHU 37mer | 3 |
| Pt-GG 32mer | 2.5 |
| U 37mer | 1 |
| 8-oxoG 37mer | 0 |
| I 31mer | 0 |
| Xn 31mer | 0 |

[a]The percent cleavage was calculated by quantifying the amount of Uvelp-mediated cleavage product formed when 300 ng of affinity-purified GΔ228-Uvelp was incubated with ~150 fmol of each substrate.

TABLE 4

Spontaneous Mutation Rates of uve1 and pms1 Null Mutants

| Genotype | Distribution of canavanine-resistant colonies/plate | | | | Median no. of colonies/$10^7$ cells | Calculated mutation frequency (mean ± SE) |
|---|---|---|---|---|---|---|
| | 0–2 | 3–34 | 35–86 | >86 | | |
| Wild type | 18 | 16 | 2 | 0 | 2.5 | $1.5 \times 10^{-7} \pm 2.5 \times 10^{-8}$ |
| uve1::ura4+ | 4 | 14 | 8 | 10 | 34.5 | $9.7 \times 10^{-7} \pm 4.2 \times 10^{-8}$ |
| pms1::ura4+ | 0 | 8 | 10 | 18 | 86.5 | $2.0 \times 10^{-6} \pm 5.0 \times 10^{-8}$ |

TABLE 5

Nucleotide Sequence Encoding GST-Full-length UVDE
(SEQ ID NO:1)

```
   1 atgaccaagt tacctatact aggttattgg aaaaattaag ggccttgtgc
  51 aacccactcg acttcttttg gaatatcttg aagaaaaata tgaagagcat
 101 ttgtatgagc gcgatgaagg tgataaatgg cgaaacaaaa agtttgaatt
 151 gggtttggag tttcccaatc ttccttatta tattgatggt gatgttaaat
 201 taacacagtc tatggccatc atacgttata tagctgacaa gcacaacatg
 251 ttggttggtt gtccaaaaga gcgtgcagag atttcaatgc ttgaaggagc
 301 ggttttggat attagatacg gtgtttcgag aattgcatat agtaaagact
 351 ttgaaactct caaagttgat tttcttagca agctacctga aatgctgaaa
 401 atgttcgaag atcgtttatg tcataaaaca tatttaaatg ttgaccatgt
 451 aacccatcct gacttcatgt tgtatgacgc tcttgatgtt gttttataca
 501 tggacccaat gtgcctggat gcgttcccaa aattagtttg ttttaaaaaa
 551 cgtattgaag ctatcccaca aattgataag tacttgaaat ccagcaagta
 601 tatagcatgg cctttgcagg gctggcaagc cacgtttggt ggtggcgacc
 651 atcctccaaa atcggatcat ctggttccgc gtggatccat gcttaggcta
 701 ttgaaacgaa atattcaaat ctctaaacgc attgttttca ccatattaaa
 751 acaaaaggca tttaaaggta atcatccttg tgtaccgtcg gtttgtacca
 801 ttacttactc tcgttttcat tgtttacccg atacccttaa aagtttactt
 851 ccaatgagct caaaaaccac actctcaatg ttaccgcaag ttaatatcgg
 901 tgcgaattca ttctctgccg aaacaccagt cgacttaaaa aaagaaaatg
 951 agactgagtt agctaatatc agtggacctc acaaaaaaag tacttctacg
1001 tctacacgaa agagggcacg tagcagtaaa aagaaagcga cagattctgt
1051 ttccgataaa attgatgagt ctgttgcgtc ctatgattct tcaactcatc
1101 ttaggcgatc gtcgagatca aaaaaaccgg tcaactacaa ttcctcgtca
1151 gaatccgaat cggaggagca aattagtaaa gctactaaaa aagttaaaca
1201 aaaagaggaa gaggagtatg ttgaagaagt cgacgaaaag tctcttaaaa
1251 atgaaagtag ctctgacgag ttcgaaccgg ttgtgccgga acagttggaa
1301 actccaattt ctaaacgaag acggtctcgt tcttctgcaa aaaatttaga
1351 aaaagaatct acaatgaatc ttgatgatca tgctccacga gagatgtttg
1401 attgtttgga caaacccata ccctggcgag gacgattggg gtatgcttgt
1451 ttgaatacta ttttaaggtc aatgaaggag agggtttttt gttcacgcac
```

TABLE 5-continued

```
1501 ctgccgaatt acaaccattc aacgtgatgg gctcgaaagt gtcaagcagc
1551 taggtacgca aaatgtttta gatttaatca aattggttga gtggaatcac
1601 aactttggca ttcacttcat gagagtgagt tctgatttat ttcctttcgc
1651 aagccatgca aagtatggat ataccttga atttgcacaa tctcatctcg
1701 aggaggtggg caagctggca aataaatata atcatcgatt gactatgcat
1751 cctggtcagt acacccagat agcctctcca cgagaagtcg tagttgattc
1801 ggcaatacgt gatttggctt atcatgatga aattctcagt cgtatgaagt
1851 tgaatgaaca attaaataaa gacgctgttt aattattca ccttggtggt
1901 acctttgaag gaaaaaaaga aacactggat aggtttcgta aaaattatca
1951 acgcttgtct gattcggtta aagctcgttt agttttagaa aacgatgatg
2001 tttcttggtc agttcaagat ttattacctt tatgccaaga acttaatatt
2051 cctctagttt tggattggca tcatcacaac atagtgccag aacgcttcg
2101 tgaaggaagt ttagatttaa tgccattaat cccaactatt cgagaaacct
2151 ggacaagaaa gggaattaca cagaagcaac attactcaga atcggctgat
2201 ccaacggcga tttctgggat gaaacgacgt gctcactctg ataggtgtt
2251 tgactttcca ccgtgtgatc ctacaatgga tctaatgata gaagctaagg
2301 aaaaggaaca ggctgtattt gaattgtgta gacgttatga gttacaaaat
2351 ccaccatgtc ctcttgaaat tatggggcct gaatacgatc aaactcgaga
2401 tggatattat ccgcccggag ctgaaaagcg tttaactgca agaaaaaggc
2451 gtagtagaaa agaagaagta gaagaggatg aaaaataaaa at
```

TABLE 6

Deduced Amino Acid Sequences of GST-Full-length UVDE
(SEQ ID NO:2)

```
  1 mtklpilgyw kikglvqptr llleyleeky eehlyerdeg dkwrnkkfel
 51 glefpnlpyy idgdvkltqs maiiryiadk hnmlggcpke raeismlega
101 vldirygvsr iayskdfetl kvdflsklpe mlkmfedrlc hktylngdhv
151 thpdfmlyda ldvvlymdpm cldafpklvc fkkrieaipq idkylkssky
201 iawplqgwqa tfgggdhppk sdhlvprgsm lrllkrniqi skrivftilk
251 qkafkgnhpc vpsvctitys rfhclpdtlk sllpmssktt lsmlpqvnig
301 ansfsaetpv dlkkenetel anisgphkks tststrkrar sskkkatdsv
351 sdkidesvas ydssthlrrs srskkpvnyn ssseseseeq iskatkkvkq
401 keeeyveev dekslkness sdefepvvpe qletpiskrr rsrssaknle
451 kestmnlddh apremfdcld kpipwrgrlg yaclntilrs mkervfcsrt
501 crittiqrdg lesvkqlgtq nvldliklve wnhnfgihfm rvssdlfpfa
551 shakygytle faqshleevg klankynhrl tmhpgqytqi asprevvvds
601 airdlayhde ilsrmklneq lnkdavliih lggtfegkke tldrfrknyq
651 rlsdsvkarl vlendvsws vqdllplcqe lniplvldwh hhnivpqtlr
701 egsldlmpli ptiretwtrk gitqkqhyse sadptaisgm krrahsdrvf
```

TABLE 6-continued

```
751 dfppcdptmd lmieakekeq avfelcrrye lqnppcplei mgpeydqtrd 801 gyyppgaekr ltarkrrsrk eeveedek
```

TABLE 7

Nucleotide Sequence Encoding Δ228-UVDE (SEQ ID NO:3)

```
   1 gatgatcatg ctccacgaga gatgtttgat tgtttggaca aacccatacc
  51 ctggcgagga cgattggggt atgcttgttt gaatactatt ttaaggtcaa
 101 tgaaggagag ggttttttgt tcacgcacct gccgaattac aaccattcaa
 151 cgtgatgggc tcgaaagtgt caagcagcta ggtacgcaaa atgttttaga
 201 tttaatcaaa ttggttgagt ggaatcacaa ctttggcatt cacttcatga
 251 gagtgagttc tgatttattt cctttcgcaa gccatgcaaa gtatggatat
 301 acccttgaat tgcacaatc tcatctcgag gaggtgggca agctggcaaa
 351 taaatataat catcgattga ctatgcatcc tggtcagtac acccagatag
 401 cctctccacg agaagtcgta gttgattcgg caatacgtga tttggcttat
 451 catgatgaaa ttctcagtcg tatgaagttg aatgaacaat aaataaaga
 501 cgctgtttta attattcacc ttggtggtac ctttgaagga aaaaaagaaa
 551 cattggatag gtttcgtaaa aattatcaac gcttgtctga ttcggttaaa
 601 gctcgtttag ttttagaaaa cgatgatgtt tcttggtcag ttcaagattt
 651 attaccttta tgccaagaac ttaatattcc tctagtttg gattggcatc
 701 atcacaacat agtgccagga acgcttcgtg aaggaagttt agatttaatg
 751 ccattaatcc caactattcg agaaacctgg acaagaaagg gaattacaca
 801 gaagcaacat tactcagaat cggctgatcc aacggcgatt tctgggatga
 851 aacgacgtgc tcactctgat agggtgtttg actttccacc gtgtgatcct
 901 acaatggatc taatgataga agctaaggaa aaggaacagg ctgtatttga
 951 attgtgtaga cgttatgagt tacaaaatcc accatgtcct cttgaaatta
1001 tggggcctga atacgatcaa actcgagatg gatattatcc gcccggagct
1051 gaaaagcgtt taactgcaag aaaaaggcgt agtagaaaag aagaagtaga
1101 agaggatgaa aaataaaaat ccgtcatact tttgattta tggcataatt
1151 tagccatctc c
```

TABLE 8

Deduced Amino Acid Sequence of Δ228-UVDE (SEQ ID NO:4)

```
   1 ddhapremfd cldkpipwrg rlgyaclnti lrsmkervfc srtcrittiq
  51 rdglesvkql gtqnvldlik lvewnhnfgi hfmrvssdlf pfashakygy
 101 tlefaqshle evgklankyn hrltmhpgqy tqiasprevv vdsairdlay
 151 hdeilsrmkl neqlnkdavl iihlggtfeg kketldrfrk nyqrlsdsvk
 201 arlvlenddv swsvqdllpl cqelniplvl dwhhhnivpg tlregsldlm
 251 pliptiretw trkgitqkqh ysesadptai sgmkrrahsd rvfdfppcdp
```

TABLE 8-continued

```
301 tmdlmieake keqavfelcr ryelqnppcp leimgpeydq trdgyyppga 351 ekrltarkrr srkeeveede k
```

TABLE 9

Nucleotide Sequence Encoding GST-Δ228-UVDE (SEQ ID NO:5)

```
   1 atgaccaagt tacctatact aggttattgg aaaaattaag ggccttgtgc
  51 aacccactcg acttcttttg gaatatcttg aagaaaaata tgaagagcat
 101 ttgtatgagc gcgatgaagg tgataaatgg cgaaacaaaa agtttgaatt
 151 gggtttggag tttcccaatc ttccttatta tattgatggt gatgttaaat
 201 taacacagtc tatggccatc atacgttata tagctgacaa gcacaacatg
 251 ttggttggtt gtccaaaaga gcgtgcagag atttcaatgc ttgaaggagc
 301 ggttttggat attagatacg gtgtttcgag aattgcatat agtaaagact
 351 ttgaaactct caagttgat tttcttagca agctacctga aatgctgaaa
 401 atgttcgaag atcgtttatg tcataaaaca tatttaaatg ttgaccatgt
 451 aacccatcct gacttcatgt tgtatgacgc tcttgatgtt gttttataca
 501 tggacccaat gtgcctggat gcgttcccaa aattagtttg tttttaaaaaa
 551 cgtattgaag ctatcccaca aattgataag tacttgaaat ccagcaagta
 601 tatagcatgg cctttgcagg gctggcaagc cacgtttggt ggtggcgacc
 651 atcctccaaa atcggatcat ctggttccgc gtggatccga tgatcatgct
 701 ccacgagaga tgtttgattg ttcggacaaa cccatacct ggcgaggacg
 751 attggggtat gcttgtttga atactatttt aaggtcaatg aaggagaggg
 801 ttttttgttc acgcacctgc cgaattacaa ccattcaacg tgatgggctc
 851 gaaagtgtca agcagctagg tacgcaaaat gttttagatt taatcaaatt
 901 ggttgagtgg aatcacaact ttggcattca cttcatgaga gtgagttctg
 951 atttatttcc tttcgcaagc catgcaaagt atggatatac ccttgaattt
1001 gcacaatctc atctcgagga ggtgggcaag ctggcaaata aatataatca
1051 tcgattgact atgcatcctg gtcagtacac ccagatagcc tctccacgag
1101 aagtcgtagt tgattcggca atacgtgatt tggcttatca tgatgaaatt
1151 ctcagtcgta tgaagttgaa tgaacaatta ataaagacg ctgttttaat
1201 tattcacctt ggtggtacct tgaaggaaa aaaagaaaca ttggataggt
1251 ttcgtaaaaa ttatcaacgc ttgtctgatt cggttaaagc tcgtttagtt
1301 ttagaaaacg atgatgtttc ttggtcagtt caagatttat tacctttatg
1351 ccaagaactt aatattcctc tagttttgga ttggcatcat cacaacatag
1401 tgccaggaac gcttcgtgaa ggaagtttag atttaatgcc attaatccca
1451 actattcgag aaacctggac aagaaaggga attacacaga agcaacatta
1501 ctcagaatcg gctgatccaa cggcgatttc tgggatgaaa cgacgtgctc
1551 actctgatag ggtgtttgac tttccaccgt gtgatcctac aatggatcta
1601 atgatagaag ctaaggaaaa ggaacaggct gtatttgaat gtgtgtagacg
1651 ttatgagtta caaaatccac catgtcctct tgaaattatg gggcctgaat
```

TABLE 9-continued

```
1701 acgatcaaac tcgagatgga tattatccgc ccggagctga aaagcgttta 1751 actgcaagaa aaaggcgtag tagaaaagaa gaagtagaag aggatgaaaa 1801 ataaggatcc c
```

TABLE 10

Deduced Amino Acid Sequence of GST-Δ228-UVDE (SEQ ID NO:6)

```
  1 mtklpilgyw kikglvqptr llleyleeky eehlyerdeg dkwrnkkfel
 51 glefpnlpyy idgdvkltqs maiiryiadk hnmlggcpke raeismlega
101 vldirygvsr iayskdfetl kvdflsklpe mlkmfedrlc hktylngdhv
151 thpdfmlyda ldvvlymdpm cldafpklvc fkkrieaipq idkylkssky
201 iawplqgwqa tfgggdhppk sdhlvprgsd dhapremfdc ldkpipwrgr
251 lgyaclntil rsmkervfcs rtcrittiqr dglesvkqlg tqnvldlikl
301 vewnhnfgih fmrvssdlfp fashakygyt lefaqshlee vgklankynh
351 rltmhpgqyt qiasprevvv dsairdlayh deilsrmkln eqlnkdavli
401 ihlggtfegk ketldrfrkn yqrlsdsvka rlvlenddvs wsvqdllplc
451 qelniplvld whhhnivpgt lregsldlmp liptiretwt rkgitqkqhy
501 sesadptais gmkrrahsdr vfdfppcdpt mdlmieakek eqavfelcrr
551 yelqnppcpl eimgpeydqt rdgyyppgae krltarkrrs rkeeveedek
```

TABLE 11

Nucleotide Sequence Encoding the GST Leader Sequence
(SEQ ID NO:7)

```
  1 atgaccaagt tacctatact aggttattgg aaaaattaag ggccttgtgc
 51 aacccactcg acttcttttg gaatatcttg aagaaaaata tgaagagcat
101 ttgtatgagc gcgatgaagg tgataaatgg cgaaacaaaa agtttgaatt
151 gggtttggag tttcccaatc ttccttatta tattgatggt gatgttaaat
201 taacacagtc tatggccatc atacgttata gctgacaa gcacaacatg
251 ttggttggtt gtccaaaaga gcgtgcagag atttcaatgc ttgaaggagc
301 ggttttggat attagatacg gtgtttcgag aattgcatat agtaaagact
351 ttgaaactct caaagttgat tttcttagca agctacctga atgctgaaa
401 atgttcgaag atcgtttatg tcataaaaca tatttaaatg ttgaccatgt
451 aacccatcct gacttcatgt tgtatgacgc tcttgatgtt gtttatacac
501 tggacccaat gtgcctggat gcgttcccaa aattagtttg ttttaaaaaa
551 cgtattgaag ctatcccaca aattgataag tacttgaaat ccagcaagta
601 tatagcatgg ccttttcagg gctggcaagc cacgtttggt ggtggcgacc
651 atcctccaaa atcggatcat ctggttccgc gtggatcc
```

TABLE 12

Deduced Amino Acid Sequence of the GST Leader Polypeptide
(SEQ ID NO:8)

```
  1 MTKLPILGYW KIKGLVQPTR LLLEYLEEKY EEHLYERDEG DKWRNKKFEL
 51 GLEFPNLPYY IDGDVKLTQS MAIIRYIADK HNMLGGCPKE RAEISMLEGA
101 VLDIRYGVSR IAYSKDFETL KVDFLSKLPE MLKMFEDRLC HKTYLNGDHV
151 THPDFMLYDA LDVVLYMDPM CLDAFPKLVC FKKRIEAIPQ IDKYLSSKY
201 IAWPLQGWQA TFGGGDHPPK SDHLVPRGS
```

TABLE 13

*Neurospora crassa* UVDE Homolog (Genbank Accession No. BAA-74539)
(SEQ ID NO:36)

mpsrkskaaaldtpqsesstfsstldssapsparnlrrsgrnilqpssekdrdhekrsgeelagrmmgkda nghclregkeqeegvkmaieglarmerrlqratkrqkkqleedgipvpsvvsrfptapyhhkstnaeere akepvlkthskdvereaeigvddvvkmepaatniiepedaqdaaergaarppavnssylplpwkgrlg yacIntylrnskppifssrtcrmasivdhrhplqfedepehhlknkpdkskepqdelghkfvqelglanar divkmlcwnekygirflrlssemfpfashpvhgyklapfasevlaeagrvaaelghrltthpgqftqlgsp rkevvesairdleyhdellsllklpeqqnrdavmiihmggqfgdkaatlerfkrnyarlsqscknrlvlend dvgwtvhdllpvceelnipmvldyhhhnicfdpahlregtldisdpklqeriantwkrkgikqkmhyse pcdgavtprhrrkhrprvmtlppcppdmdlmieakdkeqavfelmrtfklpgfekindmvpydrdde nrpappvkapkkkggkrkrttdeeaaepeevdtaaddvkdapegpkevpeeeramggpynrvyw plgceewlkpkkrevkkgkvpeevedegefdg

TABLE 14

*Bacillus subtilis* UVDE Homolog (Genbank Accession No. Z 49782)
(SEQ ID NO:37)

mifrfgfvsnamslwdaspaktltfarysklskterkealltvtkanlrntmrtlhyiighgiplyrfsssivpl athpdvmwdfvtpfqkefreigelvkthqlrtsfhpnqftlftspkesvtknavtdmayhyrmleamgia drsvinihiggaygnkdtataqfhqnikqlpqeikermtlenddktytteetlqvceqedvpfvfdhfhhfy anpddhadlnvalprmiktwerciglqpkvhlsspkseqairshadyvdanfllpllerfrqwgtnidfmie akqkdkallrlmdelssirgvkrigggalqwks

TABLE 15

Human UVDE Homolog (Genbank Accession No. AF 114784.1)
(SEQ ID NO:38)

```
  1 mgttglesls lgdrgaaptv tsserlvpdp pndlrkedva melervgede eqmmikrsse
 61 cnpllqepia saqfgatagt ecrksvpcgw ervvkqrlfg ktagrfdvyf ispqglkfrs
121 ksslanylhk ngetslkped fdftvlskrg iksrykdcsm aaltshlqnq snnsnwnlrt
181 rskckkdvfm ppsssselqe srglsnftst hlllkedegv ddvnfrkvrk pkgkvtilkg
241 ipikktkkgc rkscsgfvqs dskresvcnk adaesepvaq ksqldrtvci sdagacgetl
301 svtseenslv kkkerslssg snfcseqkts giinkfcsak dsehnekyed tfleseeigt
361 kvevverkeh lhtdilkrgs emdnncsptr kdftgekifq edtiprtqie rrktslyfss
```

TABLE 15-continued

```
421 kynkealspp rrkafkkwtp prspfnivqe tlfhdpwkll iatiflnrts gkmaipvlwk
481 flekypsaev artadwrdvs ellkplglyd lraktivkfs deyltkqwky pielhgigky
541 gndsyrifcv newkqvhped hklnkyhdwl wenheklsls
```

TABLE 16

D. radiodurans UVDE Homolog (SEQ ID NO:39)

```
  1 QLGLVCLTVG PEVRFRTVTL SRYRALSPAE REAKLLDLYS SNIKTLRGAA
 51 DYCAAHDIRL YRLSSSLFPM LDLAGDDTGA AVLTHLAPQL LEAGHAFTDA
101 GVRLLMHPEQ FIVLNSDRPE VRESSVRAMS AHARVMDGLG LARTPWNLLL
151 LHGGKGGRGA ELAALIPDLP DPVRLRLGLE NDERAYSPAE LLPICEATGT
201 PLVFDAHHHV VHDKLPDQED PSVREWVLRA RATWQPPEWQ VVHLSNGIEG
251 PQDRRHSHLI ADFPSAYADV PWIEVEAKGK EEAIAALRLM APFK
```

Tables 17A–17B: Potential IDL substrates for Uve1p. Sequences of the oligonucleotide strands utilized to generate the heteroduplex substrates used in this study. Names of individual oligonucleotide strands are indicated beside each duplex. Two different sequence types (I and Lo) were used.

TABLE 17A

Duplex type ID substrates containing IDL loops of 0, 2, 4, 6, 8 and 16 nt in length.

| | Strand | SEQ ID NO |
|---|---|---|
| 5' CACAGACTCCCTCTGTCATAGGTTTGAGTTTATATGGAA 3' | IX | 40 |
| 3' GTGTCTGAGGGAGACAGTATCCAAACTCAAATATACCTT 5' | D0 | 41 |
| 5' CACAGACTCCCTCTGTCATAGGTTCATGAGTTTATATGGAA 3' | ID2 | 42 |
| 3' GTGTCTGAGGGAGACAGTATCCAA--ACTCAAATATACCTT 5' | D0 | 41 |
| 5' CACAGACTCCCTCTGTCATAGGTTCACATGAGTTTATATGGAA 3' | ID4 | 43 |
| 3' GTGTCTGAGGGAGACAGTATCCAA----ACTCAAATATACCTT 5' | D0 | 41 |
| 5' CACAGACTCCCTCTGTCATAGGTTCACACATGAGTTTATATGGAA 3' | ID6 | 44 |
| 3' GTGTCTGAGGGAGACAGTATCCAA------ACTCAAATATACCTT 5' | D0 | 41 |
| 5' CACAGACTCCCTCTGTCATAGGTTCACACACATGAGTTTATATGGAA 3' | ID8 | 45 |
| 3' GTGTCTGAGGGAGACAGTATCCAA--------ACTCAAATATACCTT 5' | D0 | 41 |
| 5' CACAGACTCCCTCTGTCATAGGTTGAGTACTAGTACTCTGAGTTTATATGGAA 3' | HP8 | 46 |
| 3' GTGTCTGAGGGAGACAGTATCCAAACTCAAATATACCTT 5' | D0 | 41 |

TABLE 17B

Duplex type LD substrates containing IDL loops of 0, 2, 4, 6 and 8 nt in length.

| | Strand | SEQ ID NO |
|---|---|---|
| 5'-CGTTAGAACTCCGTCACGAATTAAGCAATTAGTAATGCATT 3' | Lo0 | 47 |
| 3'-GCAATCTTGAGGCAGTGCTTAATTCGTTAATCATTACGTAA 5' | Bot | 48 |
| 5'-CGTTAGAACTCCGTCACGAATTAAGCAATTCAAGTAATGCATT 3' | Lo2 | 49 |

TABLE 17B-continued

Duplex type LD substrates containing IDL loops of 0, 2, 4, 6 and 8 nt in length.

| | Strand | SEQ ID NO |
|---|---|---|
| 3'-GCAATCTTGAGGCAGTGCTTAATTCGTTAA--TCATTACGTAA 5' | Bot | 48 |
| 5'-CGTTAGAACTCCGTCACGAATTAAGCAATTCACAAGTAATGCATT 3' | Lo4 | 50 |
| 3'-GCAATCTTGAGGCAGTGCTTAATTCGTTAA----TCATTACGTAA 5' | Bot | 48 |
| 5'-CGTTAGAACTCCGTCACGAATTAAGCAATTCACACAAGTAATGCATT 3' | Lo6 | 51 |
| 3'-GCAATCTTGAGGCAGTGCTTAATTCGTTAA------=TCATTACGTAA 5' | Bot | 48 |
| 5'-CGTTAGAACTCCGTCACGAATTAAGCAATTCACACACAAGTAATGCATT 3' | Lo8 | 52 |
| 3'-GCAATCTTGAGGCAGTGCTTAATTCGTTAA--------TCATTACGTAA 5' | Bot | 48 |

TABLE 18

Sequences of oligonucleotides used in strand specificity experiments.

1  5'-CGTTACAAGTCCGTCACGAATTAAGCAATTCGTAACGCATT-3'  C6, SEQ ID NO:53
   3'-GCAATGTTCAGGCAGTGCTTAATTCGTTAAGCATTACGTAA-5'  A36, SEQ ID NO:54
   5-AATGCATTACGAATTGCTTAATTCGTGACGGACTTGTAACG*

2  5'-CGTTACAAGTCCGTCACGAATTAAGCAATTCGTAACGCATT-3'  C11, SEQ ID NO:55
   3'-GCAATGTTCAGGCAGTGCTTAATTCGTTAAACATTGCGTAA-5'  A31, SEQ ID NO:56
      AATGCGTTACAAATTGCTTAATTCGTGACGGACTTGTAACG*

3  5'-CGTTACAAGTCCGTCACGAATTAAGCAATTCGTAACGCATT-3'  C16, SEQ ID NO:57
   3'-GCAATGTTCAGGCAGTGCTTAATTCATTAAGCATTGCGTAA-5'  A26, SEQ ID NO:58
      AATGCGTTACGAATTACTTAATTCGTGACGGACTTGTAACG*

4  5'-CGTTACAAGTCCGTCACGACTTAAGCAATTCGTAACGCATT-3'  C22, SEQ ID NO:59
   3'-GCAATGTTCAGGCAGTGCTAAATTCGTTAAGCATTGCGTAA-5'  A20, SEQ ID NO:60
      AATGCGTTACGAATTGCTTAAATCGTGACGGACTTGTAACG*

5  5'-CGTTACAAGTCCGTCACGAATTAAGCAATTCGTAACGCATT-3'  C27, SEQ ID NO:61
   3'-GCAATGTTCAGGCAATGCTTAATTCGTTAAGCATTGCGTAA-5'  A15, SEQ ID NO:62
      AATGCGTTACGAATTGCTTAATTCGTAACGGACTTGTAACG*

6  5'-CGTTACAAGCCCGTCACGAATTAAGCAATTCGTAACGCATT-3'  C32, SEQ ID NO:63
   3'-GCAATGTTCAGGCAGTGCTTAATTCGTTAAGCATTGCGTAA-5'  A10 SEQ ID NO:64
      AATGCGTTACGAATTGCTTAATTCGTGACGACTTGTAACG*

7  5'-CGTTCCAAGTCCGTCACGAATTAAGCAATTCGTAACGCATT-3'  C37 SEQ ID NO:65
   3'-GCAAAGTTCAGGCAGTGCTTAATTCGTTAAGCATTGCGTAA-5'  A5 SEQ ID NO:66
      AATGCGTTACGAATTGCTTAATTCGTGACGGACTTGAAACG*

Duplex AB

5'-TGCACGGACCTCGAGAGAACCGAACGATCCGGATGTGATCATGGGACAGAATTCGCACACTGCACTCGACG (STRAND A, SEQ ID NO:67)
   ATAGTCT-3'

TABLE 18-continued

Sequences of oligonucleotides used in strand specificity experiments.

3'-TCTTGGCTTGCTAGGCCTACACTACTACCCTGTCTTAAGCGTGTGACGT-5' (STRAND B, SEQ ID NO:68)

TGCAGTGTGCGAATTCTGTCCCATCATCACATCCGGATCGTTCGGTTCT*

Duplex AC

5'-TGCACGGACCTCGAGAGAACCGAACGATCCGGATGTGATCATGGGACAGAATTCGCACACTGCACTGCAC (STRAND A, SEQ ID NO:67)
    GATAGTCT-3'

3'-TCTTGGCTTGCTAGGCCTACACTACTACCCTGTCTTAAGCGTGTGACGTGACGTGCTATCAG-5' (STRAND C, SEQ ID NO:69)

GACTATCGTGCAGTGCAGTGTGCGAATTCTGTCCCATCATCACATCCGGATCGTTCGGTTCT*

Duplex AD

5'-TGCACGGACCTCGAGAGAACCGAACGATCCGGATGTGATCATGGGACAGAATTCGCACACTGCACTGCAC (STRAND A, SEQ ID NO:67)
    GATAGTCT

3'-ACGTGCCTGGAGCTCTCTTGGCTTGCTAGGCCTACACTACTACCCTGTCTTAAGCGTGTGACGT-5' (STRAND D, SEQ ID NO:70)

TGCAGTGTGCGAATTCTGTCCCATCATCACATCCGGATCGTTCGGTTCTCTCGAGGTCCGTGCA*

Duplex AE

5'-TGCACGGACCTCGAGAGAACCGAACGATCCGGATGTGATCATGGGACAGAATTCGCACACTGCACTGCACG (STRAND A, SEQ ID NO:67)
    ATAGTCT-3'

3'-ACGTGCCTGGAGCTCTCTTGGCTTGCTAGGCCTACACTACTACCCTGTCTTAAGCGTGTGACGTGAC (strand E, SEQ ID NO:71)
    GTGCTATCAGAG-5'

GAGACTATCGTGCAGTGCAGTGTGCGAATTCTGTCCCATCATCACATCCGGATCGTTCGGTTCTCTCGAGGT
CCGTGCA*

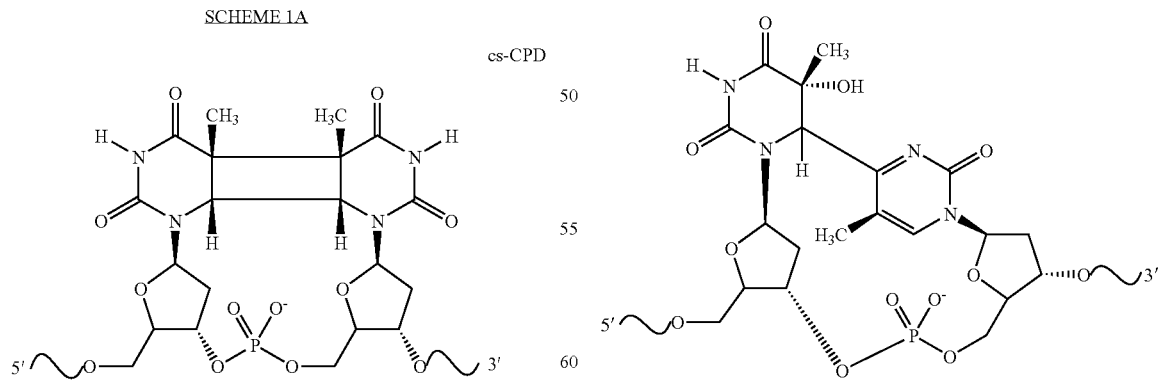

-continued
Dewar
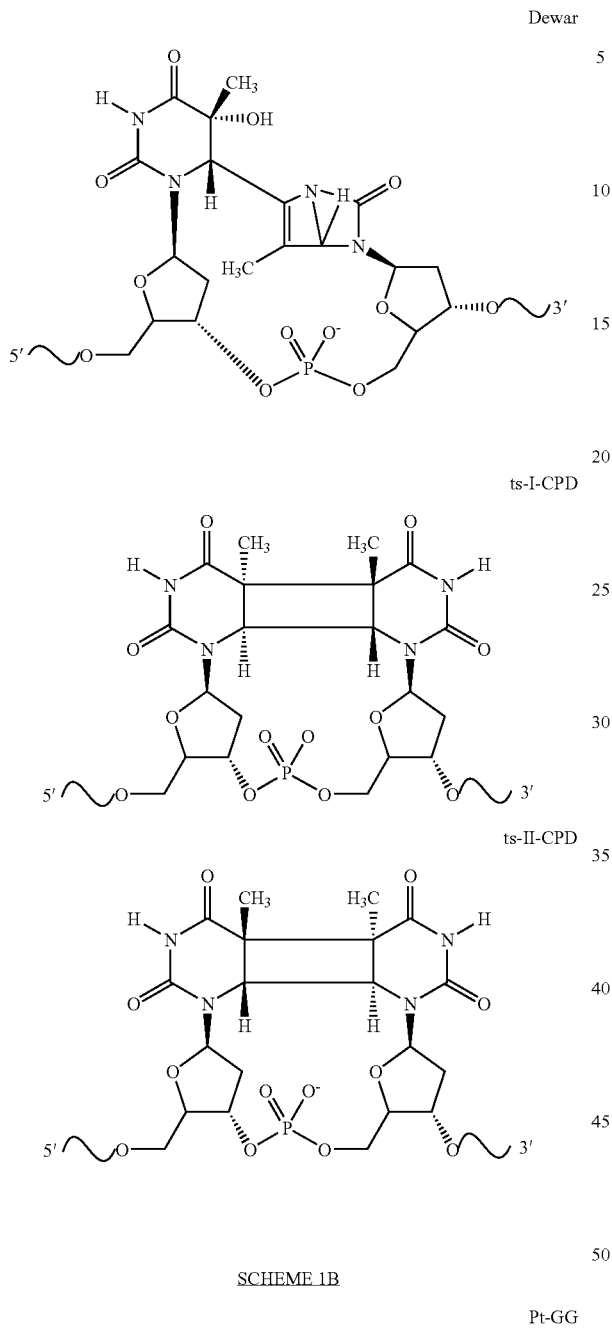
ts-I-CPD
ts-II-CPD
SCHEME 1B
Pt-GG
SCHEME 1C
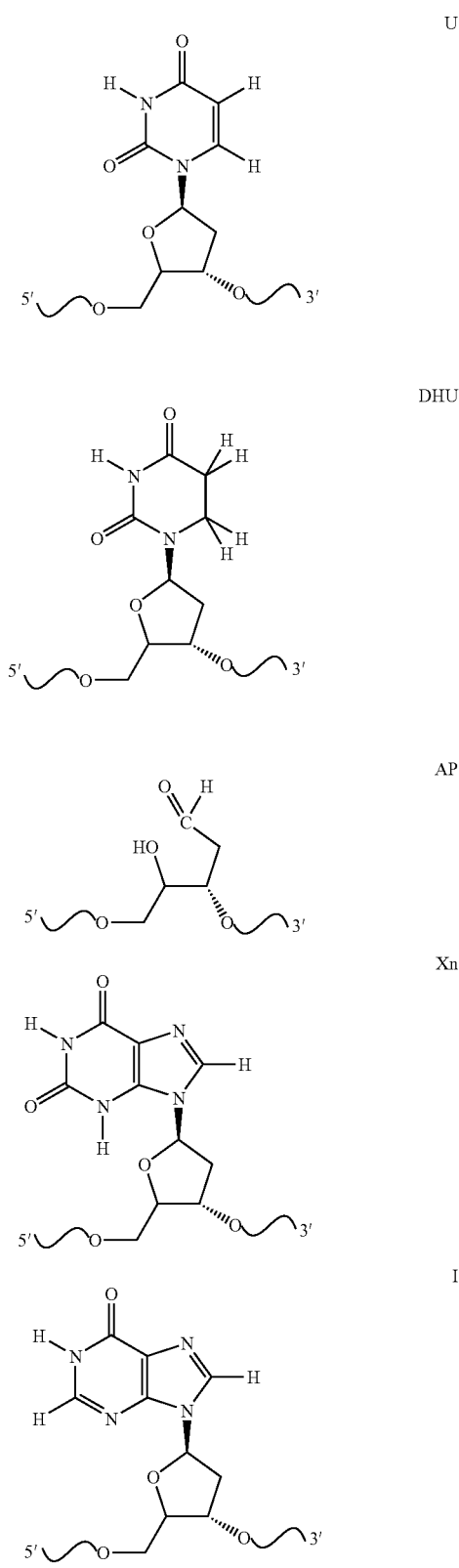
U
DHU
AP
Xn
I

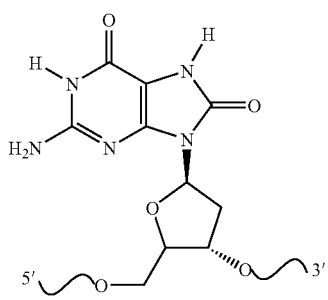

8-oxoG

We claim:

1. A method for cleavage of a double-stranded DNA molecule characterized by a distorted structure, wherein said distorted structure results from a Dewar isomer of 6-4 photoproduct, dihyrouracil, uracil, an abasic site, mismatched nucleotide pairing, a platinum-DNA GG diadduct, an insertion or deletion loop of less than five nucleotides, said method comprising the step of contacting a DNA molecule characterized by a distorted structure with a broadly specific DNA damage endonuclease selected from the group of endonucleases consisting of a stable truncated Uve1p identified by the amino acid sequence as given in SEQ ID NO:4, wherein said Uve1p is at least 90% pure, and a fusion protein comprising a stable truncated Uve1p and a heterologous sequence, wherein said fusion protein Is Identified by the amino acid sequence given in SEQ ID NO:6, under conditions allowing for enzymatic activity of said endonuclease.

2. The method of claim 1 wherein said truncated Uve1p is at least 90% pure and has the amino acid sequence given in SEQ ID NO:4.

3. The method of claim 1 wherein said fusion protein has the amino acid sequence given In SEQ ID NO:6.

* * * * *

SEQUENCE LISTING

<160> NUMBER OF SEQ ID NOS: 71

<210> SEQ ID NO 1
<211> LENGTH: 2492
<212> TYPE: DNA
<213> ORGANISM: Artificial Sequence
<220> FEATURE:
<223> OTHER INFORMATION: Description of Artificial Sequence: Coding
      sequence for fusion protein of  GST signal peptide
      and the UVDE protein of Schizosaccharomyces pombe

<400> SEQUENCE: 1

| | | | | | |
|---|---|---|---|---|---|
| atgaccaagt | tacctatact | aggttattgg | aaaaattaag | ggccttgtgc | aacccactcg | 60 |
| acttcttttg | gaatatcttg | aagaaaaata | tgaagagcat | ttgtatgagc | gcgatgaagg | 120 |
| tgataaatgg | cgaaacaaaa | agtttgaatt | gggtttggag | tttcccaatc | ttccttatta | 180 |
| tattgatggt | gatgttaaat | taacacagtc | tatggccatc | atacgttata | gctgacaa | 240 |
| gcacaacatg | ttggttggtt | gtccaaaaga | gcgtgcagag | atttcaatgc | ttgaaggagc | 300 |
| ggttttggat | attagatacg | gtgtttcgag | aattgcatat | agtaaagact | tgaaactct | 360 |
| caaagttgat | tttcttagca | agctacctga | aatgctgaaa | atgttcgaag | atcgtttatg | 420 |
| tcataaaaca | tatttaaatg | ttgaccatgt | aacccatcct | gacttcatgt | tgtatgacgc | 480 |
| tcttgatgtt | gttttataca | tggacccaat | gtgcctggat | gcgttcccaa | aattagtttg | 540 |
| ttttaaaaaa | cgtattgaag | ctatcccaca | aattgataag | tacttgaaat | ccagcaagta | 600 |
| tatagcatgg | cctttgcagg | gctggcaagc | cacgtttggt | ggtggcgacc | atcctccaaa | 660 |
| atcggatcat | ctggttccgc | gtggatccat | gcttaggcta | ttgaaacgaa | atattcaaat | 720 |
| ctctaaacgc | attgttttca | ccatattaaa | acaaaaggca | tttaaaggta | atcatccttg | 780 |
| tgtaccgtcg | gtttgtacca | ttacttactc | tcgtttttcat | tgtttacccg | atacccttaa | 840 |
| aagtttactt | ccaatgagct | caaaaaccac | actctcaatg | ttaccgcaag | ttaatatcgg | 900 |
| tgcgaattca | ttctctgccg | aaacaccagt | cgacttaaaa | aaagaaatg | agactgagtt | 960 |
| agctaatatc | agtggaccctc | acaaaaaaag | tacttctacg | tctacacgaa | agagggcacg | 1020 |
| tagcagtaaa | aagaaagcga | cagattctgt | ttccgataaa | attgatgagt | ctgttgcgtc | 1080 |
| ctatgattct | tcaactcatc | ttaggcgatc | gtcgagatca | aaaaaaccgg | tcaactacaa | 1140 |
| ttcctcgtca | gaatccgaat | cggaggagca | aattagtaaa | gctactaaaa | aagttaaaca | 1200 |
| aaaagaggaa | gaggagtatg | ttgaagaagt | cgacgaaaag | tctcttaaaa | atgaaagtag | 1260 |
| ctctgacgag | ttcgaaccgg | ttgtgccgga | cagttggaa | actccaattt | ctaaacgaag | 1320 |
| acggtctcgt | tcttctgcaa | aaatttaga | aaaagaatct | acaatgaatc | ttgatgatca | 1380 |
| tgctccacga | gagatgtttg | attgtttgga | caaacccata | ccctggcgag | gacgattggg | 1440 |

```
gtatgcttgt tgaatacta ttttaaggtc aatgaaggag agggttttt gttcacgcac      1500 ctgccgaatt acaaccattc aacgtgatgg gctcgaaagt gtcaagcagc taggtacgca      1560
aaatgtttta gatttaatca aattggttga gtggaatcac aactttggca ttcacttcat      1620
gagagtgagt tctgatttat ttcctttcgc aagccatgca agtatggat ataccttga       1680 atttgcacaa tctcatctcg aggaggtggg caagctggca aataaatata atcatcgatt     1740
gactatgcat cctggtcagt acacccagat agcctctcca cgagaagtcg tagttgattc     1800 ggcaatacg gatttggctt atcatgatga attctcagt cgtatgaagt tgaatgaaca       1860
attaaataaa gacgctgttt taattattca ccttggtggt acctttgaag gaaaaaaga     1920 aacattggat aggtttcgta aaattatca acgcttgtct gattcggtta agctcgttt       1980 agttttagaa acgatgatg tttcttggtc agttcaagat ttattacctt tatgccaaga      2040
acttaatatt cctctagttt tggattggca tcatcacaac atagtgccag gaacgcttcg     2100
tgaaggaagt ttagatttaa tgccattaat cccaactatt cgagaaacct ggacaagaaa     2160
gggaattaca cagaagcaac attactcaga atcggctgat ccaacggcga tttctgggat    2220
gaaacgacgt gctcactctg ataggtgtt tgactttcca ccgtgtgatc ctacaatgga     2280
tctaatgata gaagctaagg aaaggaaca ggctgtattt gaattgtgta gacgttatga     2340
gttacaaaat ccaccatgtc ctcttgaaat tatgggcct gaatacgatc aaactcgaga     2400
tggatattat ccgcccggag ctgaaaagcg tttaactgca agaaaaggc gtagtagaaa      2460 agaagaagta gaagaggatg aaaaataaa at                                    2492
```

<210> SEQ ID NO 2
<211> LENGTH: 828
<212> TYPE: PRT
<213> ORGANISM: Artificial Sequence
<220> FEATURE:
<223> OTHER INFORMATION: Description of Artificial Sequence: Fusion
   protein of GST leader peptide and Schizosaccharomyces
   pombe UVDE

<400> SEQUENCE: 2

```
Met Thr Lys Leu Pro Ile Leu Gly Tyr Trp Lys Ile Lys Gly Leu Val
  1               5                  10                  15

Gln Pro Thr Arg Leu Leu Leu Glu Tyr Leu Glu Glu Lys Tyr Glu Glu
             20                  25                  30

His Leu Tyr Glu Arg Asp Glu Gly Asp Lys Trp Arg Asn Lys Lys Phe
         35                  40                  45

Glu Leu Gly Leu Glu Phe Pro Asn Leu Pro Tyr Tyr Ile Asp Gly Asp
     50                  55                  60

Val Lys Leu Thr Gln Ser Met Ala Ile Ile Arg Tyr Ile Ala Asp Lys
 65                  70                  75                  80

His Asn Met Leu Gly Gly Cys Pro Lys Glu Arg Ala Glu Ile Ser Met
                 85                  90                  95

Leu Glu Gly Ala Val Leu Asp Ile Arg Tyr Gly Val Ser Arg Ile Ala
            100                 105                 110

Tyr Ser Lys Asp Phe Glu Thr Leu Lys Val Asp Phe Leu Ser Lys Leu
        115                 120                 125

Pro Glu Met Leu Lys Met Phe Glu Asp Arg Leu Cys His Lys Thr Tyr
    130                 135                 140

Leu Asn Gly Asp His Val Thr His Pro Asp Phe Met Leu Tyr Asp Ala
145                 150                 155                 160
```

-continued

```
Leu Asp Val Val Leu Tyr Met Asp Pro Met Cys Leu Asp Ala Phe Pro
            165                 170                 175
Lys Leu Val Cys Phe Lys Lys Arg Ile Glu Ala Ile Pro Gln Ile Asp
            180                 185                 190
Lys Tyr Leu Lys Ser Ser Lys Tyr Ile Ala Trp Pro Leu Gln Gly Trp
            195                 200                 205
Gln Ala Thr Phe Gly Gly Gly Asp His Pro Pro Lys Ser Asp His Leu
    210                 215                 220
Val Pro Arg Gly Ser Met Leu Arg Leu Lys Arg Asn Ile Gln Ile
225                 230                 235                 240
Ser Lys Arg Ile Val Phe Thr Ile Leu Lys Gln Lys Ala Phe Lys Gly
                245                 250                 255
Asn His Pro Cys Val Pro Ser Val Cys Thr Ile Thr Tyr Ser Arg Phe
                260                 265                 270
His Cys Leu Pro Asp Thr Leu Lys Ser Leu Pro Met Ser Ser Lys
    275                 280                 285
Thr Thr Leu Ser Met Leu Pro Gln Val Asn Ile Gly Ala Asn Ser Phe
    290                 295                 300
Ser Ala Glu Thr Pro Val Asp Leu Lys Lys Glu Asn Glu Thr Glu Leu
305                 310                 315                 320
Ala Asn Ile Ser Gly Pro His Lys Lys Ser Thr Ser Thr Ser Thr Arg
                325                 330                 335
Lys Arg Ala Arg Ser Ser Lys Lys Ala Thr Asp Ser Val Ser Asp
            340                 345                 350
Lys Ile Asp Glu Ser Val Ala Ser Tyr Asp Ser Ser Thr His Leu Arg
            355                 360                 365
Arg Ser Ser Arg Ser Lys Lys Pro Val Asn Tyr Asn Ser Ser Ser Glu
    370                 375                 380
Ser Glu Ser Glu Glu Gln Ile Ser Lys Ala Thr Lys Lys Val Lys Gln
385                 390                 395                 400
Lys Glu Glu Glu Tyr Val Glu Glu Val Asp Glu Lys Ser Leu Lys
                405                 410                 415
Asn Glu Ser Ser Asp Glu Phe Glu Pro Val Val Pro Glu Gln Leu
            420                 425                 430
Glu Thr Pro Ile Ser Lys Arg Arg Arg Ser Arg Ser Ser Ala Lys Asn
            435                 440                 445
Leu Glu Lys Glu Ser Thr Met Asn Leu Asp Asp His Ala Pro Arg Glu
    450                 455                 460
Met Phe Asp Cys Leu Asp Lys Pro Ile Pro Trp Arg Gly Arg Leu Gly
465                 470                 475                 480
Tyr Ala Cys Leu Asn Thr Ile Leu Arg Ser Met Lys Glu Arg Val Phe
                485                 490                 495
Cys Ser Arg Thr Cys Arg Ile Thr Thr Ile Gln Arg Asp Gly Leu Glu
                500                 505                 510
Ser Val Lys Gln Leu Gly Thr Gln Asn Val Leu Asp Leu Ile Lys Leu
            515                 520                 525
Val Glu Trp Asn His Asn Phe Gly Ile His Phe Met Arg Val Ser Ser
    530                 535                 540
Asp Leu Phe Pro Phe Ala Ser His Ala Lys Tyr Gly Tyr Thr Leu Glu
545                 550                 555                 560
Phe Ala Gln Ser His Leu Glu Glu Val Gly Lys Leu Ala Asn Lys Tyr
                565                 570                 575
Asn His Arg Leu Thr Met His Pro Gly Gln Tyr Thr Gln Ile Ala Ser
```

-continued

```
                580             585             590
Pro Arg Glu Val Val Asp Ser Ala Ile Arg Asp Leu Ala Tyr His
    595                 600                 605

Asp Glu Ile Leu Ser Arg Met Lys Leu Asn Glu Gln Leu Asn Lys Asp
    610                 615                 620

Ala Val Leu Ile Ile His Leu Gly Gly Thr Phe Glu Gly Lys Lys Glu
625                 630                 635                 640

Thr Leu Asp Arg Phe Arg Lys Asn Tyr Gln Arg Leu Ser Asp Ser Val
                645                 650                 655

Lys Ala Arg Leu Val Leu Glu Asn Asp Asp Val Ser Trp Ser Val Gln
            660                 665                 670

Asp Leu Leu Pro Leu Cys Gln Glu Leu Asn Ile Pro Leu Val Leu Asp
            675                 680                 685

Trp His His Asn Ile Val Pro Gly Thr Leu Arg Glu Gly Ser Leu
            690                 695                 700

Asp Leu Met Pro Leu Ile Pro Thr Ile Arg Glu Thr Trp Thr Arg Lys
705                 710                 715                 720

Gly Ile Thr Gln Lys Gln His Tyr Ser Glu Ser Ala Asp Pro Thr Ala
                725                 730                 735

Ile Ser Gly Met Lys Arg Arg Ala His Ser Asp Arg Val Phe Asp Phe
            740                 745                 750

Pro Pro Cys Asp Pro Thr Met Asp Leu Met Ile Glu Ala Lys Glu Lys
            755                 760                 765

Glu Gln Ala Val Phe Glu Leu Cys Arg Arg Tyr Glu Leu Gln Asn Pro
    770                 775                 780

Pro Cys Pro Leu Glu Ile Met Gly Pro Glu Tyr Asp Gln Thr Arg Asp
785                 790                 795                 800

Gly Tyr Tyr Pro Pro Gly Ala Glu Lys Arg Leu Thr Ala Arg Lys Arg
                805                 810                 815

Arg Ser Arg Lys Glu Glu Val Glu Glu Asp Glu Lys
            820                 825
```

<210> SEQ ID NO 3
<211> LENGTH: 1161
<212> TYPE: DNA
<213> ORGANISM: Schizosaccharomyces pombe
<220> FEATURE:
<221> NAME/KEY: misc_feature
<222> LOCATION: (1)..(1161)
<223> OTHER INFORMATION: DNA sequence encoding UVDE protein, truncated at amino acid residue 228.

<400> SEQUENCE: 3

```
gatgatcatg ctccacgaga gatgtttgat tgtttggaca aacccatacc ctggcgagga      60 cgattgggt atgcttgttt gaatactatt ttaaggtcaa tgaaggagag ggttttttgt     120
tcacgcacct gccgaattac aaccattcaa cgtgatgggc tcgaaagtgt caagcagcta     180
ggtacgcaaa atgttttaga tttaatcaaa ttggttgagt ggaatcacaa ctttggcatt     240
cacttcatga gagtgagttc tgatttattt cctttcgcaa gccatgcaaa gtatggatat     300
acccttgaat ttgcacaatc tcatctcgag gaggtgggca agctggcaaa taaatataat     360
catcgattga ctatgcatcc tggtcagtac acccagatag cctctccacg agaagtcgta     420
gttgattcgg caatacgtga tttggcttat catgatgaaa ttctcagtcg tatgaagttg     480
aatgaacaat taaataaaga cgctgtttta attattcacc ttggtggtac ctttgaagga     540 aaaaagaaa cattggatag gtttcgtaaa aattatcaac gcttgtctga ttcggttaaa     600
```

-continued

```
gctcgtttag ttttagaaaa cgatgatgtt tcttggtcag ttcaagattt attacccttta      660 tgccaagaac ttaatattcc tctagttttg gattggcatc atcacaacat agtgccagga      720
acgcttcgtg aaggaagttt agatttaatg ccattaatcc caactattcg agaaacctgg      780
acaagaaagg gaattacaca gaagcaacat tactcagaat cggctgatcc aacggcgatt      840
tctgggatga acgacgtgc tcactctgat agggtgtttg actttccacc gtgtgatcct      900
acaatggatc taatgataga agctaaggaa aaggaacagg ctgtatttga attgtgtaga      960
cgttatgagt tacaaaatcc accatgtcct cttgaaatta tggggcctga atacgatcaa     1020
actcgagatg gatattatcc gcccggagct gaaaagcgtt taactgcaag aaaaaggcgt     1080
agtagaaaag aagaagtaga agaggatgaa aataaaaat ccgtcatact ttttgattta     1140
tggcataatt tagccatctc c                                                1161
```

<210> SEQ ID NO 4
<211> LENGTH: 371
<212> TYPE: PRT
<213> ORGANISM: Schizosaccharomyces pombe
<220> FEATURE:
<221> NAME/KEY: VARIANT
<222> LOCATION: (1)..(371)
<223> OTHER INFORMATION: Truncated version of the UVDE protein.

<400> SEQUENCE: 4

```
Asp Asp His Ala Pro Arg Glu Met Phe Asp Cys Leu Asp Lys Pro Ile
  1               5                  10                  15

Pro Trp Arg Gly Arg Leu Gly Tyr Ala Cys Leu Asn Thr Ile Leu Arg
                 20                  25                  30

Ser Met Lys Glu Arg Val Phe Cys Ser Arg Thr Cys Arg Ile Thr Thr
         35                  40                  45

Ile Gln Arg Asp Gly Leu Glu Ser Val Lys Gln Leu Gly Thr Gln Asn
     50                  55                  60

Val Leu Asp Leu Ile Lys Leu Val Glu Trp Asn His Asn Phe Gly Ile
 65                  70                  75                  80

His Phe Met Arg Val Ser Ser Asp Leu Phe Pro Phe Ala Ser His Ala
                 85                  90                  95

Lys Tyr Gly Tyr Thr Leu Glu Phe Ala Gln Ser His Leu Glu Glu Val
            100                 105                 110

Gly Lys Leu Ala Asn Lys Tyr Asn His Arg Leu Thr Met His Pro Gly
        115                 120                 125

Gln Tyr Thr Gln Ile Ala Ser Pro Arg Glu Val Val Asp Ser Ala
    130                 135                 140

Ile Arg Asp Leu Ala Tyr His Asp Glu Ile Leu Ser Arg Met Lys Leu
145                 150                 155                 160

Asn Glu Gln Leu Asn Lys Asp Ala Val Leu Ile Ile His Leu Gly Gly
                165                 170                 175

Thr Phe Glu Gly Lys Lys Glu Thr Leu Asp Arg Phe Arg Lys Asn Tyr
            180                 185                 190

Gln Arg Leu Ser Asp Ser Val Lys Ala Arg Leu Val Leu Glu Asn Asp
        195                 200                 205

Asp Val Ser Trp Ser Val Gln Asp Leu Leu Pro Leu Cys Gln Glu Leu
    210                 215                 220

Asn Ile Pro Leu Val Leu Asp Trp His His Asn Ile Val Pro Gly
225                 230                 235                 240

Thr Leu Arg Glu Gly Ser Leu Asp Leu Met Pro Leu Ile Pro Thr Ile
```

```
                245                 250                 255
Arg Glu Thr Trp Thr Arg Lys Gly Ile Thr Gln Lys Gln His Tyr Ser
            260                 265                 270

Glu Ser Ala Asp Pro Thr Ala Ile Ser Gly Met Lys Arg Arg Ala His
            275                 280                 285

Ser Asp Arg Val Phe Asp Phe Pro Cys Asp Pro Thr Met Asp Leu
    290                 295                 300

Met Ile Glu Ala Lys Glu Lys Glu Gln Ala Val Phe Glu Leu Cys Arg
305                 310                 315                 320

Arg Tyr Glu Leu Gln Asn Pro Pro Cys Pro Leu Glu Ile Met Gly Pro
                325                 330                 335

Glu Tyr Asp Gln Thr Arg Asp Gly Tyr Tyr Pro Pro Gly Ala Glu Lys
            340                 345                 350

Arg Leu Thr Ala Arg Lys Arg Ser Arg Lys Glu Glu Val Glu Glu
            355                 360                 365

Asp Glu Lys
    370

<210> SEQ ID NO 5
<211> LENGTH: 1811
<212> TYPE: DNA
<213> ORGANISM: Artificial Sequence
<220> FEATURE:
<223> OTHER INFORMATION: Description of Artificial Sequence: Nucleotide
      sequence encoding fusion protein of GST signal
      peptide and the truncated version of S. pombe UVDE
      protein.

<400> SEQUENCE: 5
atgaccaagt tacctatact aggttattgg aaaaattaag ggccttgtgc aacccactcg      60
acttcttttg gaatatcttg aagaaaaata tgaagagcat ttgtatgagc gcgatgaagg     120
tgataaatgg cgaaacaaaa agtttgaatt gggtttggag tttcccaatc ttccttatta     180
tattgatggt gatgttaaat aacacagtc tatggccatc atacgttata gctgacaa       240 gcacaacatg ttggttggtt gtccaaaaga gcgtgcagag atttcaatgc ttgaaggagc     300
ggttttggat attagatacg gtgtttcgag aattgcatat agtaaagact tgaaactct      360 caaagttgat tttcttagca agctacctga atgctgaaa atgttcgaag atcgtttatg     420
tcataaaaca tatttaaatg ttgaccatgt aacccatcct gacttcatgt tgtatgacgc     480
tcttgatgtt gttttataca tggacccaat gtgcctggat gcgttcccaa aattagttg     540 ttttaaaaaa cgtattgaag ctatcccaca aattgataag tacttgaaat ccagcaagta    600
tatagcatgg cctttgcagg gctggcaagc cacgtttggt ggtggcgacc atcctccaaa    660
atcggatcat ctggttccgc gtggatccga tgatcatgct ccacgagaga tgtttgattg    720
tttggacaaa cccataccct ggcgaggacg attgggtat gcttgtttga atactatttt     780
aaggtcaatg aaggagaggg tttttttgttc acgcacctgc cgaattacaa ccattcaacg    840
tgatgggctc gaaagtgtca agcagctagg tacgcaaaat gttttagatt taatcaaatt    900
ggttgagtgg aatcacaact ttggcattca cttcatgaga gtgagttctg atttatttcc    960
tttcgcaagc catgcaaagt atggatatac ccttgaattt gcacaatctc atctcgagga   1020
ggtgggcaag ctggcaaata aatataatca tcgattgact atgcatcctg gtcagtacac   1080
ccagatagcc tctccacgag aagtcgtagt tgattcggca atacgtgatt ggcttatca    1140 tgatgaaatt ctcagtcgta tgaagttgaa tgaacaatta aataaagacg ctgttttaat   1200
```

```
tattcacctt ggtggtacct ttgaaggaaa aaaagaaaca ttggataggt ttcgtaaaaa    1260
ttatcaacgc ttgtctgatt cggttaaagc tcgtttagtt ttagaaaacg atgatgtttc    1320
ttggtcagtt caagatttat tacctttatg ccaagaactt aatattcctc tagttttgga    1380
ttggcatcat cacaacatag tgccaggaac gcttcgtgaa ggaagtttag atttaatgcc    1440
attaatccca actattcgag aaacctggac aagaaaggga attacacaga agcaacatta    1500
ctcagaatcg gctgatccaa cggcgatttc tgggatgaaa cgacgtgctc actctgatag    1560 ggtgttttgac tttccaccgt gtgatcctac aatggatcta atgatagaag ctaaggaaaa    1620
ggaacaggct gtatttgaat tgtgtagacg ttatgagtta caaaatccac catgtcctct    1680
tgaaattatg gggcctgaat acgatcaaac tcgagatgga tattatccgc ccggagctga    1740
aaagcgttta actgcaagaa aaaggcgtag tagaaaagaa gaagtagaag aggatgaaaa    1800
ataaggatcc c                                                          1811
```

<210> SEQ ID NO 6
<211> LENGTH: 600
<212> TYPE: PRT
<213> ORGANISM: Artificial Sequence
<220> FEATURE:
<223> OTHER INFORMATION: Description of Artificial Sequence: Fusion
      protein comprising the GST signal peptide and the
      truncated UVDE protein of S. pombe.

<400> SEQUENCE: 6

```
Met Thr Lys Leu Pro Ile Leu Gly Tyr Trp Lys Ile Lys Gly Leu Val
  1               5                  10                  15

Gln Pro Thr Arg Leu Leu Leu Glu Tyr Leu Glu Glu Lys Tyr Glu Glu
             20                  25                  30

His Leu Tyr Glu Arg Asp Glu Gly Asp Lys Trp Arg Asn Lys Lys Phe
         35                  40                  45

Glu Leu Gly Leu Glu Phe Pro Asn Leu Pro Tyr Tyr Ile Asp Gly Asp
     50                  55                  60

Val Lys Leu Thr Gln Ser Met Ala Ile Ile Arg Tyr Ile Ala Asp Lys
 65                  70                  75                  80

His Asn Met Leu Gly Gly Cys Pro Lys Glu Arg Ala Glu Ile Ser Met
                 85                  90                  95

Leu Glu Gly Ala Val Leu Asp Ile Arg Tyr Gly Val Ser Arg Ile Ala
            100                 105                 110

Tyr Ser Lys Asp Phe Glu Thr Leu Lys Val Asp Phe Leu Ser Lys Leu
        115                 120                 125

Pro Glu Met Leu Lys Met Phe Glu Asp Arg Leu Cys His Lys Thr Tyr
    130                 135                 140

Leu Asn Gly Asp His Val Thr His Pro Asp Phe Met Leu Tyr Asp Ala
145                 150                 155                 160

Leu Asp Val Val Leu Tyr Met Asp Pro Met Cys Leu Asp Ala Phe Pro
                165                 170                 175

Lys Leu Val Cys Phe Lys Lys Arg Ile Glu Ala Ile Pro Gln Ile Asp
            180                 185                 190

Lys Tyr Leu Lys Ser Ser Lys Tyr Ile Ala Trp Pro Leu Gln Gly Trp
        195                 200                 205

Gln Ala Thr Phe Gly Gly Gly Asp His Pro Pro Lys Ser Asp His Leu
    210                 215                 220

Val Pro Arg Gly Ser Asp Asp His Ala Pro Arg Glu Met Phe Asp Cys
225                 230                 235                 240
```

-continued

```
Leu Asp Lys Pro Ile Pro Trp Arg Gly Arg Leu Gly Tyr Ala Cys Leu
                245                 250                 255

Asn Thr Ile Leu Arg Ser Met Lys Glu Arg Val Phe Cys Ser Arg Thr
            260                 265                 270

Cys Arg Ile Thr Thr Ile Gln Arg Asp Gly Leu Glu Ser Val Lys Gln
        275                 280                 285

Leu Gly Thr Gln Asn Val Leu Asp Leu Ile Lys Leu Val Glu Trp Asn
    290                 295                 300

His Asn Phe Gly Ile His Phe Met Arg Val Ser Ser Asp Leu Phe Pro
305                 310                 315                 320

Phe Ala Ser His Ala Lys Tyr Gly Tyr Thr Leu Glu Phe Ala Gln Ser
                325                 330                 335

His Leu Glu Glu Val Gly Lys Leu Ala Asn Lys Tyr Asn His Arg Leu
            340                 345                 350

Thr Met His Pro Gly Gln Tyr Thr Gln Ile Ala Ser Pro Arg Glu Val
        355                 360                 365

Val Val Asp Ser Ala Ile Arg Asp Leu Ala Tyr His Asp Glu Ile Leu
    370                 375                 380

Ser Arg Met Lys Leu Asn Glu Gln Leu Asn Lys Asp Ala Val Leu Ile
385                 390                 395                 400

Ile His Leu Gly Gly Thr Phe Glu Gly Lys Lys Glu Thr Leu Asp Arg
                405                 410                 415

Phe Arg Lys Asn Tyr Gln Arg Leu Ser Asp Ser Val Lys Ala Arg Leu
            420                 425                 430

Val Leu Glu Asn Asp Asp Val Ser Trp Ser Val Gln Asp Leu Leu Pro
        435                 440                 445

Leu Cys Gln Glu Leu Asn Ile Pro Leu Val Leu Asp Trp His His His
    450                 455                 460

Asn Ile Val Pro Gly Thr Leu Arg Glu Gly Ser Leu Asp Leu Met Pro
465                 470                 475                 480

Leu Ile Pro Thr Ile Arg Glu Thr Trp Thr Arg Lys Gly Ile Thr Gln
                485                 490                 495

Lys Gln His Tyr Ser Glu Ser Ala Asp Pro Thr Ala Ile Ser Gly Met
            500                 505                 510

Lys Arg Arg Ala His Ser Asp Arg Val Phe Asp Phe Pro Pro Cys Asp
        515                 520                 525

Pro Thr Met Asp Leu Met Ile Glu Ala Lys Glu Lys Glu Gln Ala Val
    530                 535                 540

Phe Glu Leu Cys Arg Arg Tyr Glu Leu Gln Asn Pro Pro Cys Pro Leu
545                 550                 555                 560

Glu Ile Met Gly Pro Glu Tyr Asp Gln Thr Arg Asp Gly Tyr Tyr Pro
                565                 570                 575

Pro Gly Ala Glu Lys Arg Leu Thr Ala Arg Lys Arg Ser Arg Lys
            580                 585                 590

Glu Glu Val Glu Glu Asp Glu Lys
        595                 600
```

<210> SEQ ID NO 7
<211> LENGTH: 688
<212> TYPE: DNA
<213> ORGANISM: Artificial Sequence
<220> FEATURE:
<223> OTHER INFORMATION: Description of Artificial Sequence: Nucleotide
      sequence encoding GST signal peptide.

<400> SEQUENCE: 7

```
atgaccaagt tacctatact aggttattgg aaaaattaag ggccttgtgc aacccactcg      60
acttctttg gaatatcttg aagaaaaata tgaagagcat ttgtatgagc gcgatgaagg      120
tgataaatgg cgaaacaaaa agtttgaatt gggtttggag tttcccaatc ttccttatta    180
tattgatggt gatgttaaat aacacagtc tatggccatc atacgttata tagctgacaa    240
gcacaacatg ttggttggtt gtccaaaaga gcgtgcagag atttcaatgc ttgaaggagc    300
ggttttggat attagatacg gtgtttcgag aattgcatat agtaaagact ttgaaactct    360
caaagttgat tttcttagca agctaccttga aatgctgaaa atgttcgaag atcgtttatg    420
tcataaaaca tatttaaatg ttgaccatgt aacccatcct gacttcatgt tgtatgacgc    480
tcttgatgtt gttttataca tggacccaat gtgcctggag gcgttcccaa aattagtttg    540
ttttaaaaaa cgtattgaag ctatcccaca aattgataag tacttgaaat ccagcaagta    600
tatagcatgg cctttgcagg gctggcaagc cacgtttggt ggtggcgacc atcctccaaa    660
atcggatcat ctggttccgc gtggatcc                                          688
```

<210> SEQ ID NO 8
<211> LENGTH: 229
<212> TYPE: PRT
<213> ORGANISM: Artificial Sequence
<220> FEATURE:
<223> OTHER INFORMATION: Description of Artificial Sequence: Amino acid sequence of GST signal peptide

<400> SEQUENCE: 8

```
Met Thr Lys Leu Pro Ile Leu Gly Tyr Trp Lys Ile Lys Gly Leu Val
 1               5                  10                  15
Gln Pro Thr Arg Leu Leu Leu Glu Tyr Leu Glu Glu Lys Tyr Glu Glu
             20                  25                  30
His Leu Tyr Glu Arg Asp Glu Gly Asp Lys Trp Arg Asn Lys Lys Phe
         35                  40                  45
Glu Leu Gly Leu Glu Phe Pro Asn Leu Pro Tyr Tyr Ile Asp Gly Asp
     50                  55                  60
Val Lys Leu Thr Gln Ser Met Ala Ile Ile Arg Tyr Ile Ala Asp Lys
 65                  70                  75                  80
His Asn Met Leu Gly Gly Cys Pro Lys Glu Arg Ala Glu Ile Ser Met
                 85                  90                  95
Leu Glu Gly Ala Val Leu Asp Ile Arg Tyr Gly Val Ser Arg Ile Ala
            100                 105                 110
Tyr Ser Lys Asp Phe Glu Thr Leu Lys Val Asp Phe Leu Ser Lys Leu
        115                 120                 125
Pro Glu Met Leu Lys Met Phe Glu Asp Arg Leu Cys His Lys Thr Tyr
    130                 135                 140
Leu Asn Gly Asp His Val Thr His Pro Asp Phe Met Leu Tyr Asp Ala
145                 150                 155                 160
Leu Asp Val Val Leu Tyr Met Asp Pro Met Cys Leu Asp Ala Phe Pro
                165                 170                 175
Lys Leu Val Cys Phe Lys Lys Arg Ile Glu Ala Ile Pro Gln Ile Asp
            180                 185                 190
Lys Tyr Leu Lys Ser Ser Lys Tyr Ile Ala Trp Pro Leu Gln Gly Trp
        195                 200                 205
Gln Ala Thr Phe Gly Gly Gly Asp His Pro Pro Lys Ser Asp His Leu
    210                 215                 220
Val Pro Arg Gly Ser
```

-continued

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
tgaggatcca atcgttttca tttttttaatg cttagg                                  36

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
ggccatggtt atttttcatc ctc                                                 23

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
aatgggatcc gatgatcatg ctccacga                                            28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
gggatcctta tttttcatcc tcttctac                                            28

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Double
      stranded oligonucleotide containing cis-syn
      cyclobutane pyrimidine dimer.
<221> NAME/KEY: misc_feature
<222> LOCATION: (15)..(16)
<223> OTHER INFORMATION: At positions 15- 16, the T-T is in the form of
      cis-syn cyclobutane pyrimidine dimer.

<400> SEQUENCE: 13
catgcctgca cgaattaagc aattcgtaat                                          30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Undamaged

```
            double stranded oligonucleotide.

<400> SEQUENCE: 14
catgcctgca cgaattaagc aattcgtaat                                    30

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence: Double
      stranded oligonucleotide containing cis-syn
      cyclobutane dimer at positions 21-22.

<400> SEQUENCE: 15
agctaccatg cctgcacgaa ttaagcaatt cgtaatcatg gtcatagct               49

<210> SEQ ID NO 16
<211> LENGTH: 49
<212> TYPE: DNA
<213> ORGANISM: Artificial Sequence
<220> FEATURE:
<223> OTHER INFORMATION: Description of Artificial Sequence: Double
      stranded oligonucleotide containing cis-syn
      cyclobutane pyrimidine dimer at positions 21-22.

<400> SEQUENCE: 16
agctaccatg cctgcacgaa ttaagcaatt cgtaatcatg gtcatagct               49

<210> SEQ ID NO 17
<211> LENGTH: 49
<212> TYPE: DNA
<213> ORGANISM: Artificial Sequence
<220> FEATURE:
<223> OTHER INFORMATION: Description of Artificial Sequence: Double
      stranded oligonucleotide containing trans- syn 11
      cyclobutane pyrimidine dimer at positions 21-22.

<400> SEQUENCE: 17
agctaccatg cctgcacgaa ttaagcaatt cgtaatcatg gtcatagct               49

<210> SEQ ID NO 18
<211> LENGTH: 49
<212> TYPE: DNA
<213> ORGANISM: Artificial Sequence
<220> FEATURE:
<223> OTHER INFORMATION: Description of Artificial Sequence: Double
      stranded oligonucleotide containing a 6-4 photo
      product at position 21-22.

<400> SEQUENCE: 18
agctaccatg cctgcacgaa ttaagcaatt cgtaatcatg gtcatagct               49

<210> SEQ ID NO 19
<211> LENGTH: 49
<212> TYPE: DNA
<213> ORGANISM: Artificial Sequence
<220> FEATURE:
<223> OTHER INFORMATION: Description of Artificial Sequence: Double
      stranded oligonucleotide containing a Dewar
      isomer.

<400> SEQUENCE: 19
agctaccatg cctgcacgaa ttaagcaatt cgtaatcatg gtcatagct               49

<210> SEQ ID NO 20
<211> LENGTH: 32
```

```
<212> TYPE: DNA
<213> ORGANISM: Artificial Sequence
<220> FEATURE:
<223> OTHER INFORMATION: Description of Artificial Sequence: Double
      stranded oligonucleotide containing cisplatin DNA
      diadduct at position 16-17.

<400> SEQUENCE: 20
tccctccttc cttccggccc tccttcccct tc                                32

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Double
      stranded oligonucleotide  wherein n is uracil at
      position 21.
<221> NAME/KEY: misc_feature
<222> LOCATION: (21)
<223> OTHER INFORMATION: The n at position 21 is uracil.

<400> SEQUENCE: 21
cttggactgg atgtcggcac nagcggatac aggagca                           37

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: Double
      stranded oligonucleotide wherein n is
      dihydrouracil at position 21.
<221> NAME/KEY: misc_feature
<222> LOCATION: (21)
<223> OTHER INFORMATION: At position 21, n is dihydrouracil.

<400> SEQUENCE: 22
cttggactgg atgtcggcac nagcggatac aggagca                           37

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: Double
      stranded oligonucleotide wherein n at position 21
      represents an abasic site.
<221> NAME/KEY: misc_feature
<222> LOCATION: (21)
<223> OTHER INFORMATION: At position 21, n is an abasic site.

<400> SEQUENCE: 23
cttggactgg atgtcggcac nagcggatac aggagca                           37

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: Double
      stranded oligonucleotide wherein n at position 13
      is an inosine.
<221> NAME/KEY: misc_feature
<222> LOCATION: (13)
<223> OTHER INFORMATION: At position 13, n is inosine.

<400> SEQUENCE: 24
tgcaggtcga ctnaggagga tccccgggta c                                 31
```

```
<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: Double
      stranded oligonucleotide wherein n at position 13
      is xanthine.
<221> NAME/KEY: misc_feature
<222> LOCATION: (13)
<223> OTHER INFORMATION: N at position 13 is xanthine.

<400> SEQUENCE: 25
tgcaggtcga ctnaggagga tccccgggta c                              31

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Double
      stranded oligonucleotide wherein n at position 21
      is 8-oxoguanine.
<221> NAME/KEY: misc_feature
<222> LOCATION: (21)
<223> OTHER INFORMATION: N at position 21 is 8-oxoguanine.

<400> SEQUENCE: 26
cttggactgg atgtcggcac nagcggatac aggagca                        37

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Double
      stranded oligonucleotide representing all 16
      possible base pair mismatches at position 18 in
      individual preparations.
<221> NAME/KEY: misc_feature
<222> LOCATION: (18)
<223> OTHER INFORMATION: N at position 18 represents all 16 possible
      base pair mismatches.

<400> SEQUENCE: 27
gtacccgggg atcctccnag tcgacctgca                                30

<210> SEQ ID NO 28
<211> LENGTH: 41
<212> TYPE: DNA
<213> ORGANISM: Artificial Sequence
<220> FEATURE:
<223> OTHER INFORMATION: Description of Artificial Sequence: Double
      stranded oligonucleotide containing a CA
      mismatched base pair at position 21.
<221> NAME/KEY: misc_feature
<222> LOCATION: (21)
<223> OTHER INFORMATION: N at position 21 represents C of C/A mismatched
      base pair.

<400> SEQUENCE: 28
cgttagcatg cctgcacgaa ntaagcaatt cgtaatgcat t                   41

<210> SEQ ID NO 29
<211> LENGTH: 41
<212> TYPE: DNA
<213> ORGANISM: Artificial Sequence
<220> FEATURE:
<223> OTHER INFORMATION: Description of Artificial Sequence: Double
      stranded oligonucleotide wherein there is a C/A
```

```
        mismatched base pair at position 36.
<221> NAME/KEY: misc_feature
<222> LOCATION: (36)
<223> OTHER INFORMATION: N at position 36 represents a C/A mismatched
      base pair.

<400> SEQUENCE: 29
cgttacaagt ccgtcacgaa ttaagcaatt cgtaangcat t                       41

<210> SEQ ID NO 30
<211> LENGTH: 41
<212> TYPE: DNA
<213> ORGANISM: Artificial Sequence
<220> FEATURE:
<223> OTHER INFORMATION: Description of Artificial Sequence: Double
      stranded oligonucleotide wherein n at position 31
      represents a C/A mismatched base pair.
<221> NAME/KEY: misc_feature
<222> LOCATION: (31)
<223> OTHER INFORMATION: The n at position 31 represents C of C/A
      mismatched base pair.

<400> SEQUENCE: 30
cgttacaagt ccgtcacgaa ttaagcaatt ngtaacgcat t                       41

<210> SEQ ID NO 31
<211> LENGTH: 41
<212> TYPE: DNA
<213> ORGANISM: Artificial Sequence
<220> FEATURE:
<223> OTHER INFORMATION: Description of Artificial Sequence: Double
      stranded oligonucleotide wherein n at position 26
      is a C/A mismatched base pair.
<221> NAME/KEY: misc_feature
<222> LOCATION: (26)
<223> OTHER INFORMATION: N at position 26 represents a C/A mismatched
      base pair.

<400> SEQUENCE: 31
cgttacaagt ccgtcacgaa ttaagnaatt cgtaacgcat t                       41

<210> SEQ ID NO 32
<211> LENGTH: 41
<212> TYPE: DNA
<213> ORGANISM: Artificial Sequence
<220> FEATURE:
<223> OTHER INFORMATION: Description of Artificial Sequence: Double
      stranded oligonucleotide wherein n at position 21
      is a C/A mismatched base pair.
<221> NAME/KEY: misc_feature
<222> LOCATION: (21)
<223> OTHER INFORMATION: The n at position 21 represents a C/A
      mismatched base pair.

<400> SEQUENCE: 32
cgttacaagt ccgtcacgac ntaagcaatt cgtaacgcat t                       41

<210> SEQ ID NO 33
<211> LENGTH: 41
<212> TYPE: DNA
<213> ORGANISM: Artificial Sequence
<220> FEATURE:
<223> OTHER INFORMATION: Description of Artificial Sequence: Double
      stranded oligonucleotide wherein n at position 15
      represents a C/A mismatched base pair.
<221> NAME/KEY: misc_feature
<222> LOCATION: (15)
<223> OTHER INFORMATION: The n at position 15 represents a C/A
      mismatched base pair.

<400> SEQUENCE: 33
```
cgttacaagt ccgtnacgaa ttaagcaatt cgtaacgcat t                                41

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence: Double
      stranded oligonucleotide wherein n at position 10
      is a C/A mismatched base pair.
<221> NAME/KEY: misc_feature
<222> LOCATION: (10)
<223> OTHER INFORMATION: The n at position 10 represents a C/A
      mismatched base pair.

<400> SEQUENCE: 34
cgttacaagn ccgtcacgaa ttaagcaatt cgtaacgcat t                                41

<210> SEQ ID NO 35
<211> LENGTH: 41
<212> TYPE: DNA
<213> ORGANISM: Artificial Sequence
<220> FEATURE:
<223> OTHER INFORMATION: Description of Artificial Sequence: Double
      stranded oligonucleotide wherein n at position 5
      is a C/A mismatched base pair.
<221> NAME/KEY: misc_feature
<222> LOCATION: (5)
<223> OTHER INFORMATION: The n at position 5 represents a C/A mismatched
      base pair.

<400> SEQUENCE: 35
cgttncaagt ccgtcacgaa ttaagcaatt cgtaacgcat t                                41

<210> SEQ ID NO 36
<211> LENGTH: 656
<212> TYPE: PRT
<213> ORGANISM: Neurospora crassa

<400> SEQUENCE: 36

Met Pro Ser Arg Lys Ser Lys Ala Ala Ala Leu Asp Thr Pro Gln Ser
 1               5                  10                  15

Glu Ser Ser Thr Phe Ser Ser Thr Leu Asp Ser Ser Ala Pro Ser Pro
                20                  25                  30

Ala Arg Asn Leu Arg Arg Ser Gly Arg Asn Ile Leu Gln Pro Ser Ser
            35                  40                  45

Glu Lys Asp Arg Asp His Glu Lys Arg Ser Gly Glu Glu Leu Ala Gly
        50                  55                  60

Arg Met Met Gly Lys Asp Ala Asn Gly His Cys Leu Arg Glu Gly Lys
65                  70                  75                  80

Glu Gln Glu Glu Gly Val Lys Met Ala Ile Glu Gly Leu Ala Arg Met
                85                  90                  95

Glu Arg Arg Leu Gln Arg Ala Thr Lys Arg Gln Lys Lys Gln Leu Glu
            100                 105                 110

Glu Asp Gly Ile Pro Val Pro Ser Val Val Ser Arg Phe Pro Thr Ala
        115                 120                 125

Pro Tyr His His Lys Ser Thr Asn Ala Glu Glu Arg Glu Ala Lys Glu
    130                 135                 140

Pro Val Leu Lys Thr His Ser Lys Asp Val Glu Arg Glu Ala Glu Ile
145                 150                 155                 160

Gly Val Asp Asp Val Val Lys Met Glu Pro Ala Ala Thr Asn Ile Ile
                165                 170                 175

```
Glu Pro Glu Asp Ala Gln Asp Ala Ala Glu Arg Gly Ala Ala Arg Pro
            180                 185                 190

Pro Ala Val Asn Ser Ser Tyr Leu Pro Leu Pro Trp Lys Gly Arg Leu
        195                 200                 205

Gly Tyr Ala Cys Leu Asn Thr Tyr Leu Arg Asn Ala Lys Pro Pro Ile
        210                 215                 220

Phe Ser Ser Arg Thr Cys Arg Met Ala Ser Ile Val Asp His Arg His
225                 230                 235                 240

Pro Leu Gln Phe Glu Asp Glu Pro His His Leu Lys Asn Lys Pro
            245                 250                 255

Asp Lys Ser Lys Glu Pro Gln Asp Glu Leu Gly His Lys Phe Val Gln
        260                 265                 270

Glu Leu Gly Leu Ala Asn Ala Arg Asp Ile Val Lys Met Leu Cys Trp
            275                 280                 285

Asn Glu Lys Tyr Gly Ile Arg Phe Leu Arg Leu Ser Ser Glu Met Phe
        290                 295                 300

Pro Phe Ala Ser His Pro Val His Gly Tyr Lys Leu Ala Pro Phe Ala
305                 310                 315                 320

Ser Glu Val Leu Ala Glu Ala Gly Arg Val Ala Ala Glu Leu Gly His
            325                 330                 335

Arg Leu Thr Thr His Pro Gly Gln Phe Thr Gln Leu Gly Ser Pro Arg
        340                 345                 350

Lys Glu Val Val Glu Ser Ala Ile Arg Asp Leu Glu Tyr His Asp Glu
            355                 360                 365

Leu Leu Ser Leu Leu Lys Leu Pro Glu Gln Gln Asn Arg Asp Ala Val
        370                 375                 380

Met Ile Ile His Met Gly Gly Gln Phe Gly Asp Lys Ala Ala Thr Leu
385                 390                 395                 400

Glu Arg Phe Lys Arg Asn Tyr Ala Arg Leu Ser Gln Ser Cys Lys Asn
            405                 410                 415

Arg Leu Val Leu Glu Asn Asp Asp Val Gly Trp Thr Val His Asp Leu
        420                 425                 430

Leu Pro Val Cys Glu Glu Leu Asn Ile Pro Met Val Leu Asp Tyr His
            435                 440                 445

His His Asn Ile Cys Phe Asp Pro Ala His Leu Arg Glu Gly Thr Leu
        450                 455                 460

Asp Ile Ser Asp Pro Lys Leu Gln Glu Arg Ile Ala Asn Thr Trp Lys
465                 470                 475                 480

Arg Lys Gly Ile Lys Gln Lys Met His Tyr Ser Glu Pro Cys Asp Gly
            485                 490                 495

Ala Val Thr Pro Arg Asp Arg Lys His Arg Pro Arg Val Met Thr
        500                 505                 510

Leu Pro Pro Cys Pro Pro Asp Met Asp Leu Met Ile Glu Ala Lys Asp
            515                 520                 525

Lys Glu Gln Ala Val Phe Glu Leu Met Arg Thr Phe Lys Leu Pro Gly
        530                 535                 540

Phe Glu Lys Ile Asn Asp Met Val Pro Tyr Asp Arg Asp Glu Asn
545                 550                 555                 560

Arg Pro Ala Pro Pro Val Lys Ala Pro Lys Lys Lys Gly Gly Lys
            565                 570                 575

Arg Lys Arg Thr Thr Asp Glu Glu Ala Ala Glu Pro Glu Glu Val Asp
        580                 585                 590
```

```
        Thr Ala Ala Asp Asp Val Lys Asp Ala Pro Glu Gly Pro Lys Glu Val
                    595                 600                 605

Pro Glu Glu Glu Arg Ala Met Gly Gly Pro Tyr Asn Arg Val Tyr Trp
            610                 615                 620

Pro Leu Gly Cys Glu Glu Trp Leu Lys Pro Lys Arg Glu Val Lys
        625                 630                 635                 640

Lys Gly Lys Val Pro Glu Val Glu Asp Glu Gly Glu Phe Asp Gly
                        645                 650                 655

<210> SEQ ID NO 37
<211> LENGTH: 317
<212> TYPE: PRT
<213> ORGANISM: Bacillus subtilis

<400> SEQUENCE: 37

Met Ile Phe Arg Phe Gly Phe Val Ser Asn Ala Met Ser Leu Trp Asp
        1               5                   10                  15

Ala Ser Pro Ala Lys Thr Leu Thr Phe Ala Arg Tyr Ser Lys Leu Ser
                        20                  25                  30

Lys Thr Glu Arg Lys Glu Ala Leu Leu Thr Val Thr Lys Ala Asn Leu
                    35                  40                  45

Arg Asn Thr Met Arg Thr Leu His Tyr Ile Ile Gly His Gly Ile Pro
            50                  55                  60

Leu Tyr Arg Phe Ser Ser Ser Ile Val Pro Leu Ala Thr His Pro Asp
        65                  70                  75                  80

Val Met Trp Asp Phe Val Thr Pro Phe Gln Lys Glu Phe Arg Glu Ile
                        85                  90                  95

Gly Glu Leu Val Lys Thr His Gln Leu Arg Thr Ser Phe His Pro Asn
                    100                 105                 110

Gln Phe Thr Leu Phe Thr Ser Pro Lys Glu Ser Val Thr Lys Asn Ala
                115                 120                 125

Val Thr Asp Met Ala Tyr His Tyr Arg Met Leu Glu Ala Met Gly Ile
            130                 135                 140

Ala Asp Arg Ser Val Ile Asn Ile His Ile Gly Gly Ala Tyr Gly Asn
        145                 150                 155                 160

Lys Asp Thr Ala Thr Ala Gln Phe His Gln Asn Ile Lys Gln Leu Pro
                        165                 170                 175

Gln Glu Ile Lys Glu Arg Met Thr Leu Glu Asn Asp Asp Lys Thr Tyr
                    180                 185                 190

Thr Thr Glu Glu Thr Leu Gln Val Cys Glu Gln Glu Asp Val Pro Phe
                195                 200                 205

Val Phe Asp Phe His His Phe Tyr Ala Asn Pro Asp Asp His Ala Asp
            210                 215                 220

Leu Asn Val Ala Leu Pro Arg Met Ile Lys Thr Trp Glu Arg Ile Gly
        225                 230                 235                 240

Leu Gln Pro Lys Val His Leu Ser Ser Pro Lys Ser Glu Gln Ala Ile
                        245                 250                 255

Arg Ser His Ala Asp Tyr Val Asp Ala Asn Phe Leu Leu Glu Arg Phe
                    260                 265                 270

Arg Gln Trp Gly Thr Asn Ile Asp Phe Met Ile Glu Ala Lys Gln Lys
                275                 280                 285

Asp Lys Ala Leu Leu Arg Leu Met Asp Glu Leu Ser Ser Ile Arg Gly
            290                 295                 300

Val Lys Arg Ile Gly Gly Gly Ala Leu Gln Trp Lys Ser
        305                 310                 315
```

<210> SEQ ID NO 38
<211> LENGTH: 580
<212> TYPE: PRT
<213> ORGANISM: Homo sapiens

<400> SEQUENCE: 38

Met Gly Thr Thr Gly Leu Glu Ser Leu Ser Leu Gly Asp Arg Gly Ala
 1               5                  10                  15

Ala Pro Thr Val Thr Ser Glu Arg Leu Val Pro Asp Pro Asn
             20                  25                  30

Asp Leu Arg Lys Glu Asp Val Ala Met Glu Leu Glu Arg Val Gly Glu
         35                  40                  45

Asp Glu Glu Gln Met Met Ile Lys Arg Ser Ser Glu Cys Asn Pro Leu
     50                  55                  60

Leu Gln Glu Pro Ile Ala Ser Ala Gln Phe Gly Ala Thr Ala Gly Thr
 65                  70                  75                  80

Glu Cys Arg Lys Ser Val Pro Cys Gly Trp Glu Arg Val Val Lys Gln
                 85                  90                  95

Arg Leu Phe Gly Lys Thr Ala Gly Arg Phe Asp Val Tyr Phe Ile Ser
            100                 105                 110

Pro Gln Gly Leu Lys Phe Arg Ser Lys Ser Ser Leu Ala Asn Tyr Leu
        115                 120                 125

His Lys Asn Gly Glu Thr Ser Leu Lys Pro Glu Asp Phe Asp Phe Thr
    130                 135                 140

Val Leu Ser Lys Arg Gly Ile Lys Ser Arg Tyr Lys Asp Cys Ser Met
145                 150                 155                 160

Ala Ala Leu Thr Ser His Leu Gln Asn Gln Ser Asn Asn Ser Asn Trp
                165                 170                 175

Asn Leu Arg Thr Arg Ser Lys Cys Lys Lys Asp Val Phe Met Pro Pro
            180                 185                 190

Ser Ser Ser Ser Glu Leu Gln Glu Ser Arg Gly Leu Ser Asn Phe Thr
        195                 200                 205

Ser Thr His Leu Leu Leu Lys Glu Asp Glu Gly Val Asp Asp Val Asn
    210                 215                 220

Phe Arg Lys Val Arg Lys Pro Lys Gly Lys Val Thr Ile Leu Lys Gly
225                 230                 235                 240

Ile Pro Ile Lys Lys Thr Lys Lys Gly Cys Arg Lys Ser Cys Ser Gly
                245                 250                 255

Phe Val Gln Ser Asp Ser Lys Arg Glu Ser Val Cys Asn Lys Ala Asp
            260                 265                 270

Ala Glu Ser Glu Pro Val Ala Gln Lys Ser Gln Leu Asp Arg Thr Val
        275                 280                 285

Cys Ile Ser Asp Ala Gly Ala Cys Gly Glu Thr Leu Ser Val Thr Ser
    290                 295                 300

Glu Glu Asn Ser Leu Val Lys Lys Glu Arg Ser Leu Ser Ser Gly
305                 310                 315                 320

Ser Asn Phe Cys Ser Glu Gln Lys Thr Ser Gly Ile Ile Asn Lys Phe
                325                 330                 335

Cys Ser Ala Lys Asp Ser Glu His Asn Glu Lys Tyr Glu Asp Thr Phe
            340                 345                 350

Leu Glu Ser Glu Glu Ile Gly Thr Lys Val Glu Val Val Glu Arg Lys
        355                 360                 365

Glu His Leu His Thr Asp Ile Leu Lys Arg Gly Ser Glu Met Asp Asn

```
                    370                 375                 380
Asn Cys Ser Pro Thr Arg Lys Asp Phe Thr Gly Glu Lys Ile Phe Gln
385                 390                 395                 400

Glu Asp Thr Ile Pro Arg Thr Gln Ile Glu Arg Arg Lys Thr Ser Leu
                405                 410                 415

Tyr Phe Ser Ser Lys Tyr Asn Lys Glu Ala Leu Ser Pro Pro Arg Arg
            420                 425                 430

Lys Ala Phe Lys Lys Trp Thr Pro Arg Ser Pro Phe Asn Leu Val
        435                 440                 445

Gln Glu Thr Leu Phe His Asp Pro Trp Lys Leu Leu Ile Ala Thr Ile
450                 455                 460

Phe Leu Asn Arg Thr Ser Gly Lys Met Ala Ile Pro Val Leu Trp Lys
465                 470                 475                 480

Phe Leu Glu Lys Tyr Pro Ser Ala Glu Val Ala Arg Thr Ala Asp Trp
                485                 490                 495

Arg Asp Val Ser Glu Leu Leu Lys Pro Leu Gly Leu Tyr Asp Leu Arg
            500                 505                 510

Ala Lys Thr Ile Val Lys Phe Ser Asp Glu Tyr Leu Thr Lys Gln Trp
        515                 520                 525

Lys Tyr Pro Ile Glu Leu His Gly Ile Gly Lys Tyr Gly Asn Asp Ser
530                 535                 540

Tyr Arg Ile Phe Cys Val Asn Glu Trp Lys Gln Val His Pro Glu Asp
545                 550                 555                 560

His Lys Leu Asn Lys Tyr His Asp Trp Leu Trp Glu Asn His Glu Lys
                565                 570                 575

Leu Ser Leu Ser
            580

<210> SEQ ID NO 39
<211> LENGTH: 294
<212> TYPE: PRT
<213> ORGANISM: Deinococcus radiodurans

<400> SEQUENCE: 39

Gln Leu Gly Leu Val Cys Leu Thr Val Gly Pro Glu Val Arg Phe Arg
1               5                   10                  15

Thr Val Thr Leu Ser Arg Tyr Arg Ala Leu Ser Pro Ala Glu Arg Glu
            20                  25                  30

Ala Lys Leu Leu Asp Leu Tyr Ser Ser Asn Ile Lys Thr Leu Arg Gly
        35                  40                  45

Ala Ala Asp Tyr Cys Ala Ala His Asp Ile Arg Leu Tyr Arg Leu Ser
    50                  55                  60

Ser Ser Leu Phe Pro Met Leu Asp Leu Ala Gly Asp Asp Thr Gly Ala
65                  70                  75                  80

Ala Val Leu Thr His Leu Ala Pro Gln Leu Leu Glu Ala Gly His Ala
                85                  90                  95

Phe Thr Asp Ala Gly Val Arg Leu Leu Met His Pro Glu Gln Phe Ile
            100                 105                 110

Val Leu Asn Ser Asp Arg Pro Glu Val Arg Glu Ser Ser Val Arg Ala
        115                 120                 125

Met Ser Ala His Ala Arg Val Met Asp Gly Leu Gly Leu Ala Arg Thr
    130                 135                 140

Pro Trp Asn Leu Leu Leu His Gly Gly Lys Gly Gly Arg Gly Ala
145                 150                 155                 160
```

```
Glu Leu Ala Ala Leu Ile Pro Asp Leu Pro Asp Pro Val Arg Leu Arg
                165                 170                 175
Leu Gly Leu Glu Asn Asp Glu Arg Ala Tyr Ser Pro Ala Glu Leu Leu
            180                 185                 190
Pro Ile Cys Glu Ala Thr Gly Thr Pro Leu Val Phe Asp Ala His His
        195                 200                 205
His Val Val His Asp Lys Leu Pro Asp Gln Glu Asp Pro Ser Val Arg
    210                 215                 220
Glu Trp Val Leu Arg Ala Arg Ala Thr Trp Gln Pro Pro Glu Trp Gln
225                 230                 235                 240
Val Val His Leu Ser Asn Gly Ile Glu Gly Pro Gln Asp Arg Arg His
                245                 250                 255
Ser His Leu Ile Ala Asp Phe Pro Ser Ala Tyr Ala Asp Val Pro Gln
            260                 265                 270
Ile Glu Val Glu Ala Lys Gly Lys Glu Glu Ala Ile Ala Ala Leu Arg
        275                 280                 285
Leu Met Ala Pro Phe Lys
    290
```

<210> SEQ ID NO 40
<211> LENGTH: 39
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 40
cacagactcc ctctgtcata ggtttgagtt tatatggaa                    39

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 41
ttccatataa actcaaacct atgacagagg gagtctgtg                    39

<210> SEQ ID NO 42
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 42
cacagactcc ctctgtcata ggttcatgag tttatatgga a                 41

<210> SEQ ID NO 43
<211> LENGTH: 43
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 43
cacagactcc ctctgtcata ggttcacatg agtttatatg gaa               43

```
<210> SEQ ID NO 44
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 44
cacagactcc ctctgtcata ggttcacaca tgagtttata tggaa          45

<210> SEQ ID NO 45
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 45
cacagactcc ctctgtcata ggttcacaca catgagttta tatggaa        47

<210> SEQ ID NO 46
<211> LENGTH: 53
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 46
cacagactcc ctctgtcata ggttgagtac tagtactctg agtttatatg gaa    53

<210> SEQ ID NO 47
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 47
cgttagaact ccgtcacgaa ttaagcaatt agtaatgcat t              41

<210> SEQ ID NO 48
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 48
aatgcattac taattgctta attcgtgacg gagttctaac g              41

<210> SEQ ID NO 49
<211> LENGTH: 43
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 49
cgttagaact ccgtcacgaa ttaagcaatt caagtaatgc att            43
```

<210> SEQ ID NO 50
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 50
cgttagaact ccgtcacgaa ttaagcaatt cacaagtaat gcatt                    45

<210> SEQ ID NO 51
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 51
cgttagaact ccgtcacgaa ttaagcaatt cacacaagta atgcatt                  47

<210> SEQ ID NO 52
<211> LENGTH: 49
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 52
cgttagaact ccgtcacgaa ttaagcaatt cacacacaag taatgcatt                49

<210> SEQ ID NO 53
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 53
cgttacaagt ccgtcacgaa ttaagcaatt cgtaacgcat t                        41

<210> SEQ ID NO 54
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 54
aatgcattac gaattgctta attcgtgacg gacttgtaac g                        41

<210> SEQ ID NO 55
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 55
cgttacaagt ccgtcacgaa ttaagcaatt cgtaacgcat t                        41

<210> SEQ ID NO 56

```
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 56
aatgcgttac aaattgctta attcgtgacg gacttgtaac g                    41

<210> SEQ ID NO 57
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 57
cgttacaagt ccgtcacgaa ttaagcaatt cgtaacgcat t                    41

<210> SEQ ID NO 58
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 58
aatgcgttac gaattactta attcgtgacg gacttgtaac g                    41

<210> SEQ ID NO 59
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 59
cgttacaagt ccgtcacgac ttaagcaatt cgtaacgcat t                    41

<210> SEQ ID NO 60
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 60
aatgcgttac gaattgctta aatcgtgacg gacttgtaac g                    41

<210> SEQ ID NO 61
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 61
cgttacaagt ccgtcacgaa ttaagcaatt cgtaacgcat t                    41

<210> SEQ ID NO 62
<211> LENGTH: 41
```

<210> SEQ ID NO 62
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 62
aatgcgttac gaattgctta attcgtaacg gacttgtaac g                          41

<210> SEQ ID NO 63
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 63
cgttacaagc ccgtcacgaa ttaagcaatt cgtaacgcat t                          41

<210> SEQ ID NO 64
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 64
aatgcgttac gaattgctta attcgtgacg gacttgtaac g                          41

<210> SEQ ID NO 65
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 65
cgttccaagt ccgtcacgaa ttaagcaatt cgtaacgcat t                          41

<210> SEQ ID NO 66
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 66
aatgcgttac gaattgctta attcgtgacg gacttgaaac g                          41

<210> SEQ ID NO 67
<211> LENGTH: 78
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 67
tgcacggacc tcgagagaac cgaacgatcc ggatgtgatc atgggacaga attcgcacac      60
tgcactcgac gatagtct                                                   78

<210> SEQ ID NO 68

```
<211> LENGTH: 49
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 68
tgcagtgtgc gaattctgtc ccatcatcac atccggatcg ttcggttct          49

<210> SEQ ID NO 69
<211> LENGTH: 62
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 69
gactatcgtg cagtgcagtg tgcgaattct gtcccatcat cacatccgga tcgttcggtt    60
ct                                                                  62

<210> SEQ ID NO 70
<211> LENGTH: 64
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 70
tgcagtgtgc gaattctgtc ccatcatcac atccggatcg ttcggttctc tcgaggtccg    60
tgca                                                                64

<210> SEQ ID NO 71
<211> LENGTH: 79
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 71
gagactatcg tgcagtgcag tgtgcgaatt ctgtcccatc atcacatccg gatcgttcgg    60
ttctctcgag gtccgtgca                                                79
```